(12) United States Patent
Hoch et al.

(10) Patent No.: US 6,368,793 B1
(45) Date of Patent: Apr. 9, 2002

(54) METABOLIC SELECTION METHODS

(75) Inventors: James Hoch, La Jolla; Veronique Dartois, San Diego, both of CA (US)

(73) Assignee: MicroGenomics, Inc., Carlsbad, CA (US)

( * ) Notice: Subject to any disclaimer, the term of this patent is extended or adjusted under 35 U.S.C. 154(b) by 0 days.

(21) Appl. No.: 09/172,952

(22) Filed: Oct. 14, 1998

(51) Int. Cl.$^7$ ............... C12Q 1/68; C12N 1/12; C12N 1/20; C12N 5/00; C12N 15/86
(52) U.S. Cl. ............ 435/6; 435/252.1; 435/252.3; 435/325; 435/375
(58) Field of Search ............ 435/6, 252.1, 252.3, 435/325, 375, 419, 254.2

(56) References Cited

U.S. PATENT DOCUMENTS

| | | | |
|---|---|---|---|
| 3,691,016 A | 9/1972 | Patel | 195/68 |
| 3,969,287 A | 7/1976 | Jaworek et al. | 260/8 |
| 4,195,128 A | 3/1980 | Hildebrand et al. | 435/178 |
| 4,229,537 A | 10/1980 | Hodgins et al. | 435/177 |
| 4,247,642 A | 1/1981 | Hirohara et al. | 435/178 |
| 4,330,440 A | 5/1982 | Ayers et al. | 525/54.31 |
| 4,376,110 A | 3/1983 | David et al. | 436/513 |
| 5,032,514 A | 7/1991 | Anderson et al. | 435/138 |
| 5,753,466 A | 5/1998 | Yano et al. | 435/91.1 |
| 5,763,239 A | 6/1998 | Short et al. | 435/172.1 |
| 5,783,431 A | 7/1998 | Peterson et al. | 435/172.3 |
| 5,824,485 A * | 10/1998 | Thompson et al. | 435/6 |
| 5,908,765 A | 6/1999 | Carlson et al. | 435/91.41 |
| 5,935,824 A | 8/1999 | Sgarlato | 435/69.7 |
| 5,939,250 A | 8/1999 | Short | 435/4 |
| 5,958,672 A | 9/1999 | Short | 435/4 |
| 5,989,832 A * | 11/1999 | Trias et al. | 435/7.2 |
| 5,998,136 A | 12/1999 | Kamb | 435/6 |
| 6,001,574 A | 12/1999 | Short et al. | 435/6 |
| 6,030,779 A | 2/2000 | Short | 435/6 |
| 6,030,807 A * | 2/2000 | De Lencastre et al. | 435/69.1 |
| 6,054,267 A | 4/2000 | Short | 435/6 |
| 6,057,103 A | 5/2000 | Short | 435/6 |

FOREIGN PATENT DOCUMENTS

WO    WO 92/20791    11/1992

OTHER PUBLICATIONS

Amann and Brosius, "ATG vectors for regulated high–level expression of cloned genes in *Escherichia coli*," *Gene*, 40:183–190 (1985).
Blattner et al., "The complete genome sequence of *Escherichia coli* K–12," *Science* 277:1453–1462 (1997).
Abe, et al. "Molecular Characterization of a Novel Metabotropic Glutamate Receptor mGluR5 Coupled to Inositol Phosphate/Ca2+ Signal Transduction," *J. Biol. Chem.* 19:13361–13368 (1992).
Adelman, et al., "In Vitro Deletional Mutagenesis for Bacterial Production of the 20,000–Dalton Form of Human Pituitary Growth Hormone," *DNA* 2:183 (1983).
Applegate, et al., "A Chromosomally Based tod–luxCDABE Whole–Cell Reporter for Benzene, Toluene, Ethylbenzene, and Xylene," *Applied Environ. Microbiol.* 64:2730–2735 (1988).
Badia, et al., "A Rare 920–Kilobase Chromosomal Inversion Mediated by IS1 Transposition Causes Constitutive Expression of the yiaK–S Operon for Carbohydrate Utilization in *Escherichia coli*," *J. Biol. Chem.* 273:8376–8371 (1998).

(List continued on next page.)

*Primary Examiner*—Sean McGarry
*Assistant Examiner*—Karen A Lacourciere
(74) *Attorney, Agent, or Firm*—Campbell & Flores LLP

(57) ABSTRACT

The present invention relates in part to methods for screening for novel enzymatic pathways in environmental samples using metabolic selection strategies, and the isolation of the genes and proteins that make up these pathways.

15 Claims, 21 Drawing Sheets

OTHER PUBLICATIONS

Bayer et al., "The Avidin—Biotin Complex in Affinity Cytochemistry," *Meth. Enzym.* 62:308 (1979).
Blattner, et al., "The Complete Genome Sequence of *Escherichia coli* K–12," *Science* 277:1453–1462 (1997).
Brosius, "Compilation of Superlinker Vectors," *Meth. Enzymol.* 216:469–483 (1992).
Bullock et al., *Techniques in Immunocytochemistry*, Academic Press, Orlando, FL vol. 1 (1982), vol. 2 (1983), vol. 3 (1985) Table of Contents Only.
Cali, B. M., et al., "Genetic Regulation of Nitrate Assimilation in *Klebsiella pneumoniae* M5al," *J. Bacteriol.* 171:2666–2672 (1989).
Campbell, *Monoclonal Antibody Technology: Laboratory Tchniques in Biochemistry and Molecular Biology*, Elsevier Science Publishers, Amsterdam, The Netherlands, (1984) Table of Contents Only.
Cenatiempo, "Prokaryotic Gene Expression In Vitro: Transcription—Translation Coupled Systems," *Biochimie* 68:505–516 (1986).
Chard, "An Introduction to Radioimmunoassay and Related Techniques," Elsevier Science Publishers, Amsterdam, The Netherlands (1986) Table of Contents Only.
Chater et al., In: *Sixth International Symposium on Actinomycetales Biology*, Akademiai Kaido, Budapest, Hungary (1986) pp. 45–54.
Creighton, *Proteins: Structure and Molecular Properties*, W.H. Freeman & Co., San Francisco, pp. 79–86 (1983).
De Vries, et al., "Extension of Bacteriophage λ host range: Selection, Cloning, and Characterization of a Constitutive λ Receptor Gene," *PNAS USA* 81:6080–6084 (1984).
Engvall et al., "Enzyme–Linked Immunosorbent Assay, Elisa," *Immunot* 109:129 (1972).
Fleischman, et al., "Whole–Genome Random Sequencing and Assembly of *Haemophilus influenzae* Rd," *Science* 269:496–512 (1995).
Gilman et al., "Isolation of Sigma–28–Specific Promoters from *Bacillus Subtilis* DNA," *Gene* 32:11–20 (1984).
Glick, "Factors Affecting the Expression of Foreign Proteins in *Escherichia Coli*," *J. Ind. Microbiot.* 1:277–282 (1987).
Goding, "Conjugation of Antibodies with Fluorochromes: Modifications to the Standard Methods," *J. Immunological Methods* 13:215–226 (1976).
Gold et al., "Translational Initiation in Prokaryotes," *Ann. Rev. Microbiol.* 35:365–404 (1981).
Gottesman, "Bacterial Regulation: Global Regulatory Networks," *Ann. Rev. Genet.* 18:415–441 (1984).
Gryczan, *The Molecular Biology of the Bacilli*, Academic Press, Inc., NY (1982).
Hamilton, et al., "New Method for Generating Deletions and Gene Replacements in *Escherichia coli*," *J. Bacteriol.* 171:4617–4622 (1989).
Hurby et al., in *Synthetic Peptides: A User's Guide*, edited by Grant, Washington University School of Medicine, W.H. Freeman and Company, New York, pp. 289–307 (1992).
Innis et al., *PCR Protocols: A Guide to Methods and Applications*, edited by Michael A. Innis et al., Academic Press, San Diego (1990) (Table of Contents Only).
Jakoby et al., *Meth. Enzym.* 34:Index (1974).
John et al., "Plasmids as Epidemiologic Markers in Nosocomial Gram–Negative Bacilli: Experience at a University and Review of the Literature," *Rev. Infect. Dis.* 8:693–704 (1986).

Kasprzak et al., "Location of a Contact Site Between Actin and Myosin in the Three–Dimensional Structure of the Acto–S1 Complex," *Biochemistry* 28:9230–8 (1989).
Kendall et al., "Plasmid Transfer in *Streptomyces Lividans:* Identification of a kil–kor System Associated with the Transfer Region of pIJ101," *J. Bacteriol.* 169:4177–4183 (1987).
Köhler (Kohler) and Milstein, "Continuous cultures of fused cells secreting antibody of predefined specificity," *Nature* 256:495–497 (1975).
Lutz et al., "The Distribution of Two hnRNP–Associated Proteins Defined by a Monoclonal Antibody Is Altered in Heat–Shocked HeLa Cells," *Experimental Cell Research* 175:109–124 (1988).
Metzger, et al., "Site–directed and Transposon–mediated Mutagenesis with pfd–plasmids by Electroporation of *Erwinia Amylovora* and *Escherichia coli* cells," *Nucl. Acids Res.* 20:2265–2270 (1992).
Murphy, "Nucleotide Sequence of a Spectinomycin Adenyltransferase AAD(9) Determinant from *Staphylococcus aureus* and its relationship to AAD(3") (9)," *Mol. Gen. Genet.* 200:33–39 (1985).
Nelson, "Detection of Acridinium Esters by Chemiluminescence," *Nonisotopic DNA Probe Techniques*, ed. Larry J. Kricka, (San Diego: Academic Press, Inc.) pp. 275–310 (1992).
Okayama, "A cDNA Cloning Vector That Permits Expression of cDNA Inserts in Mammalian Cells," *Molec. Cell. Bio.* 3:280 (1983).
*Remington's Pharmaceutical Sciences*, $18^{th}$ ed., Mack Publishing Co., Easton, PA 1990 (Table of Contents Only).
Sambrook et al., *Molecular Cloning: A Laboratory Manual, $2^{nd}$ Edition*, Cold Spring Harbor Press (1989) (Table of Contents for vols. 1, 2 and 3).
Sanchez, et al., "Activation of a Cryptic Gene Encoding a Kinase for L–Xylulose Opens a New Pathway for the Utilization of L–Lyxose by *Escherichia coli*," *J. Biol. Chem.* 169:29665 (1994).
Selifonova and Eaton, "Use of an ipb–lux Fusion to Study Regulation of the Isopropylbenzene Catabolism Operon of *Pseudomonas putida* RE204 and to Detect Hydrophobic Pollutants in the Environment," *Applied Environ. Microbiol.* 62:778–783 (1996).
Simpson, et al., "Bioluminescent–bioreporter Integrated Circuits Form Novel Whole–cell Biosensors," *TIBTECH* 16:332–338 (1988).
St. Groth et al., "Production of Monoclonal Antibodies: Strategy and Tactics," *J. Immunol. Methods* 35:1–21 (1980).
Steffan, et al., "Recovery of DNA from Soils and Sediments," *Appl. Environ. Microbiol.* 54:2908–2915 (1988).
Stemberger et al., "The Unlabeled Antibody Enzyme Method of Immunohistochemistry," *J. Histochem. Cytochem.* 18:315 (1970).
Tijssen, "Practice and Theory of Enzyme Immunoassays," *Laboratory Techniques in Biochemistry and Molecular Biology*, Elsevier Science Publishers, Amsterdam, The Netherlands (1985).
Ulmanen et al., "Transcription and Translation of Foreign Genes in *Bacillus Subtilis* by the Aid of a Secretion Vector," *J. Bacteriol.* 162:176–182 (1985).
Ward et al., "Construction and Characterisation of a Series of Multi–copy Promoter–probe Plasmid Vectors for Streptomyces Using the Aminoglycoside Phosphotransferase Gene From Tn5 as Indicator," *Mol. Gen. Genet.* 203:468–478 (1986).

Weir et al., *Handbook of Experimental Immunology*, 4th Ed., Blackwell Scientific Publications, Oxford, England, Chapter 10, (1986).

Whatling, et al., "Preeletrophoresis of Agarose Plugs Containing Bacterial Chromosomal DNA Prepared for Analysis by Pulsed Field Gel Electrophoresis Can Improve the Clarity of Restriction Patterns," *Anal. Biochem.* 210:98–101 (1993).

Zhou, et al., "DNA Recovery from Soils of Diverse Composition," *Appl. Environ. Microbiol.* 62:316–322 (1996).

* cited by examiner

```
GGATCCGCGGGCGCAAAGGCGGAGACGCCAGAACAGTCCTGGTCCTGCTGATGGGACACCACGCAGGCGACTTCACAGGT
ACGGCAGCCGATGCACTTCTCCGCATCCGCGAGAATAAACCGATTCATCCTTCTCCATTGGGGATAAAAACGCAGAGTGC
CAGAAAAAACCCGCTTTCCTCTCCCTTTGATCCTGAATGGAGTCAGCGGCGTTTTCTCTCAGATGTCCGGGATTATCTGG
        *  G  E  R  V  S  F  G  L  E  R  S  I  A  E  A  T  D  R  L  P  K  L
TCATTTGCCTTAACCTTCCCGCACGGAAAAGCCCAGTTCGCGAGAAATCGCCTCTGCCGTATCGCGTAGCGGCTTGAGTA
 L  N  K  E  G  V  Q  K  L  R  S  T  S  L  S  I  S  I  A  Y  P  V  R  G  H  I  D
AATTTTTCTCTCCCACCTGCTTGAGGCGCGATGTTGATAGAGAGATAGAAATGGCATAAGGCACGCGCCCATGGATATCA
  F  V  P  V  A  L  C  S  V  G  L  E  N  E  E  R  D  M  A  M  N  R  E  R  I  Q  A
AAAACGGGGACAGCCAGGCACGACACGCCCAGCTCGTTCTCTTCCCTGTCCATCGCCATATTTCGCTCGCGGATCTGCGC
   L  E  D  H  M  A  P  L  G  T  I  T  N  R  T  L  P  Q  I  I  E  Q  H  S  N  W
CAGTTCATCATGCATCGCAGGCAAGCCGGTAATGGTATTACGGGTCAGCGGCTGGATAATCTCCTGGTGTGAATTCCAGT
   Y  S  E  V  Y  D  P  H  G  F  A  M  Y  I  K  A  W  Q  R  A  T  C  R  M  H  Q  G
AGCTCTCAACGTAGTCAGGATGGCCAAACGCCATATAAATCtTTGCCCATTGCCGAGCAGTACAGCGCATGTGCTGGCCA
    I  Y  A  R  T  R  L  M  G  T  T  P  E  L  K  Y  I  L  I  A  H  D  D  E  R  S  S
ATATAGGCGCGCGTACGCAGCATACCGGTGGTCGGCTCCAGCTTATAAATCAGGATCGCGTGGTCATCTTCACGGCTGGA
    F  N  V  T  E  G  T  A  L  N  L  A  E  L  H  P  A  A  V  H  I  I  N  L  S  S
GAAGTTCACCGTCTCGCCGGTGGCCAGGTTAAgCGCCTCAAGATGCGGCGCCGCGACGTGGATAATATTCAGCGACGACA
  L  A  K  Q  G  V  R  I  F  K  T  T  L  A  Y  S  G  A  A  P  A  P  T  V  Y  G  C
ACGCCTTTTGGCCAACGCGGATAAATTTTGTCGTCAGCGCATAGCTCCCCGCCGCCGGGgCAGGCGTCACGTACCCGCAG
   S  Q  L  G  Q  L  L  R  H  V  T  S  K  N  L  G  A  L  E  S  L  H  A  V  P  C  G
GACTGCAGCCCCTGTAATAAGCGATGAACGGTACTTTTGTTCAGTCCCGCCAGTTCCGACAGATGCGCCACGGGACAGCC
    N  P  Y  N  S  L  I  E  I  L  M  L  G  R  F  L  S  Q  S  G  A  P  R  E  K  D
ATTTGGATAATTACTCAGGATCTCAATTAGCATCAACCCACGAAAAAGGCTCTGACTTCCGGCAGGCCTCTCTTTATCTT
  Q  T  N  E  S  E  K  T  G  M
GCGTGTTCTCGCTTTCTTTTGTGCCCATCGCTTCCGCTCCCATTTTTGTCGCGTTCAGATGGTAGCGCAAAGTGTGTTTC
                    yiaJ ←
AGTTCACGATCTGAACCGAAAAAACACAACTTTATGATTTTTATGATTTTTAAAAATAACGCTGCCCGTTGATCTGACAA
```

Fig. 2A

```
AAATTGATCGCTATATTTGAAATCAGATTTCGCATAGTGAAATTTAGAGATAAAAAAGCGATCAACTCTGACCAGGAAAA
  →yiaK
CAGCAATGAAAGTCACGTTTGAGCAGTTAAAAGAGGCATTCAATCGGGTACTGCTGGACgcgtgcgtcgcccgGGAAACC
   M  K  V  T  F  E  Q  L  K  E  A  F  N  R  V  L  L  D  A  C  V  A  R  E  T GCCGATGCCTGCGCAGAAATGTTTGCCCGCACCACCGAATCCGGCGTCTATTCTCACGGCGTGAACCGCTTTCCTCGCTT
 A  D  A  C  A  E  M  F  A  R  T  T  E  S  G  V  Y  S  H  G  V  N  R  F  P  R  F CATCCAGCAGTTGGATAACGGCGACATTATCCCTGAGGCTCAACCGCAGCGGGTGACCACGCTCGGCGCCATCGAACAGT
 I  Q  Q  L  D  N  G  D  I  I  P  E  A  Q  P  Q  R  V  T  T  L  G  A  I  E  Q  W GGGATGCTCAGCGTTCCATCGGCAACCTGACGGCGAAAAAGATGATGGATCGGGCCATTGAGCTGGCCTCCGATCACGGT
 D  A  Q  R  S  I  G  N  L  T  A  K  K  M  M  D  R  A  I  E  L  A  S  D  H  G ATCGGCCTGGTCGCCTTACGTAATGCTAACCACTGGATGCGCGGCGGCAgcTACGGCTGGCAGGCGGCGGAAAAAGGCTA
 I  G  L  V  A  L  R  N  A  N  H  W  M  R  G  G  S  Y  G  W  Q  A  A  E  K  G  Y CATCGGTATCTGCTGGACCAACTCCATCGCCGTTATGgcGCCATGGGGCGCTAAAGAGTGCCGTATCGGTACCAACCCGC
 I  G  I  C  W  T  N  S  I  A  V  M  A  P  W  G  A  K  E  C  R  I  G  T  N  P  L TGATCGTCGCCATTCCGTCGACGCCGATCACCATGGTGGATATGTCGATGTCGATGTTCTCCTACGGCATGCTGGAGGTT
  I  V  A  I  P  S  T  P  I  T  M  V  D  M  S  M  S  M  F  S  Y  G  M  L  E  V
AACCGCCTTGCCGGCCGCGAACTGCCCGTGGACGGCGGATTCGACGATGACGGTCGTTTTGACCAAAGAGCCGGGGACGAT
  N  R  L  A  G  R  E  L  P  V  D  G  G  F  D  D  D  G  R  L  T  K  E  P  G  T  I CGAGAAAAATCGCCGCATTTTACCCATGGGCTACTGGAAAGGTTCCGGCCTGTCGATCGTGCTGGATATGATTGCCACCC
 E  K  N  R  R  I  L  P  M  G  Y  W  K  G  S  G  L  S  I  V  L  D  M  I  A  T  L TCCTCTCCAACGGATCGTCGGTTGCCGAAGTGACCCAGGAAAACAGCGATGAATATGGCGTTTCGCAGATCTTCATCGCT
 L  S  N  G  S  S  V  A  E  V  T  Q  E  N  S  D  E  Y  G  V  S  Q  I  F  I  A ATTGAAGTGGATAAGCTGATCGACGGCGCAACCCGCGACGCCAAGCTGCAACGGATTATGGATTTCATCACCACCGCCGA
 I  E  V  D  K  L  I  D  G  A  T  R  D  A  K  L  Q  R  I  M  D  F  I  T  T  A  E GCGCGCCGATGAAAATGTGGCGGTCCGTCTTCCTGGCCATGAATTTACCCGTCTGCTGGATGAAAACCGCCGCAACGGCA
 R  A  D  E  N  V  A  V  R  L  P  G  H  E  F  T  R  L  L  D  E  N  R  R  N  G  I
```

Fig. 2B

```
TTACCGTCGATGACAGCGTATGGGCCAAAATTCAGGCGCTGTAAGGAGCTCACCCATGACAGCGTATGGGCCAAAATTCA
 T  V  D  D  S  V  W  A  K  I  Q  A  L  *
                              →yiaL
GGCGCTGTAAGGAGCTCACCCATGATTTTTGGTCATATTGCTCAACCTAATCCGTGTCGTCTGCCCGCGGCCATTGAGCG
                         M  I  F  G  H  I  A  Q  P  N  P  C  R  L  P  A  A  I  E  R
GGCGCTTGATTTCCTGCGCACGACGGATTTCCACGCGCTGGCACCCGGCGTCGTGGAAATCGACGGCCAAAACATCTTCG
 A  L  D  F  L  R  T  T  D  F  H  A  L  A  P  G  V  V  E  I  D  G  Q  N  I  F  A
CGCAGGTTATCGACTTAACCACTCGCGATGCCGCTGAAAATCGTCCGGAGGTCCACCGTCGCTATCTGGATATCCAGTTT
 Q  V  I  D  L  T  T  R  D  A  A  E  N  R  P  E  V  H  R  R  Y  L  D  I  Q  F
CTGGCATCGGGCGAAgAAAAAATCGGTATCGCCATTGATACCGGCAATAATCAAATCAGCGAATCTTTATTAGAACAGCG
 L  A  S  G  E  E  K  I  G  I  A  I  D  T  G  N  N  Q  I  S  E  S  L  L  E  Q  R
CGATATTATTTTTTATCACGACAGCGAACATGAATCGTTCTTTGAAATGACGCCAGGCAACTATGCGATATTTTTCCCGC
 D  I  I  F  Y  H  D  S  E  H  E  S  F  F  E  M  T  P  G  N  Y  A  I  F  F  P  Q
AAGATGTTCATCGTCCTGGATGTAATAAAACTGTAGCCACGCCGATCCGCAAAATAGTCGTTAAAGTCGCTATTTCAGTT
 K  D  V  H  R  P  G  C  N  K  T  V  A  T  P  I  R  K  I  V  V  K  V  A  I  S  V
                         →orf1
TTATAAGAAGGAGCACAAAATGAATTCGAATAATACCGGTTACATTATCGGTGCGTACCCCTGTGCCCCCTGTGCACCCT
 L  *           M  N  S  N  N  T  G  Y  I  I  G  A  Y  P  C  A  P  C  A  P  S
CATTTCACCAAAAGAGTGAAGAGGAAGAGaTGGAATTCTGGCGGCAGCTCTCCGACACCCCGGATATTCGCGGGCTGGAG
 F  H  Q  K  S  E  E  E  E  M  E  F  W  R  Q  L  S  D  T  P  D  I  R  G  L  E
CAACCCTGCCTACCCTGCCTTGAACATCTTCATCCGCTCGGCGACGAGTGGTTATTGCGCCATACCCCGGGACACTGGCA
 Q  P  C  L  P  C  L  E  H  L  H  P  L  G  D  E  W  L  L  R  H  T  P  G  H  W  Q
GATTGTCGTTACCGCCATCATGGAAACCATGCGCCGCCGCGGTGAAAACGGCGGCTTTGGGCTGGCGTCCAGCGACGAAA
 I  V  V  T  A  I  M  E  T  M  R  R  R  G  E  N  G  G  F  G  L  A  S  S  D  E  T
CGCAGCGCAAAGCCTGCGTGGAGTACTATCGCCACCTGCAGCAGAAGATCGCTAAAATCAATGGCAATACCGCCGGAAAG
 Q  R  K  A  C  V  E  Y  Y  R  H  L  Q  Q  K  I  A  K  I  N  G  N  T  A  G  K
GTCATTGCCCTTGAGCTTCACGCCGCCCCGCTGGCGGGCAATGCCAACGTGGCTCAGGCTACCGACGCCTTTGCCCGTTC
 V  I  A  L  E  L  H  A  A  P  L  A  G  N  A  N  V  A  Q  A  T  D  A  F  A  R  S
```

Fig. 2C

```
ATTAAAAGAAATTACCCGCTGGGACTGGTCCTGCGAGCTGGTGCTGGAGCACTGCGACGCGATGACCGGCAGCGCGCCGC
 L  K  E  I  T  R  W  D  W  S  C  E  L  V  L  E  H  C  D  A  M  T  G  S  A  P  R

GCAAAGGATTTTTGCCGTTAGAAAACGTGCTGGAAGCCATTGCCGATTATGACGTTgGCATTTGTATTAACTGGGCGCGT
 K  G  F  L  P  L  E  N  V  L  E  A  I  A  D  Y  D  V  G  I  C  I  N  W  A  R

TCGGCCATTGAAGGGCGGAATACCGTGCTACCGCTCACCCATACGCAGCAGGTAAAACGGGCAGGAAAGCTCGGCGCGCT
 S  A  I  E  G  R  N  T  V  L  P  L  T  H  T  Q  Q  V  K  R  A  G  K  L  G  A  L

GATgTTTTCTGGCACGACGCAgACCGGCGAGTACGGCGAATGGCAGGATTTACACGCGCCGTTCGCGCCTTTCTGCCCGC
 M  F  S  G  T  T  Q  T  G  E  Y  G  E  W  Q  D  L  H  A  P  F  A  P  F  C  P  Q

AgAGCCTGATGACCACCGAACACGCTCGTGAATTATTTGCCTGCGCAGGAACCGCCCCCCTGCAATTTTCAGGCATTAAA
 S  L  M  T  T  E  H  A  R  E  L  F  A  C  A  G  T  A  P  L  Q  F  S  G  I  K

TTACTGGAAATTAATGCCAGCGCAAACGTTGATCATCGCATCGCGATATTACGCGACGGCATCTCCGCGCTAAAACAAGC
 L  L  E  I  N  A  S  A  N  V  D  H  R  I  A  I  L  R  D  G  I  S  A  L  K  Q  A
                                                                    →yiaX2
ACAATAATAATAATCACCTTCATCACCAGAATATTTTTAATATTACGAGACTATAAAGAtgAATATAACCTCTAACTCTA
 Q  *                                                       M  N  I  T  S  N  S  T CAACCAAAGATATACCGCGCCAGCGCTGGTTAAGAATCATTCCGCCTATACTGATCACTTGTATTATTTCTTATATGGAC
 T  K  D  I  P  R  Q  R  W  L  R  I  I  P  P  I  L  I  T  C  I  I  S  Y  M  D CGGGTCAATATTGCCTTTGCGATGCCCGGAGGTATGGATGCCGACTTAGGTATTTCCGCCACCATGGCGGGGCTGGCGGG
 R  V  N  I  A  F  A  M  P  G  G  M  D  A  D  L  G  I  S  A  T  M  A  G  L  A  G CGGTATTTTCTTTATCGGTTATCTATTTTTACAGGTTCCCGGCGGGAAAATTGCCGTTCACGGTAGCGGTAAGAAATTTA
 G  I  F  F  I  G  Y  L  F  L  Q  V  P  G  G  K  I  A  V  H  G  S  G  K  K  F  I TCGGCTGGTCGCTGGTCGCCTGGGCGGTCATCTCCGTGCTGACGGGGTTAATTACCAATCAGTACCAGCTGCTGGCCCTG
 G  W  S  L  V  A  W  A  V  I  S  V  L  T  G  L  I  T  N  Q  Y  Q  L  L  A  L CGCTTCTTACTGGGCGTGGCGGAAGGCGGTATGCTGCCGGTCGTTCTCACGATGATCAGTAACTGGTTCCCCGACGCTGA
 R  F  L  L  G  V  A  E  G  G  M  L  P  V  V  L  T  M  I  S  N  W  F  P  D  A  E ACGCGGTCGCGCCAACGCGATTGTCATTATGTTTGTGCCGATTGCCGGGATTATCACCGCCCCACTCTCAGGCTGGATTA
 R  G  R  A  N  A  I  V  I  M  F  V  P  I  A  G  I  I  T  A  P  L  S  G  W  I  I
```

Fig. 2D

```
TCACGGTTCTCGACTGGCGCTGGCTGTTTATTATCGAAGGTTTGCTCTCGCTGGTTGTTCTGGTTCTGTGGGCATACACC
  T  V  L  D  W  R  W  L  F  I  I  E  G  L  L  S  L  V  V  L  V  L  W  A  Y  T

ATCTATGACCGTCCGCAGGAAGCGCGCTGGATTTCCGAAGCAGAGAAGCGCTATCTGGTCGAGACGCTGGCCGCGGAGCA
  I  Y  D  R  P  Q  E  A  R  W  I  S  E  A  E  K  R  Y  L  V  E  T  L  A  A  E  Q

AAAAGCCATTGCCGGCACCGAGGTGAAAAACGCCTCTCTGAGCGCCGTTCTCTCCGACAAAACCATGTGGCAGCTTATCG
  K  A  I  A  G  T  E  V  K  N  A  S  L  S  A  V  L  S  D  K  T  M  W  Q  L  I  A

CCCTGAACTTCTTCTACCAgACCGGCATTTACGGCTACaCCCTGTGGCTACCCACCATTCTGAAAGAATTGACCCATAGC
  L  N  F  F  Y  Q  T  G  I  Y  G  Y  T  L  W  L  P  T  I  L  K  E  L  T  H  S

AGCATGGGGCAGGTCGGCATGCTTGCCATTCTGCCGTACGTCGGCGCCATTGCTGGGATGTTCCTGTTTTCCTCCCTTTC
  S  M  G  Q  V  G  M  L  A  I  L  P  Y  V  G  A  I  A  G  M  F  L  F  S  S  L  S

AGACCGAACCGGTAAACGCAAGCTGTTCGTCTGCCTGCCGCTgATTGGCTTCGCTCTGTGCATGTTCCTGTCGGTGGCGC
  D  R  T  G  K  R  K  L  F  V  C  L  P  L  I  G  F  A  L  C  M  F  L  S  V  A  L

TgAAAAACCAAATTTGGCTCTCCTATGCCGCGCTGGTCGGCTGCGGATTCTTCCTGCAATCGGCGGCTGGCGTGTTCTGG
  K  N  Q  I  W  L  S  Y  A  A  L  V  G  C  G  F  F  L  Q  S  A  A  G  V  F  W

ACCATCCCGGCACGTCTGTTCAGCGCGGAAATGGCGGGCGGCGCGCGCGGGGTTATCAACGCGCTTGGCAACCTCGGCGG
  T  I  P  A  R  L  F  S  A  E  M  A  G  G  A  R  G  V  I  N  A  L  G  N  L  G  G

ATTTTGTGGCCCTTATGCGGTCGGGGTGCTGATCACGTTgTACAGCAAAGACGCTgGCGTCTATTGCCTGGCGATCTCCC
  F  C  G  P  Y  A  V  G  V  L  I  T  L  Y  S  K  D  A  G  V  Y  C  L  A  I  S  L

TGGCGCTGGCCGCGCTGATgGCGCTgCTGCTGCCGGCGAAATGCGATGCCgGTGCTGCGCCGGTaAAgACgATAAaTCCA
  A  L  A  A  L  M  A  L  L  L  P  A  K  C  D  A  G  A  A  P  V  K  T  I  N  P

CATAAACGCACTGCGTAAACTCGAGCCCGGCGGCGCTgCGCCTGCCGGGCCTGCGAAATATGCCGGGTTCACCCGGTaAC
  H  K  R  T  A  *
                    → lyxK
AATgAGATGCgAAAgATGAGCAAgAAACAgGCCTTCTGGCTGGGTATTGATTGCGGCGGCACCTATCTGAAAGCCGGTTT
                    M  S  K  K  Q  A  F  W  L  G  I  D  C  G  G  T  Y  L  K  A  G  L ATATGACGCCGAAGGTCATGAACATGGCATTGTGCGGCAAGCGCTACGGACGATGTCGCCCCTGCCGGGTTACGCCGAAC
  Y  D  A  E  G  H  E  H  G  I  V  R  Q  A  L  R  T  M  S  P  L  P  G  Y  A  E  R
```

Fig. 2E

```
GCGACATGCGCCAGCTCTGGCAACACTGCGCGGCGACCATTGCCGGGCTATTACAGCAGGCAGGTGTATCCGGCGAACAG
  D  M  R  Q  L  W  Q  H  C  A  A  T  I  A  G  L  L  Q  Q  A  G  V  S  G  E  Q
ATTAAAGGCGTGGGCATCTCCGCTCAGGGTCAAGGGCTCTTTCTCCTCGATAAGCAGGATCGGCCGCTGGGTAACGCCAT
  I  K  G  V  G  I  S  A  Q  G  Q  G  L  F  L  L  D  K  Q  D  R  P  L  G  N  A  I
CCTCTCCTCCGATCGTCGGGCGCTGAAAATCGTTCAGCGCTGGCAGCGGGACCGTATTCCCGAACGGCTCTATCCCGTTA
  L  S  S  D  R  R  A  L  K  I  V  Q  R  W  Q  R  D  R  I  P  E  R  L  Y  P  V  T
CCCGCCAGACGCTGTGGACCGGACATCCGGCTTCTTTGCTGCGCTGGGTAAAAGAGAATGAACCCCAGCGCTACGCGCAA
  R  Q  T  L  W  T  G  H  P  A  S  L  L  R  W  V  K  E  N  E  P  Q  R  Y  A  Q
ATTGGCTGCGTGATGATGGGGCATGACTATCTGCGCTGGTGCTTAACCGGCGCGAAGGGCTGCGAGGAGAGCAACATCTC
  I  G  C  V  M  M  G  H  D  Y  L  R  W  C  L  T  G  A  K  G  C  E  E  S  N  I  S
CGAGTCCAACCTCTACAACATGGCCATGGGCCAGTACGACCCGCGCCTGACCGAGTGGCTGGGCATCGGTGAAATCGATA
  E  S  N  L  Y  N  M  A  M  G  Q  Y  D  P  R  L  T  E  W  L  G  I  G  E  I  D  S
GCGCGCTGCCCCCCGTTGTAGGGTCAGCCGAAATTTGCGGGGAGATCACCGCTCAGGCAGCCGCTTTAACCGGTCTGGCG
  A  L  P  P  V  V  G  S  A  E  I  C  G  E  I  T  A  Q  A  A  A  L  T  G  L  A
GCGGGTACTCCCGTCGTTGGCGGCCTGTTTGACGTGGTCTCCACCGCCCTTTGCGCCGGGATTGAGGATGAGTCGACCCT
  A  G  T  P  V  V  G  G  L  F  D  V  V  S  T  A  L  C  A  G  I  E  D  E  S  T  L
CAATGCGGTGATGGGGACCTGGGCCGTCACTAGCGGTATCGCTCACGGCCTGCGCGACCATGAGGCCCACCCTTACGTCT
  N  A  V  M  G  T  W  A  V  T  S  G  I  A  H  G  L  R  D  H  E  A  H  P  Y  V  Y
ATGGCCGCTACGTCAATGACGGCCGTATATCGTTCACGAAGCCAGCCCGACCTCATCCGGCAACCTCGAATGGTTTACC
  G  R  Y  V  N  D  G  Q  Y  I  V  H  E  A  S  P  T  S  S  G  N  L  E  W  F  T
GCCCAGTGGGGCGATCTCTCGTTTGATGAGATCAATCAGGCCGTCGCCAGCCTGCCGAAAGCCGGGAGCGAGCTGTTTTT
  A  Q  W  G  D  L  S  F  D  E  I  N  Q  A  V  A  S  L  P  K  A  G  S  E  L  F  F
TCTGCCGTTTCTGTATGGCAGCAACGCCGGGCTGGAGATGACCTGCGGCTTTTACGGCATGCAGGCGCTGCATACCCGCG
  L  P  F  L  Y  G  S  N  A  G  L  E  M  T  C  G  F  Y  G  M  Q  A  L  H  T  R  A
CGCACCTGCTGCAGGCGGTTTATGAAGGCGTGGTATTTAGCCATATGACCCACCTCAGCCGTATGCGCGAACGCTTTACA
  H  L  L  Q  A  V  Y  E  G  V  V  F  S  H  M  T  H  L  S  R  M  R  E  R  F  T
AACGTTCAGGCCCTGCGCGTCACcGGCGGCCCGGCGCACTCCGACGTCTGGATGCAGATGCTGGCGGACGTAAGCGGCTT
  N  V  Q  A  L  R  V  T  G  G  P  A  H  S  D  V  W  M  Q  M  L  A  D  V  S  G  L
```

Fig. 2F

```
ACGCATTGAACTCCCGAAGGTGGAAGAGACcGGCTGTTTTGGCGCGGCCCTCGCCGCTCGtGTcGGtACcGGCGTATACC
  R  I  E  L  P  K  V  E  E  T  G  C  F  G  A  A  L  A  A  R  V  G  T  G  V  Y  R
GCAGcTTTAGCGAAGCCCGGCGCGCCCGGCAGCACCCGGTGCGCACGcTGCTGCCCGATATGACCGCCCACGCGCGCTAT
   S  F  S  E  A  R  R  A  R  Q  H  P  V  R  T  L  L  P  D  M  T  A  H  A  R  Y → yiaQ
cAGCGCAAATACCGCCACtACcTGCATTTGATTGAAGCACTACAGGGCTATCACGCCCGTATTAAGGAGCACGCATTATG
  Q  R  K  Y  R  H  Y  L  H  L  I  E  A  L  Q  G  Y  H  A  R  I  K  E  H  A  L  *
                                                                                  M
AGCCGACCATTACTGCAGCTGGCGcTCGACCATACCAGCCTTCAGGCTGCGCAGCGCGATGTCGCCCTGCTACAGGATCA
  S  R  P  L  L  Q  L  A  L  D  H  T  S  L  Q  A  A  Q  R  D  V  A  L  L  Q  D  H
CGTTGATATTGTGGAGGCGGGAACCATCCTCTGCTTAACCGAAGGGCTTAGCGCGGTTAAAGCCCTGCGCGCCCAGTGTC
   V  D  I  V  E  A  G  T  I  L  C  L  T  E  G  L  S  A  V  K  A  L  R  A  Q  C  P
CGGGGAAGATCATCGTCGCCGACTGGAAAGTCGCCGACGCCGGTGAAACCCTGGCGCAGCAGGCCTTTGGCGCTGGCGCC
   G  K  I  I  V  A  D  W  K  V  A  D  A  G  E  T  L  A  Q  Q  A  F  G  A  G  A
AACTGGATGACCATCATTTGCGCCGCACCGCTCGCCACGGTCGAGAAAGGCCACGCCGTGGCCCAGGCCTGCGGCGGTGA
   N  W  M  T  I  I  C  A  A  P  L  A  T  V  E  K  G  H  A  V  A  Q  A  C  G  G  E
AATTCAGATGGAGCTGTTCGGCAACTGGACGCTGGATGACGCCCGCGCCTGGTACCGTACCGGCGTCCATCAGGCGATTT
   I  Q  M  E  L  F  G  N  W  T  L  D  D  A  R  A  W  Y  R  T  G  V  H  Q  A  I  Y
ACCATCGCGGACGCGATGCCCAGGCCAGCGGGCAGCAGTGGGGGGAGGCGGATCTGGCGCGCATGAAAGCGCTGTCCGAT
   H  R  G  R  D  A  Q  A  S  G  Q  Q  W  G  E  A  D  L  A  R  M  K  A  L  S  D
ATTGGCCTTGAGCTATCGATTACCGGCGGCATTACCCCAGCCGATCTACCGCTGTTCAAAGATATCAACGTCAAAGCCTT
   I  G  L  E  L  S  I  T  G  G  I  T  P  A  D  L  P  L  F  K  D  I  N  V  K  A  F
TATTGCCGGGCGCGCGCTGGCAGGCGCCGCCCATCCGGCGCGGGTTGCCGCCGAATTCCACGCGCAAATCGACGCTATCT
    I  A  G  R  A  L  A  G  A  A  H  P  A  R  V  A  A  E  F  H  A  Q  I  D  A  I
                                  → yiaR
GGGGAGAACAGCATGCGTAACCACCCGTTAGGTATTTATGAAAAAGCGCTGGCGAAGGATCTCAGCTGGCCTGAGCGGCT
    G  E  Q  H  A  *
                      M  R  N  H  P  L  G  I  Y  E  K  A  L  A  K  D  L  S  W  P  E  R  L
GGTACTGGCCAAAAGCTGCGGTTTTGATTTTGTCGAAATGTCGGTGGACGAGACCGATGAACGCCTTTCGCGCCTGGAGT
   V  L  A  K  S  C  G  F  D  F  V  E  M  S  V  D  E  T  D  E  R  L  S  R  L  E  W
```

Fig. 2G

```
GGACCCCGGCCCAGCGCGCATCGCTGGTGAGCGCGATGCTGGAAACCGCGGTCGCCATTCCCTCGATGTGCTTGTCCGCC
   T  P  A  Q  R  A  S  L  V  S  A  M  L  E  T  A  V  A  I  P  S  M  C  L  S  A
CATCGCCGTTTCCCCTTTGGCAGCCGCGATGAAGCGGTACGCGATCGGGCGCGAGAGATTATGACCAAAGCCATCCGCCT
   H  R  R  F  P  F  G  S  R  D  E  A  V  R  D  R  A  R  E  I  M  T  K  A  I  R  L
GGCGCGCGATCTGGGGATCCGCACCATCCAGCTGGCGGGTTACGACGTCTATTACGAAGAGCATGATGAAGGCACCCGGC
  A  R  D  L  G  I  R  T  I  Q  L  A  G  Y  D  V  Y  Y  E  E  H  D  E  G  T  R  Q
AGCGTTTTGCCGAAGGGCTGGCCTGGGCGGTAGAACAGGCCGCCGCCGCGCAGGTAATGCTGGCGGTGGAGATCATGGAC
   R  F  A  E  G  L  A  W  A  V  E  Q  A  A  A  A  Q  V  M  L  A  V  E  I  M  D
ACCGCCTTTATGAACTCCATCAGCAAATGGAAAAAGTGGGACGAGATGCTTTCGTCACCGTGGTTTACCGTCTACCCGGA
   T  A  F  M  N  S  I  S  K  W  K  K  W  D  E  M  L  S  S  P  W  F  T  V  Y  P  D
CGTCGGCAACCTCAGCGCCTGGGGAAACGACGTCACCGCCGAGCTGAAGCTGGGCATCGATCGTATCGCCGCCATCCACC
   V  G  N  L  S  A  W  G  N  D  V  T  A  E  L  K  L  G  I  D  R  I  A  A  I  H  L
TGAAAGATACGCTGCCCGTGACCGACGATAGCCCTGGCCAGTTCCGCGACGTGCCGTTCGgCGAAGGATGCGTCGATTTT
  K  D  T  L  P  V  T  D  D  S  P  G  Q  F  R  D  V  P  F  G  E  G  C  V  D  F
GTCGGCATTTTTAAGACGcTGCGCgAGCTGAACTACGCGGTTCATTTTTGATTGAGATGTGGACGGAGAAAGCCAGCGA
   V  G  I  F  K  T  L  R  E  L  N  Y  R  G  S  F  L  I  E  M  W  T  E  K  A  S  E
                                                                      → yiaS
GCCGGTGCTGGAGATTATCCAGGCCCGGCGCTGGATCGAATCACGGATGCAGGAAGGGGGATTCACATGTTAGAACAACT
  P  V  L  E  I  I  Q  A  R  R  W  I  E  S  R  M  Q  E  G  G  F  T  C  *
                                                                 M  L  E  Q  L
GAAAGCCGAGGTACTGGCGGCAAACCTGGCCCTCCCCGCACACGGCCTGGTCACCTTTTACCTGGGGCAACGTCAGCGCGG
  K  A  E  V  L  A  A  N  L  A  L  P  A  H  G  L  V  T  F  T  W  G  N  V  S  A  V
TCGATGAAACGCGCAAGCTGATGGTCATTAAGCCtTCCGGCGTCGAATATGAGGTGATGACCGCCGACGATATGGTGGTC
   D  E  T  R  K  L  M  V  I  K  P  S  G  V  E  Y  E  V  M  T  A  D  D  M  V  V
GTAGAGATGGCCAGCGGTAAAGTCGTTGAAGGCGGTAAAAAACCCTCTTCAGATACGCCAACGCATCTGGCGCTTTATCG
   V  E  M  A  S  G  K  V  V  E  G  G  K  K  P  S  S  D  T  P  T  H  L  A  L  Y  R
CCGCTATCCGCAGATCGGCGGGATCGTGCATACCCACTCCCGCCACGCGACGATCTGGTCGCAGGCCGGGCTCGATCTCC
   R  Y  P  Q  I  G  G  I  V  H  T  H  S  R  H  A  T  I  W  S  Q  A  G  L  D  L  P
CcGCCTGGGGCACCACCCACGCCGACTACTTCTATGGCGCGATCCCCTGTACCCGACGGATGACCGTTGAGGAGATTAAC
   A  W  G  T  T  H  A  D  Y  F  Y  G  A  I  P  C  T  R  R  M  T  V  E  E  I  N
```

Fig. 2H

```
GGCGAGTATGAGTATCAGACCGGCGAGGTGATTATCAAAACCTTTGAACAGCGCGGCCTGGATCCGGCGCAAATCCCGGC
 G  E  Y  E  Y  Q  T  G  E  V  I  I  K  T  F  E  Q  R  G  L  D  P  A  Q  I  P  A

GGTATTGGTCCATTCACACGGCCCCTTTGCCTGGGGTAAAGACGCCGCCGACGCCGTACATAACGCCGTGGTGCTGGAGG
 V  L  V  H  S  H  G  P  F  A  W  G  K  D  A  A  D  A  V  H  N  A  V  V  L  E  E

AGTGCGCCTACATGGGCCTCTTCTCGCGCCAGTGGCCACAGCTGCCGGATATGCAGTCTGAACTGCTCGATAAACACTAT
 C  A  Y  M  G  L  F  S  R  Q  W  P  Q  L  P  D  M  Q  S  E  L  L  D  K  H  Y  L

CTGCGTAAACACGGCGCGAACGCTATTACGGGCAAAACTAGTCCCGCGGAACTCCCCGGATAAGGCGCTTTGGCCCCCGG
 R  K  H  G  A  N  A  I  T  G  K  T  S  P  A  E  L  P  G

GGGAAGCGTGCAGGATGTTGCTGAACTTTCCCGGAGCGATGCTGCGCATCTGTCCGGGCTACGCGTCCCCGGCGCTCTGC

GGTCAGCACCGCGCCCGGCGGAAAACCCATCAACCCTACGCCGAATTAATATGTCCTTGCAGTAACGACGCTTCCACGCC
GCCGGTCCAGGCTGGTGTGCTTGCGGAAAATCTTGCGAAAATAGCCGACATCGTTAAACCCGCATTTCATCGCCACCTCG
GTAATCGACAGGGAATCGCTGATAAGCAGCTTTTCCGCCGCCCTTACCCGCTGACGGTGCAGCGCTTCGGTAACGTCAGC
CGGAAAGCATGGCGATAAACGGCCCCAGATAACCCGCGTTGCAGTGCAGCTCCT
```

Fig. 2I

| | | | | | |
|---|---|---|---|---|---|
| YiaJ-Ko | MGT-----KE | SENTQDKERP | AGSQSLFRGL | MIEILSNYP | NGCPVAHLSE |
| YiaJ-Ec | MGKEVMGKKE | NEMAQEKERP | AGSQSLFRGL | MIEILSNYP | NGCPIAHLSE |
| YiaJ-Hi | MNIEVK---- | ----MEKEKS | IGNQALIRGL | RLDILSNYP | NGCPIAKLAE |
| YiaJ-Ko | LAGLNKSIVH | RLLQGLQSCG | YVTPAPAAGS | YALTIKFIRV | GQKALSSLNI |
| YiaJ-Ec | LAGLNKSIVH | RLLQGLQSCG | YVTIAPAAGS | YRLTIKFIAV | GQKALSSLNI |
| YiaJ-Hi | LANLNKSIAH | RLLQGLQNEG | YVKPANAAGS | YRLIIKCLSI | GQKVLSSMNI |
| YiaJ-Ko | IHVAAPHLEA | INLATGEIVN | FSSREDDHAI | LIYKLEPTIG | MLRTRAYIGQ |
| YiaJ-Ec | IHIAAPHLEA | INIATGEIIN | FSSREDDHAI | LIYKLEPTIG | MLRTRAYIGQ |
| YiaJ-Hi | IHVASPYLEQ | INLKLGEIIN | FSKREDDHAI | MIYKLEPING | MLKTRAYIGQ |
| YiaJ-Ko | HMR--CIARQ | WAKIYMAFGH | P-DYVESYWN | SHQEIIQFLT | RNTITGLPAM |
| YiaJ-Ec | HMPLYCSAM- | -GKIYMAFGH | P-DYVKSYWE | SHQHEIQFLT | RNTITELPAM |
| YiaJ-Hi | YLKLYCSAM- | -GKIFLAYEK | KVDYLSHYWQ | SHQREIKKLI | RYTITELDDI |
| YiaJ-Ko | HDEIAQIRER | NMAMDREENE | LGVSCIAMFV | FDIHGRVEYA | ISISLSTSRI |
| YiaJ-Ec | FDEIAHIRES | GAAMDREENE | LGVSCIAMFV | FDIHGRVEYA | VSISLSTSRI |
| YiaJ-Hi | KLELETIRQT | AYAMDREENE | LGVICIACPI | FDSFGQVEYA | ISVSMSIYRI |
| YiaJ-Ko | KQVGEKNLIK | PLRDTAFAIS | RELGFSVREG | ----- | |
| YiaJ-Ec | KQVGEKNLIK | PLRETAQAIS | NELGFTVRDD | LGAIT | |
| YiaJ-Hi | NKFGTDAFLQ | EIRKTAEQIS | LELGYEN--- | ----I | |

Fig. 3

| | | | | | |
|---|---|---|---|---|---|
| yiaK-Ko | MKVIFEQLKE | AFNRVLLDAC | VARETADACA | EMFARTIESG | VYSHGVNRFP |
| yiaK-Ec | MKVIFEQLKA | AFNRVLISRG | VDSETADACA | EMFARTIESG | VYSHGVNRFP |
| yiaK-Hi | MRVSYDELKN | EFKRVLLDRQ | LTEELAEECA | TAFIDTIQAG | AYSHGINRFP |
| yiaK-Ko | RFIQQLDNGD | IIPEAQPQRV | TILGAIEQWD | AQRSIGNLTA | KKMMDRAIEL |
| yiaK-Ec | RFIQQLENGD | IIPDAQPKRI | TSLGAIEQWD | AQRSIGNLTA | KKMMDRAIEL |
| yiaK-Hi | RFIQQLEQGD | IVPNAIPTKV | LSLGSIEQWD | AHQAIGNLTA | KKMMDRAIEL |
| yiaK-Ko | ASDHGIGLVA | LRNANHWMRG | GSYGWQAAEK | GYIGICWINS | IAVMAPWGAK |
| yiaK-Ec | AADHGIGLVA | LRNANHWMRG | GSYGWQAAEK | GYIGICWINS | IAVMPPWGAK |
| yiaK-Hi | ASQHGVGVIA | LRNANHWMRG | GSYGWQAAEK | GYIGICWINA | IAVMPPWGAK |
| yiaK-Ko | ECRIGINPLI | VAIPSTPITM | VDMSMSMFSY | GMLEVNRLAG | RELFVDGGFD |
| yiaK-Ec | ECRIGINPLI | VAIPSTPITM | VDMSMSMFSY | GMLEVNRLAG | RQLFVDGGFD |
| yiaK-Hi | ECRIGINPLI | IAVPITPITM | VDMSCSMYSY | GMLEVHRLAG | RQTFVDAGFD |
| yiaK-Ko | DDGRLTKEPG | TIEKNRRILP | MGYWKGSGLS | IVLDMIATLL | SNGSSVAEVT |
| yiaK-Ec | DEGNLTKEPG | VIEKNRRILP | MGYWKGSGMS | IVLDMIATLL | SDGASVAEVT |
| yiaK-Hi | DEGNLTRDPS | IVEKNRRILP | MGFWKGSGLS | IVLDMIATLL | SNGESTVAVT |
| yiaK-Ko | QENSDEYGVS | QIFIAIEVDK | LIDGATRDAK | LQRIMDFITT | AERADENVAV |
| yiaK-Ec | QDNSDEYGIS | QIFIAIEVDK | LIDGPTRDAK | LQRIMDYVTS | AERADENQAI |
| yiaK-Hi | EDKNDEYCVS | QVFIAIEVDR | LIDGKSKDEK | LNRIMDYVKT | AERSDPTQAV |
| yiaK-Ko | RLPGHEFIRL | IDENRRNGIT | VDDSVWAKIQ | AL | |
| yiaK-Ec | RLPGHEFITL | IAENRRNGIT | VDDSVWAKIQ | AL | |
| yiaK-Hi | RLPGHEFITI | LSDNQINGIP | VDERVWAKLK | TL | |

Fig. 4

```
yiaL-Ko  MIFGHIAQPN  -PCRLPAAIE  RALDFLRTID  FHALAPGVVE  IDGQNIFAQV
yiaL-Ec  MIFGHIAQPN  -PCRLPAAIE  KALDFLRATD  FNALEPGVVE  IDGKNIYTQI
yhcH-Hi  MIISSLTNPN  FKVGLPKVIA  EVCDYLNTID  LNALENGRHD  INDQ-IYMNV yiaL-Ko  IDLTIRDAAE  NRPEVHRRYL  DIQFLASGEE  KIGIAIDTGN  NQISESLLEQ
yiaL-Ec  IDLTIREAVV  NRPEVHRRYI  DIQFLAWGEE  KIGIAIDTGN  NKVSESLLEQ
yhcH-Hi  MEPETAEPSS  KKAELHHEYL  DMQVLIRGTE  NIEVGATYPN  ISKYEDYNEA yiaL-Ko  RDIIFYHDSE  HESFFEMIPG  NYAIFFPQDV  HRPGCNKTVA  TP-IRKIVVK
yiaL-Ec  RNIIFYHDSE  HESFIEMIPG  SYAIFFPQDV  HRPGCIMQTA  SE-IRKIVVK
yhcH-Hi  DDYQLCADID  DKFTVIMKPK  MFAMEYPYEP  HKPCCVVNGK  TEKIKKLVVK yiaL-Ko  VAISVL-
yiaL-Ec  VALTALN
yhcH-Hi  VPVK-LI
```

Fig. 5

```
lyxK-Ko  MSKKQAFWLG  IDCGGTYLKA  GLYDAEGHEH  GIVRQALRIM  SPLPGYAERD
lyxK-Ec  MTQ---YWLG  LDCGGSWLKA  GLYDREGREA  GVQRLPLCAL  SPQPGWAERD
lyxK-Hi  MH----YYLG  IDCGGTFIKA  AIFDQNGILQ  SIARRNIPII  SEKPGYAERD lyxK-Ko  MRQLWQHCAA  TIAGLLQQAG  VSGEQIKGVG  ISAQGQGLFL  LDKQDRPLGN
lyxK-Ec  MAELWQCCMA  VIRALLTHSG  VSGEQIVGIG  ISAQGKGLFL  LDKNDKPLGN
lyxK-Hi  MDELWNLCAQ  VIQKTIRQSS  ILPQQIKAIG  ISAQGKGAFF  LDKDNKPLGR lyxK-Ko  AILSSDRRAL  KIVQRWQRDR  IPERLYPVIR  QTLWIGHPAS  LLRWVKENEP
lyxK-Ec  AILSSDRRAM  EIVRRWQEDG  IPEKLYPLIR  QTLWIGHPVS  LLRWLKEHEP
lyxK-Hi  AILSSDQRAY  EIVQCWQKEN  ILQKFYPIIL  QTLWMGHPVS  ILRWIKENEP lyxK-Ko  QRYAQIGCVM  MGHDYLRWCI  TGAKGCEESN  ISESNLYNMA  MGCYDPRLTE
lyxK-Ec  ERYAQIGCVM  MIHDYLRWCI  TGVKGCEESN  ISESNLYNMS  LGEYDPCLTD
lyxK-Hi  SRYEQIHTIL  MSHDYLRFCI  TEKLYCEEIN  ISESNFYNMR  EGKYDIQLAK
```

Fig. 6A

| | | | | | |
|---|---|---|---|---|---|
| lyxK-Ko | WLGIGEIDSA | LPPVVGSAEI | CGEITAQAAA | LIGLAAGIPV | VGGLFDVVST |
| lyxK-Ec | WLGIAEINHA | LPPVVGSAEI | CGEITAQIAA | LIGLKAGIPV | VGGLFDVVST |
| lyxK-Hi | LFGITECIDK | LPPIIKSNKI | AGYVISRAAE | QSGLVEGIPV | VGGLFDVVST |
| lyxK-Ko | ALCAGIEDES | TLNAVMGIWA | VISGIAHGLR | DHEAHPYVYG | RYVNDGQYIV |
| lyxK-Ec | ALCAGIEDEF | TLNAVMGIWA | VISGITRGLR | DGEAHPYVYG | RYVNDGEFIV |
| lyxK-Hi | ALCADLKDDQ | HLNVVLGIWS | VVSGVIHYID | DNQTIPFVYG | KYPEKNKFII |
| lyxK-Ko | HEASPTSSGN | LEWFITAQWGD | LSFDEINQAV | ASLPKAGSEL | FFLPFLYGSN |
| lyxK-Ec | HEASPTSSGN | LEWFITAQWGE | ISFDEINQAV | ASLPKAGGDL | FFLPFLYGSN |
| lyxK-Hi | HEASPTSAGN | LEWFVNQFNL | PNYDDINHEI | AKLKPASSSV | LFAPFLYGSN |
| lyxK-Ko | AGLEMTCGFY | GMQALHIRAH | LLQAVYEGVV | FSHMIHLSRM | RERFINVQAL |
| lyxK-Ec | AGLEMTSGFY | GMQAIHIRAH | LLQAIYEGVV | FSHMIHLNRM | RERFIDVHTL |
| lyxK-Hi | AKLGMQAGFY | GIQSHHIQIH | LLQAIYEGVI | FSIMSHLERM | QVRFPNASTV |
| lyxK-Ko | RVTGGPAHSD | VWMQMLADVS | GLRIIELPKVE | ETGCFGAALA | ARVGTGVYRS |
| lyxK-Ec | RVTGGPAHSD | VWMQMLADVS | GLRIIELPQVE | ETGCFGAALA | ARVGTGVYHN |
| lyxK-Hi | RVTGGPAKSE | VWMQMLADIS | GMRLEIIPNIE | ETGCLGAALM | AMQAESA--- |
| lyxK-Ko | FSEARRARQH | PVRTLLPDMT | AHARYQRKYR | HYLHLIEAIQ | GYHARIKEHA |
| lyxK-Ec | FSEAQRDLRH | PVRTLLPDMT | AHQLYQKKYQ | RYQHLIAALQ | GFHARIKEHT |
| lyxK-Hi | -VEISQIILNI | DRKIFLPDKN | QYSKYQHKYH | RYLKFIEALK | NLD------- |

| | |
|---|---|
| lyxK-Ko | L |
| lyxK-Ec | L |
| lyxK-Hi | - |

Fig. 6B

| | | | | | |
|---|---|---|---|---|---|
| yiaQ-Ko | MSRPLLQIAI | DHTSLQAAQR | DVALLQDHVD | IVEAGTIICL | TEGLSAVKAL |
| yiaQ-Ec | MSRPLLQIAI | DHSSLEAAQR | DVILLKDSVD | IVEAGTIICL | NEGLGAVKAL |
| yiaQ-Hi | MGKPLLQIAI | DAQYLETALV | DVKQIEHNID | IIEVGTIIAC | SEGMRAVRIL |

| | | | | | |
|---|---|---|---|---|---|
| yiaQ-Ko | RAQCPGKIIV | ADWKVADAGE | TLAQQAFGAG | ANWMIIICAA | PLATVEKGHA |
| yiaQ-Ec | REQCPDKIIV | ADWKVADAGE | TLAQQAFGAG | ANWMIIICAA | PLATVEKGHA |
| yiaQ-Hi | RALYPNQIIV | CDLKTTDAGA | TLAKMAFFAG | ADWLIVSAAA | HPAIKAACQK |

| | | | | | |
|---|---|---|---|---|---|
| yiaQ-Ko | VAQA------ | ---CGGEIQM | ELFGNWILDD | ARAWYRIGVH | QAIYHRGRDA |
| yiaQ-Ec | MAQR------ | ---GGGEIQI | ELFGNWILDD | ARDWHRIGVR | QAIYHRGRDA |
| yiaQ-Hi | VAEEFNKIQP | NLGVPKEIQI | ELYGNWNFDE | VKNWLQLGIK | QAIYHRSRDA |

| | | | | | |
|---|---|---|---|---|---|
| yiaQ-Ko | QASGQQWGEA | DLARMKALSD | IGLELSITGG | ITPADILFK | DIN-VKAFIA |
| yiaQ-Ec | QASGQQWGEA | DLARMKALSD | IGLELSITGG | ITPADLPLFK | DIR-VKAFIA |
| yiaQ-Hi | ELSGLSWSNQ | DIENIEKLDS | LGIELSITGG | ITPDDLHLFK | NTKNLKAFIA |

| | | | |
|---|---|---|---|
| yiaQ-Ko | GRALAGAAHP | ARVAAEFHAQ | IDAIWGEQHA |
| yiaQ-Ec | GRALAGAANP | AQVAGDFHAQ | IDAIWGGARA |
| yiaQ-Hi | GRALVGKSGR | -EIAEQLKQK | IGQFW----I |

Fig. 7

| | | | | | |
|---|---|---|---|---|---|
| yiaR-Hi | MR-------- | ---NHPLGIY | EKALAKDLSW | PERIMLAKSC | GFDFVEMSVD |
| yiaR-Ec | MRKSTLSGEV | RVRNHQLGIY | EKALAKDLSW | PERIMLAKSC | GFDFVEMSVD |
| yiaR-Hi | MKK------- | ----HKIGIY | EKALPKNITW | QERISLAKAC | GFFFIEMSID |
| | | | | | |
| yiaR-Hi | ETDERLSRLE | WTPAQRASLV | SAMLETAVAI | PSMCLSAHRR | FPFGSRDEAV |
| yiaR-Ec | ETDERLSRLD | WSAAQRTSLV | AAMIETGVGI | PSMCLSAHRR | FPFGSRDEAV |
| yiaR-Hi | ESNDRLSRIN | WTKSERIALH | QSIIQSGITI | PSMCLSAHRR | FPFGSKDKKI |
| | | | | | |
| yiaR-Hi | RDRAREIMIK | AIRLARDLGI | RTIQLAGYDV | YYEEHDEGIR | QRFAEGLAWA |
| yiaR-Ec | RERAREIMSK | AIRLARDLGI | RTIQLAGYDV | YYEDHDEGIR | QRFAEGLAWA |
| yiaR-Hi | RQKSFEIMEK | AIDLSVNLGI | RTIQLAGYDV | YYEKQDEEII | KYFQEGIEFA |
| | | | | | |
| yiaR-Hi | VEQAAAAQVM | LAVEIMDIAF | MNSISKWKKW | DEMLSSPWFT | VYPDVGNLSA |
| yiaR-Ec | VEQAAASQVM | LAVEIMDIAF | MNSISKWKKW | DEMLASPWFT | VYPDVGNLSA |
| yiaR-Hi | VTLAASAQVT | LAVEIMDIPF | MSSISRWKKW | DTIINSPWFT | VYPDIGNLSA |
| | | | | | |
| yiaR-Hi | WGNDVTAELK | LGIDRIAAIH | LKDTLPVIDD | SPGQFRDVPF | GEGCVDFVGI |
| yiaR-Ec | WGNDVPAELK | LGIDRIAAIH | LKDTQPVIGQ | SPGQFRDVPF | GEGCVDFVGI |
| yiaR-Hi | WNNNIEEELT | LGIDKISAIH | LKDTYPVIET | SKGQFRDVPF | GQGCVDFVHF |
| | | | | | |
| yiaR-Hi | FKILRELNYR | GSFLIEMWTE | KASEPVLEII | QARRWIESRM | QEGGFIC |
| yiaR-Ec | FKILHKLNYR | GSFLIEMWTE | KAKEPVLEII | QARRWIEARM | QEAGFIC |
| yiaR-Hi | FSLLKKLNYR | GAFLIEMWTE | KNEEPILEII | QARKWIVQQM | EKAGLLC |

Fig. 8

| | | | | | |
|---|---|---|---|---|---|
| yiaS-Ko | MIEQLKAEVL | AANLALPAHG | LVTFIWGNVS | AMDETRKLMV | IKPSGVEYEV |
| yiaS-Ec | MIEQLKADVL | AANLALPAHH | LVTFIWGNVS | AMDETRQWMV | IKPSGVEYDV |
| yiaS-Hi | MIAQLKKEVF | EANLALPKHH | LVTFIWGNVS | AIDREKNLVV | IKPSGVDYDV |
| | | | | | |
| yiaS-Ko | MIADDMVVVE | MASGKVVEGG | KKPSSDTPTH | LALYRRYPQI | GGIVHTHSRH |
| yiaS-Ec | MIADDMVVVE | IASGKVVEGS | KKPSSDTPTH | LALYRRYAEI | GGIVHTHSRH |
| yiaS-Hi | MIENDMVVVD | LFIGNIVEGN | KKPSSDTPTH | LELYRQFPHI | GGIVHTHSRH |
| | | | | | |
| yiaS-Ko | ATIWSQAGLD | LPAWGTTHAD | YFYGAIPCTR | RMIVEEINGE | YEYQTGEVII |
| yiaS-Ec | ATIWSQAGLD | LPAWGTTHAD | YFYGAIPCTR | QMIAEEINGE | YEYQTGEVII |
| yiaS-Hi | ATIWAQAGLD | IIEVGTTHGD | YFYGIIPCTR | QMITKEIKGN | YELETGKVIV |
| | | | | | |
| yiaS-Ko | KTFEQRGLDP | AQIPAVLVHS | HGPFAWGKDA | ADAVHNAVVL | EECAYMGLFS |
| yiaS-Ec | ETFEERGRSP | AQIPAVLVHS | HGPFAWGKNA | ADAVHNAVVL | EECAYMGLFS |
| yiaS-Hi | ETFLSRGIEP | DNIPAVLVHS | HGPFAWGKDA | NNAVHNAVVL | EEVAYMNLFS |
| | | | | | |
| yiaS-Ko | RQW-PQLPDM | QSELLDKHYL | RKHGANAITG | KTSPAELPG | |
| yiaS-Ec | RQLAPQLPAM | QNELLDKHYL | RKHGANAYYG | Q-------- | |
| yiaS-Hi | QQLNFYLSPM | QKDLLDKHYL | RKHGQNAYYG | Q-------- | |

Fig. 9

*THE METABOLIC SELECTION STRATEGY*

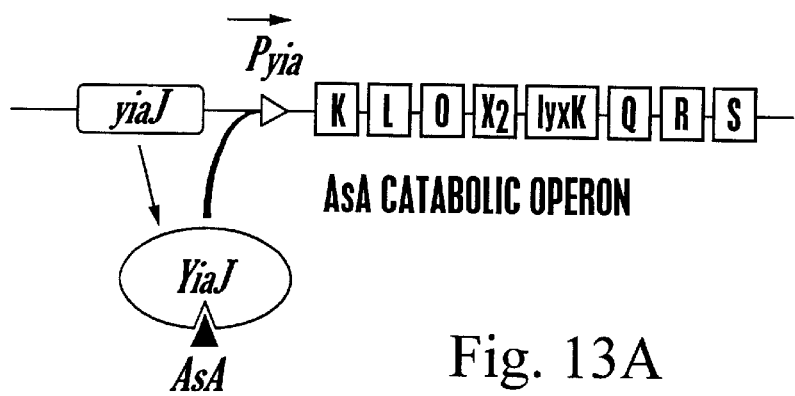
Fig. 13A
Fig. 13B
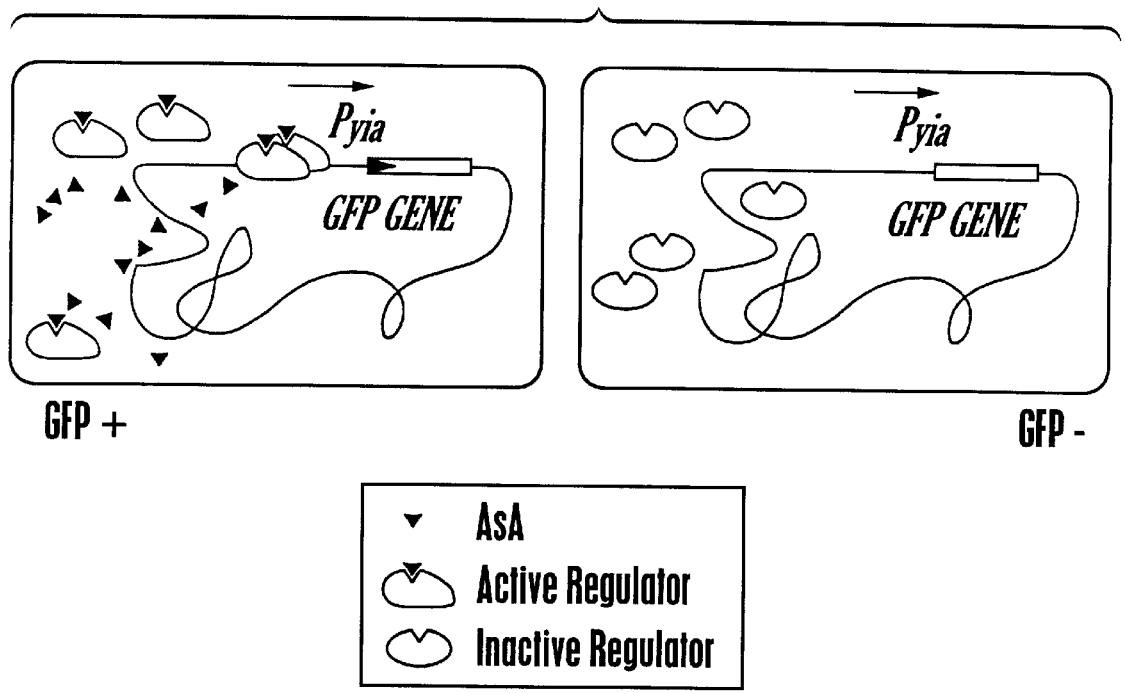

US 6,368,793 B1

METABOLIC SELECTION METHODS

FIELD OF THE INVENTION

The present invention relates to methods for screening for enzymatic pathways, and the isolation of the genes and proteins that make up these pathways.

BACKGROUND OF THE INVENTION

The following description of the background of the invention is provided to aid in understanding the invention, but is not admitted to be, or to describe, prior art to the invention.

Biological synthesis of compounds is frequently more cost effective and more productive than chemical synthesis, which can have low yields, require expensive and toxic reagents, and require lengthy purifications. In contrast, biological synthesis using known pathways can be rapid, with high yields. However, the identification of new biological pathways for syntheses of interest is difficult and time consuming.

Currently, the biochemical screening of isolates is a major means by which people find new pathways for the production of chemicals, antibacterials, and other anti-infectives. However, screening is inherently several orders of magnitude slower than selection and requires that the organism be cultured in the laboratory. Since at least 99% of the microbes in the environment do not grow on laboratory media, less than 1% can be tested using a biochemical screen. Thus, biological pathways in 99% of organisms will never be found by classical biochemical screening technologies.

SUMMARY OF THE INVENTION

The metabolic selection strategy of this invention is designed to find an enzymatic pathway for the conversion of any source compound to any target compound. Conservatively, this technique allows at least a million-fold increase in the discovery rate over classical biochemical screening approaches, and allows testing of the 99% of the environmental microbes that are currently unable to be cultured in the laboratory.

A biocatalytic or metabolic pathway consists of a series of protein catalysts (enzymes) which catalyze the conversion of a starting material to the final product. A general process to identify the metabolic pathway from a source compound to a target compound involves the creation/identification of an easily genetically-manipulatable organism containing an inducible signal, which is activated when a target compound is metabolized. This is followed by the screening of nucleic acid in this organism to identify genes which metabolize the source compound to the target compound.

An example of a selection strategy which can be used to identify the metabolic pathway from a source compound to a target compound is diagrammed in FIG. 11. As a first step, microbial isolates are selected that are capable of metabolizing a target compound "T", but not a source compound "S", to an essential factor. Essential factors can include elements like carbon, sulfur, phosphorous, and nitrogen, or other essential nutrients, e.g. some amino acids, fatty acids, and carbohydrates. In a second step, the pathway responsible for the catabolism of compound "T" is identified and made conditional. That is, the gene(s) for the pathway is cloned and placed under control of an inducible promoter such that growth on the target compound is turned "ON" only when the inducer is present. This engineered strain is referred to as the "tester strain". The third part of the strategy is the transfer of foreign DNA from environmental sources into the tester strain, followed by selection for growth on the source compound "S" in the presence of inducer. Such positive clones either are capable of metabolizing compound "S" in the absence of inducer, in which case utilization of "S" does not require prior conversion to compound "T" (FIG. 11; pathway I), or alternatively metabolize compound "S" only when "T" catabolism is "ON", suggesting that utilization of "S" proceeds via compound "T" to intermediary metabolism (FIG. 11; pathway II). These latter clones are further analyzed and the biocatalysts for the conversion of "S" to "T" are characterized. A specific embodiment of the metabolic selection strategy is shown in FIG. 12, where "S" is 2-keto-L-gulonate (2-KLG), and "T" is ascorbic acid (AsA) which can be metabolized to carbon and energy.

Thus, in a first aspect, the invention features a method of screening for one or more nucleic acid sequences which express a product or products that convert a source compound into a target compound. The method comprises contacting a cell with one or more test nucleic acid sequences, where the cell expresses one or more genes encoding one or more proteins which, in the presence of the target compound, provide a detectable signal. The detectable signal indicates the presence of the desired nucleic acid sequence or sequences.

The term "screening" as used herein refers to methods for identifying a nucleic acid sequence of interest. Preferably, the method permits the identification of a nucleic acid sequence of interest among one or more sequences, more preferably among hundreds (100, 200, . . . 900), most preferably among thousands (1,000, 2,000, . . . etc.) or more. The sequences to be screened can be isolated from one or more organisms. Preferably, the sequences are isolated from hundreds of organisms, more preferably from thousands or more organisms. The term "screening" may include both classical screening, whereby expression of the nucleic acid results in a phenotype that can be identified (for example by having a colony with the nucleic acid of interest change color, fluoresce, or luminesce), and may also include classical selection, where typically the phenotype to be identified is growth on selective media. By "selective" is meant media on which the host strain will not grow or grows poorly, but that strains with the nucleic acid of interest will grow in a manner which can be readily distinguished from host strain growth by methods well-known in the art.

The term "nucleic acid" as used herein refers to either deoxyribonucleic acid or ribonucleic acid that may be isolated, enriched, or purified from natural sources or synthesized recombinantly. These methods are well-known in the art and specific examples are also given herein. Preferably, a "nucleic acid" to be identified in the screening method comprises a nucleic acid encoding a metabolic pathway that is not normally found in the cell. Thus, preferably, the pathway has not simply been inactivated through a mutation and the relevant genes are now being identified through complementation. Rather the nucleic acid being identified does not normally exist in the cell in which it is being screened for. Typically, the screening is cross strains, more typically, cross-species, and even more preferably, cross-genera or with further remoteness.

By "isolated, purified, or enriched" in reference to nucleic acid is meant a polymer of 6 (preferably 21, more preferably 39, most preferably 75) or more nucleotides conjugated to each other, including DNA and RNA that is isolated from a natural source or that is synthesized. In certain embodiments of the invention, longer nucleic acids are preferred, for example those of 300, 600, 900 or more nucleotides and/or those having at least 50%, 60%, 75%, 90%, 95% or 99% identity to the sequence shown in SEQ ID NO:1; SEQ ID NO:2; SEQ ID NO:3; SEQ ID NO:4, SEQ ID NO:5, SEQ ID NO:6, SEQ ID NO:7, SEQ ID NO:8, SEQ ID NO:9, or SEQ ID NO:19.

The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide chain present, but that it is essentially free (about 90–95% pure at least) of non-nucleotide material naturally associated with it, and thus is distinguished from isolated chromosomes.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased. The term "significant" is used to indicate that the level of increase is useful to the person making such an increase, and generally means an increase relative to other nucleic acids of about at least 2-fold, more preferably at least 5- to 10-fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation). Instead, it represents an indication that the sequence is relatively more pure than in the natural environment (compared to the natural level this level should be at least 2–5 fold greater, e.g., in terms of mg/mL). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{6}$-fold purification of the native message. Thus, purification of at least one order of magnitude, preferably two or three orders, and more preferably four or five orders of magnitude is expressly contemplated.

The term "expresses a product" as used herein refers to the production of proteins from a nucleic acid vector containing genes within a cell. The nucleic acid vector is transfected into cells using well known techniques in the art as described herein. The "product" may, or may not, be naturally present in the cell.

The term "nucleic acid vector" relates to a single- or double-stranded circular nucleic acid molecule that can be transfected into cells and replicated within or independently of a cell genome. A circular double-stranded nucleic acid molecule can be cut and thereby linearized upon treatment with restriction enzymes. An assortment of nucleic acid vectors, restriction enzymes, and the knowledge of the nucleotide sequences cut by restriction enzymes are readily available to those skilled in the art. A nucleic acid molecule encoding a desired product can be inserted into a vector by cutting the vector with restriction enzymes and ligating the pieces together, depending on the availability of useful restriction sites. However, there are many methods well-known in the art for the insertion of nucleic acid sequences into vectors.

The term "transfecting" as used herein includes a number of methods to insert a nucleic acid vector or other nucleic acid molecules into a cellular organism. These methods involve a variety of techniques, such as treating the cells with high concentrations of salt, an electric field, detergent, or DMSO to render the outer membrane or wall of the cells permeable to nucleic acid molecules of interest or use of various viral transduction strategies.

The term "converts" as used herein refers to changing one compound into another compound, preferably enzymatically. The "source compound" refers to the compound to be converted to the "target compound." The "target compound" includes not only the compound that is metabolized to form a detectable signal, but can also include intermediates along the path to a detectable signal. This is particularly preferred if the target compound is a surrogate target. By "surrogate target compound" is meant a target that is used because the preferable target cannot be used for any of several potential reasons (e.g. if it doesn't cross membranes, has a short half-life, easily broken down, etc.). The "target compound" also includes interconvertible compounds. By "interconvertible" is meant that a pathway exists in the tester strain to convert the compound to the target compound.

The term "contacting" as used herein refers to mixing a solution comprising the test nucleic acid with a liquid medium bathing the cells of the methods. The solution comprising the nucleic acid may also comprise other components, such as dimethyl sulfoxide (DMSO), which facilitates the uptake of the test nucleic acid into the cells of the methods. This may also be done by other methods well-known in the art including, but not limited to, transfection or transformation techniques. The solution comprising the test nucleic acid may be added to the medium bathing the cells by utilizing a delivery apparatus, such as a pipet-based device or syringe-based device.

The term "cell" as used herein includes the typical definition of a cell, and is further specifically intended to include "cell-free" systems comprising the cellular machinery necessary to express the nucleic acid of the invention. By "cellular machinery" is meant the cellular components present in cell-free transcription and/or translation systems. Such systems are well-known in the art. In particular, the "cell" lacks the ability to convert a source compound into a target compound, prior to the addition of test nucleic acid sequences. The term "lacks the ability" also includes cells in which the activity may be present but is at too low a level to provide a detectable signal, or is low enough that an additional activity is detectably different. By "detectably different" is meant able to be measured over the background level (e.g. the level of the signal endogenously present in the "cell" and in the equipment used to measure the signal) by an amount greater than the level of error present in the method of measuring.

The term "detectable signal" as used herein refers to a method of identification of the nucleic acids of interest e.g. by color, fluorescence, luminescence or growth.

In preferred embodiments of the method for screening nucleic acid that converts a source compound into a target compound, the one or more nucleic acid sequences encodes a metabolic pathway not normally present in said cell. A "metabolic pathway" consists of a series of protein catalysts (enzymes) which catalyze the conversion of a starting material to a product. And further, by "metabolic pathway" is meant the enzymes, and genes that encode them, that metabolize a source compound to a target compound.

In other preferred embodiments, the nucleic acid is selected from the group consisting of mutagenized DNA, environmental DNA, combinatorial libraries, and recombinant DNA. Preferably, the environmental DNA is selected from the group consisting of mud, soil, sewage, flood control channels, sand, and water. Preferably the mutagenized DNA is the result of enzyme mutagenesis where the mutagenesis is selected from the group consisting of random, chemical, PCR-based, and directed mutagenesis. The directed mutagenesis is to include, for example, DNA shuffling. Preferably the enzymes to be mutagenized in this way are selected from the group consisting of lactonases, esterhydrolases, and reductases.

The term "environmental" as used herein refers to nucleic acids extracted from the environment, e.g. from mud, soil, or water. By "extracted" is meant isolated, enriched, or purified as defined above. The environmental sample can be directly extracted without prior laboratory culture, or can be pre-cultured, for example, in the presence of a growth selective agent. Methods are known in the art and examples are described herein.

In still other preferred embodiments of the method for screening nucleic acid that converts a source compound into a target compound, the detectable signal is selected from a group consisting of growth, fluorescence, luminescence, and color. Methods for detecting these signals are well-known in the art. Preferably, the detectable signal is growth, and the target compound provides an element or factor required for growth. Preferably the target compound is selected from the group consisting of ascorbate and 2-keto-L-gulonate (2-KLG), most preferably ascorbate. Preferably the element is selected from the group consisting of carbon, nitrogen, sulfur, and phosphorous. Most preferably, the element is carbon. Alternatively, the essential factor is another essential nutrient. By "required for growth" is meant that the organism does not grow detectably in the absence of the element. By "provides an element" is meant that the compound can be metabolized by the organism, and that the result of this metabolism is the element in some form, e.g. carbon or carbon dioxide.

In other preferred embodiments of the method for screening nucleic acid that converts a source compound into a target compound, the source compound is selected from the group consisting of 2-keto-L-gulonate (2-KLG), 2,5-deoxy-keto-gulonate (2,5-DKG), L-idonate (L-IA), L-gulonate (L-GuA), and glucose, and most preferably 2-KLG.

In still other preferred embodiments of the method for screening nucleic acid that converts a source compound into a target compound, the cell naturally expresses the one or more genes encoding one or more proteins that in the presence of the target compound provide a detectable signal. Alternatively, the cell can be genetically manipulated to express the one or more genes encoding one or more proteins that in the presence of the target compound provide a detectable signal. In both cases, the one or more proteins are preferably Yia operon-related polypeptides. The one or more genes are preferably under the control of an inducible promoter. The inducible promoter preferably comprises the trp-lac hybrid promoter, the lacO operator, and the lac$^q$ repressor.

By "naturally expresses" is meant that the genes encoding the proteins are present in the cell in its natural state, e.g. in nature, prior to culture in the laboratory. The genes may or may not be expressed in the natural state, or may or may not be expressed constitutively or inducibly. By "genetically manipulated to express" is meant the transfection of the desired genes into the cell by methods well-known in the art, examples of which are described herein.

The term "promoter" as used herein, refers to nucleic acid sequence needed for gene sequence expression. Promoter regions vary from organism to organism, but are well known to persons skilled in the art for different organisms. For example, in prokaryotes, the promoter region contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, ribosome binding site, start codon, and the like. By "inducible promoter" is meant a promoter which is only "on" in the presence of an inducer. The "inducer" is typically a small molecule. Inducible promoters and inducers are well-known in the art and examples are given herein.

The term "Yia operon-related polypeptides" as used herein refers to polypeptides comprising 12 (preferably 15, more preferably 20, most preferably 30) or more contiguous amino acids set forth in the full-length amino acid sequence of SEQ ID NO:10; 31 (preferably 35, more preferably 40, most preferably 50) or more contiguous amino acids set forth in the full-length amino acid sequence of SEQ ID NO:11; 5 (preferably 10, more preferably 15, most preferably 25) or more contiguous amino acids set forth in the full-length amino acid sequence of SEQ ID NO:12, SEQ ID NO:13, or SEQ ID NO:14; 17 (preferably 20, more preferably 25, most preferably 35) or more contiguous amino acids set forth in the full-length amino acid sequence of SEQ ID NO:15, SEQ ID NO:17, or SEQ ID NO:18; 11 (preferably 15, more preferably 20, most preferably 30) or more contiguous amino acids set forth in the full-length amino acid sequence of SEQ ID NO:16; or a functional derivative thereof as described herein. In certain aspects, polypeptides of 100, 200, 300 or more amino acids are preferred. The Yia operon-related polypeptide can be encoded by its corresponding full-length nucleic acid sequence or any portion of its corresponding full-length nucleic acid sequence, so long as a functional activity of the polypeptide is retained (see, Examples section). It is well known in the art that due to the degeneracy of the genetic code numerous different nucleic acid sequences can code for the same amino acid sequence. Equally, it is also well known in the art that conservative changes in amino acid can be made to arrive at a protein or polypeptide which retains the functionality of the original.

In both cases, all permutations are within the embodiments of the invention.

The amino acid sequence of the Yia operon-related polypeptide will be substantially similar to the sequence shown in SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18, or fragments thereof. A sequence that is substantially similar to the sequence of SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18 will preferably have at least 90% identity (more preferably at least 95% and most preferably 98–100%) to the sequence of SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18 using a Smith-Waterman protein-protein search.

By "identity" is meant a property of sequences that measures their similarity or relationship. Identity is measured by dividing the number of identical residues by the total number of residues and gaps and multiplying the product by 100. "Gaps" are spaces in an alignment that are the result of additions or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity. For example, the computer algorithm BLAST is preferably used to search for homologous sequences in a database, and CLUSTAL is used to perform alignments. Identity and similarity determinations can be made using a Smith-Waterman protein-protein search, for example.

In still other preferred embodiments of the method for screening nucleic acid that converts a source compound into a target compound, the cell grows on ascorbate and does not grow on 2-KLG. Alternatively, the cell may grow on 2-KLG and not grow on 2,5-DKG. Preferably the cells are bacteria. Most preferably the cell selective for ascorbate is *Kelbsiella oxytoca*. By "grows on" is meant that the cell can utilize the compound (e.g. ascorbate or 2-KLG) as a source of carbon in the minimal essential media. However, the cell is unable to grow in the minimal essential media in the absence of the provided carbon source. Thus, this provides a selective tool for the identification of the nucleic acid encoding the polypeptides of interest.

A second aspect of the invention features an isolated, enriched, or purified nucleic acid molecule encoding one or more Yia operon-related polypeptides selected from the group consisting of YiaJ, YiaK, YiaL, ORF1, YiaX2, LyxK, YiaQ, YiaR, and YiaS.

In preferred embodiments, the isolated, enriched, or purified nucleic acid molecule encoding one or more Yia operon-related polypeptides comprises a nucleotide sequence that: (a) encodes a polypeptide having the full length amino acid sequence set forth in SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18; (b) is the complement of the nucleotide sequence of (a); and (c) hybridizes under highly stringent conditions to the nucleotide molecule of (a) and encodes a naturally occurring polypeptide.

In another preferred embodiment, the invention features an isolated, enriched, or purified nucleic acid molecule, wherein said nucleic acid molecule comprises the nucleotide sequence set forth in SEQ ID NO:19. The nucleic acid molecule comprises: (a) one or more nucleotide sequences that are set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9; (b) the complement of the nucleotide sequence of (a); (c) nucleic acid that hybridizes under stringent conditions to the nucleotide molecule of (a); (d) the full length sequence of SEQ ID NO:19, except that it lacks one or more of the sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9; or (e) is the complement of the nucleotide sequence of (d).

The term "complement" refers to two nucleotides that can form multiple thermodynamically favorable interactions with one another. For example, adenine is complementary to thymine as they can form two hydrogen bonds. Similarly, guanine and cytosine are complementary since they can form three hydrogen bonds. A nucleotide sequence is the complement of another nucleotide sequence if the nucleotides of the first sequence are complementary to the nucleotides of the second sequence. The percent of complementarity (i.e. how many nucleotides from one strand form multiple thermodynamically favorable interactions with the other strand compared with the total number of nucleotides present in the sequence) indicates the extent of complementarity of two sequences.

Various low or high stringency hybridization conditions may be used depending upon the specificity and selectivity desired. These conditions are well-known to those skilled in the art. Under stringent hybridization conditions only highly complementary nucleic acid sequences hybridize. Preferably, such conditions prevent hybridization of nucleic acids having 1 or 2 mismatches out of 20 contiguous nucleotides.

By "stringent hybridization conditions" is meant hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C.

In other preferred embodiments the isolated, enriched, or purified nucleic acid molecule encoding one or more Yia operon-related polypeptides further comprises a vector or promoter effective to initiate transcription in a host cell. Preferably, the vector or promoter comprises the trp-lac hybrid promoter, the lacO operator, and the $lacI^q$ repressor gene. In still other preferred embodiments, the nucleic acid molecule is isolated, enriched, or purified from a bacteria, preferably *Kelbsiella oxytoca*.

The invention also features recombinant nucleic acid, preferably in a cell or an organism. The recombinant nucleic acid may contain a sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9, or a functional derivative thereof, and a vector or a promoter effective to initiate transcription in a host cell. The recombinant nucleic acid can alternatively contain a transcriptional initiation region functional in a cell, a sequence complementary to an RNA sequence encoding one or more Yia operon-related polypeptides and a transcriptional termination region functional in a cell.

In preferred embodiments, the isolated, enriched, purified, recombinant, or recombinant in a cell, nucleic acid comprises, consists essentially of, or consists of the full-length nucleic acid sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9, encodes the full-length amino acid sequence of SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18, a functional derivative thereof, or at least 35, 40, 45, 50, 60, 75, 100, 200, or 300 contiguous amino acids of SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. The Yia operon-related polypeptides comprise, consist essentially of, or consist of at least 35, 40, 45, 50, 60, 75, 100, 200, or 300 contiguous amino acids of SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. The nucleic acid may be isolated from a natural source by cDNA cloning or by subtractive hybridization. The natural source may be prokaryotic, eukaryotic, or protozoal, preferably bacterial, from the environment, and the nucleic acid may be synthesized by the triester method or by using an automated DNA synthesizer. In other preferred embodiments, the nucleic acid molecule is isolated, enriched, or purified from a bacteria, preferably *Klebsiella oxytoca*.

In yet other preferred embodiments, the nucleic acid is a conserved or unique region, for example those useful for: the design of hybridization probes to facilitate identification and cloning of additional polypeptides, the design of PCR probes to facilitate cloning of additional polypeptides, obtaining antibodies to polypeptide regions, and designing antisense oligonucleotides.

By "conserved nucleic acid regions", are meant regions present on two or more nucleic acids encoding a Yia operon-related polypeptide, to which a particular nucleic acid sequence can hybridize under lower stringency conditions. Examples of lower stringency conditions are provided in Abe, et al. (J. Biol. Chem. 19:13361–13368, 1992), hereby incorporated by reference herein in its entirety, including any drawings, figures, or tables. Preferably, conserved regions differ by no more than 5 out of 20 nucleotides.

By "unique nucleic acid region" is meant a sequence present in a nucleic acid coding for a Yia operon-related polypeptide that is not present in a sequence coding for any other naturally occurring polypeptide. Such regions preferably encode 12 (preferably 15, more preferably 20, most preferably 30) or more contiguous amino acids set forth in the full-length amino acid sequence of SEQ ID NO:10; 30 (preferably 35, more preferably 40, most preferably 50) or more contiguous amino acids set forth in the full-length amino acid sequence of SEQ ID NO:11; 5 (preferably 10, more preferably 15, most preferably 25) or more contiguous amino acids set forth in the full-length amino acid sequence of SEQ ID NO:12, SEQ ID NO:13, or SEQ ID NO:14; 17 (preferably 20, more preferably 25, most preferably 35) or more contiguous amino acids set forth in the full-length amino acid sequence of SEQ ID NO:15, SEQ ID NO:17, or SEQ ID NO:18; 11 (preferably 15, more preferably 20, most preferably 30) or more contiguous amino acids set forth in the full-length amino acid sequence of SEQ ID NO:16. In particular, a unique nucleic acid region is preferably of bacterial origin.

A third aspect of the invention features a nucleic acid probe for the detection of nucleic acid encoding one or more Yia operon-related polypeptides, selected from the group consisting of YiaJ, YiaK, YiaL, ORF1, YiaX2, LyxK, YiaQ, YiaR, and YiaS, in a sample. Preferably, the nucleic acid probe encodes a polypeptide that is a fragment of the protein encoded by the full length amino acid sequence set forth in SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. The nucleic acid probe contains a nucleotide base sequence that will hybridize to the full-length sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9, or a functional derivative thereof. Hybridization is preferably under stringent conditions.

In preferred embodiments, the nucleic acid probe hybridizes to nucleic acid encoding at least 12, 32, 75, 90, 105, 120, 150, 200, 250, 300 or 350 contiguous amino acids set forth in the full-length amino acid sequence of SEQ ID NO:10; at least 30, 75, 90, 105, 120, 150, 200, 250, 300 or 350 contiguous amino acids set forth in the full-length amino acid sequence of SEQ ID NO:11; at least 5, 12, 32, 75, 90, 105, 120, 150, 200, 250, 300 or 350 contiguous amino acids set forth in the full-length amino acid sequence of SEQ ID NO:12, SEQ ID NO:13, or SEQ ID NO:14; at least 17, 32, 75, 90, 105, 120, 150, 200, 250, 300 or 350 contiguous amino acids set forth in the full-length amino acid sequence of SEQ ID NO:15, SEQ ID NO:17, or SEQ ID NO:18; at least 11, 32, 75, 90, 105, 120, 150, 200, 250, 300 or 350 contiguous amino acids set forth in the full-length amino acid sequence of SEQ ID NO:16, or a functional derivative thereof.

Methods for using the probes include detecting the presence or amount of Yia operon-related RNA in a sample by contacting the sample with a nucleic acid probe under conditions such that hybridization occurs and detecting the presence or amount of the probe bound to Yia operon-related RNA. The nucleic acid duplex formed between the probe and a nucleic acid sequence coding for a Yia operon-related polypeptide may be used in the identification of the sequence of the nucleic acid detected (Nelson et al., in Non-isotopic DNA Probe Techniques, Academic Press, San Diego, Kricka, ed., p. 275, 1992, hereby incorporated by reference herein in its entirety, including any drawings, figures, or tables). Kits for performing such methods may be constructed to include a container means having disposed therein a nucleic acid probe.

A fourth aspect of the invention features a recombinant cell comprising a nucleic acid molecule encoding one or more Yia operon-related polypeptides selected from the group consisting of YiaJ, YiaK, YiaL, ORF1, YiaX2, LyxK, YiaQ, YiaR, and YiaS. In such cells, the nucleic acid may be under the control of the genomic regulatory elements, or, preferably, may be under the control of exogenous regulatory elements including an exogenous promoter. By "exogenous" is meant a promoter that is not normally coupled in vivo transcriptionally to the coding sequence for the Yia operon-related polypeptides.

In preferred embodiments, the recombinant cell comprises nucleic acid encoding a polypeptide that is a fragment of the protein encoded by the amino acid sequence set forth in SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. By "fragment," is meant an amino acid sequence present in a Yia operon polypeptide. Preferably, such a sequence comprises at least 12, 32, 75, 90, 105, 120, 150, 200, 250, 300 or 350 contiguous amino acids set forth in the full-length amino acid sequence of SEQ ID NO:10; at least 30, 75, 90, 105, 120, 150, 200, 250, 300 or 350 contiguous amino acids set forth in the full-length amino acid sequence of SEQ ID NO:11; at least 5, 12, 32, 75, 90, 105, 120, 150, 200, 250, 300 or 350 contiguous amino acids set forth in the full-length amino acid sequence of SEQ ID NO:12, SEQ ID NO:13, or SEQ ID NO:14; at least 17, 32, 75, 90, 105, 120, 150, 200, 250, 300 or 350 contiguous amino acids set forth in the full-length amino acid sequence of SEQ ID NO:15, SEQ ID NO:17, or SEQ ID NO:18; at least 11, 32, 75, 90, 105, 120, 150, 200, 250, 300 or 350 contiguous amino acids set forth in the full-length amino acid sequence of SEQ ID NO:16.

Alternatively, the recombinant cell comprises the nucleic acid sequence set forth in SEQ ID NO:19, or comprises: (a) one or more nucleotide sequences that are set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9; (b) the complement of the nucleotide sequence of (a); (c) nucleic acid that hybridizes under stringent conditions to the nucleotide molecule of (a); (d) the full length sequence of SEQ ID NO:19, except that it lacks one or more of the sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9; and (e) is the complement of the nucleotide sequence of (d). Preferably, the recombinant cell further comprises a vector or promoter effective to initiate transcription of the above-identified nucleic acid in the cell. Preferably, the vector or promoter comprises the trp-lac hybrid promoter, the lacO operator, and the lacI$^q$ repressor gene. Preferably, the recombinant cell is a bacteria, more preferably *Klebsiella oxytoca*.

Other preferred embodiments of this aspect of the invention include a recombinant cell useful for screening for one or more nucleic acid sequences that express one or more products that convert a source compound into a target compound, where the cell expresses one or more genes, comprising an inducible promoter, and where the one or more genes encodes one or more proteins that in the presence of the target compound and an inducer provide a detectable signal, where the detectable signal indicates the presence of the one or more nucleic acid sequences. Preferably, the detectable signal is selected from a group consisting of growth, fluorescence, luminescence, and color, and most preferably is growth.

In preferred embodiments, of the recombinant cell useful for screening, the one or more nucleic acid sequences encodes a metabolic pathway not normally present in said cell. In other preferred embodiments, the nucleic acid is selected from the group consisting of mutagenized DNA, environmental DNA, combinatorial libraries, and recombinant DNA. Preferably, the environmental DNA is selected from the group consisting of mud, soil, sewage, flood control channels, sand, and water. Preferably the mutagenized DNA is the result of enzyme mutagenesis where the mutagenesis is selected from the group consisting of random, chemical, PCR-based, and directed mutagenesis. The directed mutagenesis is to include, for example, DNA shuffling. Preferably the enzymes to be mutagenized in this way are selected from the group consisting of lactonases, esterhydrolases, and reductases.

Additionally in this preferred embodiment, the cell preferably requires the presence of the target compound and the inducer for growth. Preferably, the target compound is selected from the group consisting of ascorbate and 2-KLG. In addition, the one or more genes are preferably under the control of an inducible promoter, preferably comprising the trp-lac hybrid promoter, the lacO operator, and the lacI$^q$ repressor gene. Preferably, the one or more proteins encoded by the one or more genes are one or more Yia operon-related polypeptides. Preferably, the cell naturally expresses the one or more genes, or has been genetically manipulated to express the one or more genes. Preferably, the cell is a bacteria, most preferably *Kelbsiella oxytoca*.

A fifth aspect of the invention features one or more isolated, enriched, or purified Yia operon-related polypeptides selected from the group consisting of YiaJ, YiaK, YiaL, ORF1, YiaX2, LyxK, YiaQ, YiaR, and YiaS.

By "isolated" in reference to a polypeptide is meant a polymer of 6 (preferably 12, more preferably 18, most preferably 25, 32, 40, or 50) or more amino acids conjugated to each other, including polypeptides that are isolated from a natural source or that are synthesized. In certain aspects longer polypeptides are preferred, such as those with 100, 200, 300, 400, or more contiguous amino acids of the sequence set forth in SEQ ID NO:10, SEQ ID NO:11, SEQ ID NO:12, SEQ ID NO:13, SEQ ID NO:14, SEQ ID NO:15, SEQ ID NO:16, SEQ ID NO:17 or SEQ ID NO:18.

The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of no-amino acid-based material naturally associated with it.

By the use of the term "enriched" in reference to a polypeptide is meant that the specific amino acid sequence constitutes a significantly higher fraction (2–5 fold) of the total amino acid sequences present in the cells or solution of interest than in normal or diseased cells or in the cells from which the sequence was taken. This could be caused by a person by preferential reduction in the amount of other amino acid sequences present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acid sequences of about at least 2-fold, more preferably at least 5- to 10-fold or even more. The term also does not imply that there is no amino acid sequence from other sources. The other source of amino acid sequences may, for example, comprise amino acid sequence encoded by a yeast or bacterial genome, or a cloning vector such as pUC19. The term is meant to cover only those situations in which man has intervened to increase the proportion of the desired amino acid sequence.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment. Compared to the natural level this level should be at least 2–5 fold greater (e.g., in terms of mg/mL). Purification of at least one order of magnitude, preferably two or three orders, and more preferably four or five orders of magnitude is expressly contemplated. The substance is preferably free of substances present in its natural environment at a functionally significant level, for example 90%, 95, or 99% pure.

In preferred embodiments, the polypeptide is a fragment of the protein encoded by the full length amino acid sequence set forth in SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. Preferably, the Yia operon polypeptide contains at least 12, 32, 75, 90, 105, 120, 150, 200, 250, 300 or 350 contiguous amino acids set forth in the full-length amino acid sequence of SEQ ID NO:10; at least 30, 75, 90, 105, 120, 150, 200, 250, 300 or 350 contiguous amino acids set forth in the full-length amino acid sequence of SEQ ID NO:11; at least 5, 12, 32, 75, 90, 105, 120, 150, 200, 250, 300 or 350 contiguous amino acids set forth in the full-length amino acid sequence of SEQ ID NO:12, SEQ ID NO:13, or SEQ ID NO:14; at least 17, 32, 75, 90, 105, 120, 150, 200, 250, 300 or 350 contiguous amino acids set forth in the full-length amino acid sequence of SEQ ID NO:15, SEQ ID NO:17, or SEQ ID NO:18; at least 11, 32, 75, 90, 105, 120, 150, 200, 250, 300 or 350 contiguous amino acids set forth in the full-length amino acid sequence of SEQ ID NO:16, or a functional derivative thereof.

The polypeptide can be isolated from a natural source by methods well-known in the art. The natural source may be protozoal, eukaryotic, or prokaryotic, and the polypeptide may be synthesized using an automated polypeptide synthesizer. Preferably, the polypeptide is isolated, enriched, or purified from bacteria, most preferably *Kelbsiella oxytoca*.

In some embodiments the invention includes one or more recombinant Yia operon-related polypeptides. By "recombinant Yia operon-related polypeptide" is meant a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

In a sixth aspect, the invention features an antibody (e.g., a monoclonal or polyclonal antibody) having specific binding affinity to a Yia operon-related polypeptide or a Yia operon-related polypeptide fragment. In preferred embodiments, the yia operon-related polypeptide is selected from the group consisting of YiaJ, YiaK, YiaL, ORF1, YiaX2, LyxK, YiaQ, YiaR, and YiaS.

By "specific binding affinity" is meant that the antibody binds to the target Yia operon-related polypeptide with greater affinity than it binds to other polypeptides under specified conditions. Antibodies or antibody fragments are polypeptides which contain regions that can bind other polypeptides. The term "specific binding affinity" describes an antibody that binds to a Yia operon polypeptide with greater affinity than it binds to other polypeptides under specified conditions.

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art (Kohler et al., Nature 256:495–497, 1975, and U.S. Pat. No. 4,376,110, both of which are hereby incorporated by reference herein in their entirety including any figures, tables, or drawings).

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

Antibodies or antibody fragments having specific binding affinity to a Yia operon-related polypeptide of the invention may be used in methods for detecting the presence and/or amount of Yia operon polypeptide in a sample by probing the sample with the antibody under conditions suitable for Yia operon-related-antibody immunocomplex formation and detecting the presence and/or amount of the antibody conjugated to the Yia operon-related polypeptide. Diagnostic kits for performing such methods may be constructed to include antibodies or antibody fragments specific for the Yia operon-related polypeptide as well as a conjugate of a binding partner of the antibodies or the antibodies themselves.

An antibody or antibody fragment with specific binding affinity to a Yia operon-related polypeptide of the invention can be isolated, enriched, or purified from a prokaryotic or eukaryotic organism. Routine methods known to those skilled in the art enable production of antibodies or antibody fragments, in both prokaryotic and eukaryotic organisms. Purification, enrichment, and isolation of antibodies, which are polypeptide molecules, are described above.

Antibodies having specific binding affinity to a Yia operon-related polypeptide of the invention may be used in methods for detecting the presence and/or amount of Yia operon-related polypeptide in a sample by contacting the sample with the antibody under conditions such that an immunocomplex forms and detecting the presence and/or amount of the antibody conjugated to the Yia operon-related polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

In a seventh aspect, the invention features a hybridoma that produces an antibody having specific binding affinity to a Yia operon-related polypeptide or a Yia operon-related polypeptide fragment. By "hybridoma" is meant an immortalized cell line that is capable of secreting an antibody, for example an antibody to a Yia operon-related polypeptide of the invention In preferred embodiments, the antibody to the Yia operon-related polypeptide comprises a sequence of amino acids that is able to specifically bind a Yia operon-related polypeptide of the invention.

In an eighth aspect, the invention features a Yia operon-related polypeptide binding agent able to bind to a Yia operon-related polypeptide. The binding agent is preferably a purified antibody that recognizes an epitope present on a Yia operon-related polypeptide of the invention. Other binding agents include molecules that bind to Yia operon-related polypeptides and analogous molecules which bind to a Yia operon-related polypeptide. Such binding agents may be identified by using assays that measure Yia operon-related binding partner activity, such as those that measure growth or ascorbate metabolism.

The invention also features a method for screening for other organisms containing a Yia operon-related polypeptide of the invention or an equivalent sequence. The method involves identifying the novel polypeptide in other organisms using techniques that are routine and standard in the art, such as those described herein for identifying the Yia operon-related polypeptide of the invention or others standard in the art (e.g., cloning, Southern or Northern blot analysis, in situ hybridization, PCR amplification, etc.).

A ninth aspect of the invention features a method for identifying a substance that converts a source compound to a target compound, comprising: contacting a cell with nucleic acid, where the nucleic acid expresses a product that converts a source compound into a target compound, and where the cell expresses one or more proteins which in the presence of the target compound provide a detectable signal; contacting the cell with a test substance; and monitoring the detectable signal, where the detectable signal indicates the presence of the substance.

In preferred embodiments of the method for identifying a substance that converts a source compound to a target compound, the substance is selected from the group consisting of antibodies, small organic molecules, peptidomimetics, and natural products. In other preferred embodiments, the detectable signal is selected from a group consisting of growth, fluorescence, luminescence, and color. Preferably, the detectable signal is growth, and the target compound is metabolizable to an element selected from the group consisting of carbon, nitrogen, sulfur, and phosphorous, most preferably carbon. Alternatively, the target compound is metabolizable to an essential nutrient. In still other preferred embodiments of the invention, the source compound is selected from the group consisting of 2-KLG, 2,5-DKG, L-IA, L-GuA, and glucose.

In other highly preferred embodiments of the method for identifying a substance that converts a source compound to a target compound, the one or more proteins are one or more Yia operon-related polypeptides. Preferably, the Yia operon further comprises a vector or promoter effective to initiate transcription in a host cell, and most preferably the vector or promoter comprises the trp-lac hybrid promoter, the lacO operator, and the lacI$^q$ repressor gene.

A tenth aspect of the invention features a method for detecting the presence, absence, or amount of a compound in a sample comprising: contacting the sample with a cell, where the cell expresses one or more genes encoding one or more proteins that in the presence of the compound provide a detectable signal that indicates the presence, absence, or amount of said compound. A schematic of an example of a preferred embodiment of the method is shown in FIG. 13. In preferred embodiments, the compound is ascorbate and the detectable signal is selected from a group consisting of growth, fluorescence, luminescence, and color. In other preferred embodiments, the one or more genes comprises yiaJ, and preferably further comprises a promoter transcriptionally linked to a reporter gene. Preferably, YiaJ is naturally expressed in the cell, or the cell has been genetically manipulated to express YiaJ. Preferably the reporter gene has a promoter transcriptionally linked and the expression of the reporter gene is regulated by the binding of YiaJ to the promoter. The binding of YiaJ to the promoter is preferably regulated by the presence or absence of ascorbate. Preferably the cell is a bacteria, and most preferably *Kelbsiella oxytoca*.

An eleventh aspect of the invention features an isolated, purified, or enriched nucleic acid molecule encoding YiaJ and a reporter gene. Preferably, the nucleic acid molecule further comprises a promoter transcriptionally linked to a reporter gene. Preferably the reporter gene is regulated by the binding of YiaJ to the promoter. The binding of YiaJ to the promoter is preferably regulated by the presence or absence of ascorbate. In preferred embodiments, the nucleic acid molecule further comprises a vector or promoter effective to initiate transcription in a host cell.

A twelfth aspect of the invention features a recombinant cell comprising the nucleic acid molecule described in the eleventh aspect of the invention, above.

Preferred embodiments of this aspect of the invention feature a recombinant cell for detecting the presence, absence, or amount of a compound in a sample, where the cell expresses one or more genes encoding one or more proteins that in the presence of the compound provide a detectable signal, where the signal indicates the presence, absence, or amount of the compound. In preferred embodiments, the detectable signal is selected from a group consisting of growth, fluorescence, luminescence, and color.

In other preferred embodiments of the recombinant cell for detecting the presence, absence, or amount of a compound in a sample, the one or more genes comprises yiaJ, and further comprises a promoter transcriptionally linked to a reporter gene. Preferably, the expression of the reporter gene is regulated by the binding of YiaJ to the promoter. Preferably, yiaJ is naturally expressed in the recombinant cell, or the cell has been genetically manipulated to express yiaJ. The recombinant cell is preferably a bacteria, and more preferably *Kelbsiella oxytoca*.

A thirteenth aspect of the invention features a method of selection for one or more nucleic acid sequences encoding a metabolic pathway from a source compound to a target compound comprising: (1) identifying an organism that metabolizes a target compound to provide an essential element; (2) identifying one or more genes responsible for the metabolism of the target compound to the essential element; (3) expressing the one or more genes under the control of an inducible promoter, whereby the target compound is metabolized only in the presence of an inducer and not in the absence of the inducer; (4) expressing nucleic acid sequences potentially encoding the metabolic pathway in the recipient organism; and (5) selecting the recipient organism for growth in the presence of the source compound in the absence of the target compound and in the presence of the inducer, where growth on the source compound in the absence of the target compound and in the presence of the inducer indicates the presence of the nucleic acid sequence.

In preferred embodiments of the method of selection, the essential element is selected from the group consisting of carbon, phosphorous, nitrogen, and sulfur, and most preferably is carbon.

In other preferred embodiments, the method of selection further comprises the transfer of the one or more genes to a highly genetically manipulatable recipient organism, such that the recipient organism metabolizes the target compound to provide an essential element.

By a "highly genetically manipulatable recipient organism" is meant an organism, preferably single-celled, more preferably bacteria, and most preferably *Klebsiella oxytoca*, that can be manipulated by the standard genetic techniques, including but not limited to, transfection, selection in selective media, growth in culture.

The summary of the invention described above is not limiting and other features and advantages of the invention will be apparent from the following detailed description of the invention, and from the claims.

DESCRIPTION OF THE FIGURES

FIGS. 2A–2I show the nucleic acid sequence (SEQ ID NO:19) and translated amino acid sequences of the open reading frames of the yia operon and its putative regulator, yiaJ.

FIG. 3 shows a multiple sequence alignment of YiaJ-Ko (SEQ ID NO:10), YiaJ-Ec (SEQ ID NO:20), and YiaJ-Hi (SEQ ID NO:21). Identical sequences among the three proteins are indicated by shading.

FIG. 4 shows a multiple sequence alignment of YiaK-Ko (SEQ ID NO:11), YiaK-Ec (SEQ ID NO:22), and YiaK-Hi (SEQ ID NO:23). Identical sequences among the three proteins are indicated by shading.

FIG. 5 shows a multiple sequence alignment of YiaJ-Ko (SEQ ID NO:12), YiaL-Ec (SEQ ID NO:24), and YhcH-Hi (SEQ ID NO:25). Identical sequences among the three proteins are indicated by shading.

FIGS. 6A and 6B show a multiple sequence alignment of LyxK-Ko (SEQ ID NO:15), LyxK-Ec (SEQ ID NO:26), and LyxK-Hi (SEQ ID NO:27). Identical sequences among the three proteins are indicated by shading.

FIG. 7 shows a multiple sequence alignment of YiaQ-Ko (SEQ ID NO:16), YiaQ-Ec (SEQ ID NO: 28), and YiaQ-Hi (SEQ ID NO:29). Identical sequences among the three proteins are indicated by shading.

FIG. 8 shows a multiple sequence alignment of YiaR-Ko (SEQ ID NO:17), YiaR-Ec (SEQ ID NO:30), and YiaR-Hi (SEQ ID NO:31). Identical sequences among the three proteins are indicated by shading.

FIG. 9 shows a multiple sequence alignment of YiaS-Ko (SEQ ID NO:18), YiaS-Ec (SEQ ID NO:32), and YiaS-Hi (SEQ ID NO:33). Identical sequences among the three proteins are indicated by shading.

FIG. 13, part A shows a theoretical model for AsA-dependent activation of the yiaK-S operon. Based on transcriptional analyses, the YiaJ regulatory protein is thought to activate transcription of the yiaK-S AsA catabolic operon in response to AsA present in the medium. However, the inventors do not wish to be held to this interpretation of the data.

FIG. 13, part B shows a schematic representation of a whole-cell reporter system for AsA sensing. The yiaK-S promoter region ($P_{yia}$) is fused to the Green-Fluorescent-Protein (GFP) gene (or to lux or other reporter genes), and the fusion is integrated into the chromosome of an indicator strain, which also contains the YiaJ regulator. In the presence of AsA, YiaJ is stimulated and activates transcription of the yia-GFP fusion, thereby conferring an easily detectable GFP-positive or fluorescent phenotype.

DETAILED DESCRIPTION OF THE INVENTION

The instant invention is based in part on the use of a metabolic selection strategy that uses a recombinant DNA selection procedure to identify enzymatic pathways for the conversion of a source compound to a target compound. This technique allows at least a million-fold increase in the discovery rate over classical biochemical screening approaches, and allows testing of the 99% of the environmental microbes that are currently not able to be cultured in the laboratory.

Figure 11:
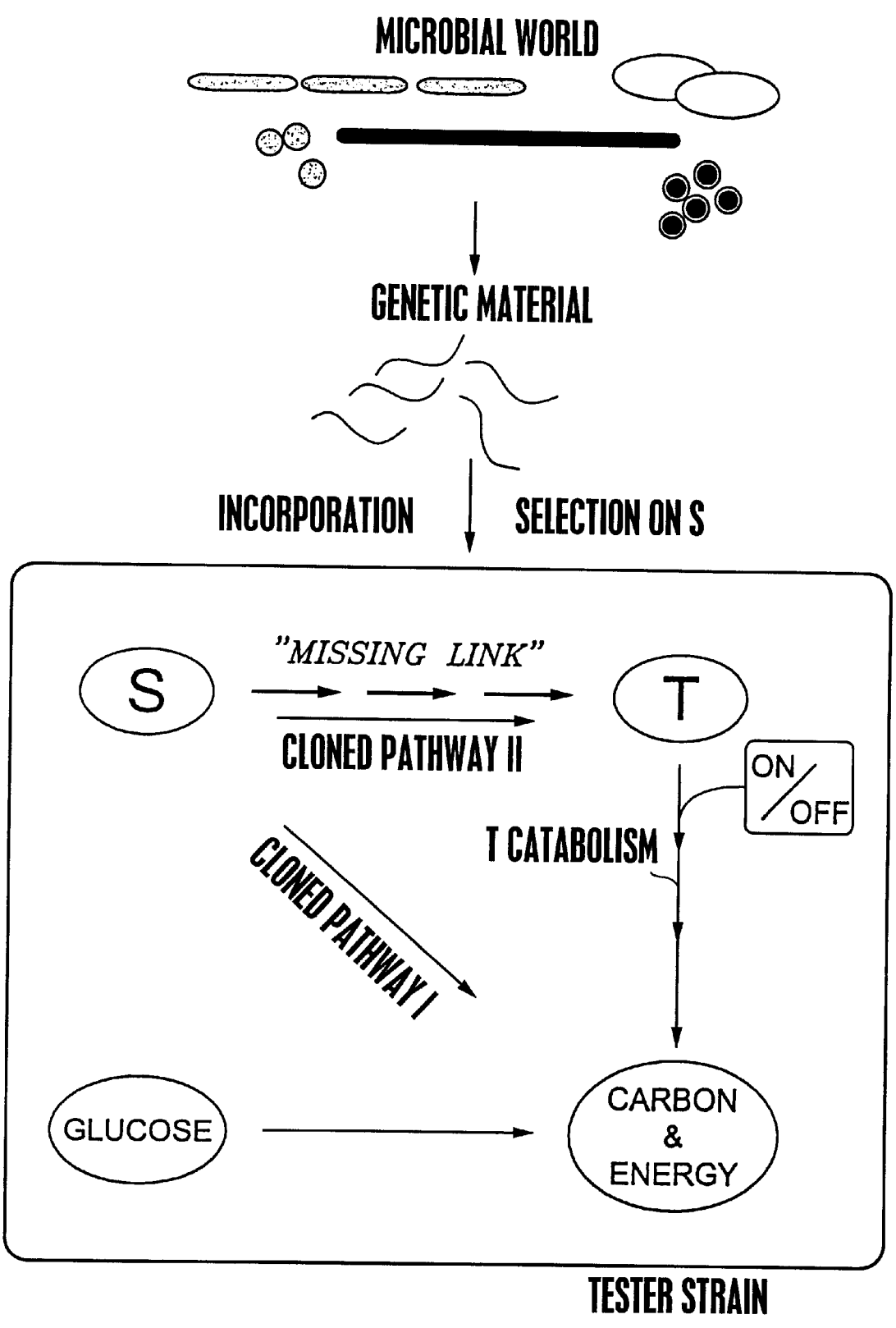
FIG. 11 shows a schematic representation of a general example of a metabolic selection process. Briefly, genetic material, isolated from microbes, is incorporated into a Tester Strain and the gene(s) of interest selected for by growth on "S". The gene(s) of interest will catalyze the conversion of "S" to "T" in the Tester Strain, thereby allowing growth on "S".

The general process involves the creation/identification of an easily genetically-manipulatable organism containing an inducible signal, such that the signal is activated when a target compound is metabolized, followed by the screening of nucleic acid in this organism to identify genes which metabolize a source compound to the target compound (FIGS. 11 and 12) In a specific embodiment, the process involves three steps (1) the identification of an organism capable of metabolizing the target compound to carbon and energy, and the transfer of this metabolic pathway to a highly genetically manipulatable organism, e.g. *Escherichia coli* or *Bacillus subtilis*, with the result that the recipient now uses the target compound for growth; (2) placing the expression of the pathway under the control of an inducible promoter, whereby the target compound is metabolized in the presence of an inducer and not in its absence; and (3) cloning genes, which are to be tested for their ability to metabolize the source compound, into the recipient, and selecting for growth on the source compound in the presence of the inducer but in the absence of the target compound.

Once positive organisms are identified in the above selection scheme by growth in the presence of inducer, the organisms are further screened for their ability to grow in the absence of the inducer. No growth in the absence of the inducer indicates that the metabolism of the source compound proceeds via the target compound. Thus, the nucleic acid probably encodes an enzymatic pathway for the conversion of the source compound to the target compound.

Growth in the absence of the inducer indicates that metabolism of the source compound to the essential element or factor does not require prior conversion to the target compound, rather it may proceed directly, or through an intermediate, to the essential element or factor. When conversion directly to the target compound is the desired result, further work is necessary to obtain the desired genes. methods of obtaining the desired genes include: re-selection of DNA from other sources; random mutation of the DNA followed by re-selection; knocking out (deleting or blocking the expression of genes by methods well-known in the art) the genes that allow the direct conversion to the essential element or factor or from an intermediate to the essential element or factor followed by re-selection; etc. In one preferred embodiment, expression of the genes that allow the direct, or partially direct, conversion to the essential factor are knocked out or their expression blocked, thereby "forcing" the conversion to the essential element through the target compound. This will be effective if a pathway through the target compound existed, but was thermodynamically unfavorable, for example.

Alternatively, if the intermediate is freely interconvertible with the desired target compound as well as to the essential element, growth in the absence of the inducer may be an acceptable outcome, or even desirable. By "freely interconvertable" is meant that an enzymatic pathway is present to allow the intermediate to be converted to the target. The interconvertability of the compounds would also be determined using the methods described above for obtaining a pathway directly to the target compound.

Under some circumstances, selection of a pathway directly, or through an intermediate, to the essential element or factor rather than to the target compound, is a preferred result. For example, under circumstances where the desired target compound is not one that can be used for direct selection (e.g. does not cross membranes or is rapidly broken down) a "surrogate target" might have to be used. A surrogate target refers to one that is used for selection, but is not the most highly desired target. In this embodiment, the target would preferably be on the pathway of conversion of the surrogate target to the essential element.

I. Functional Derivatives

Provided herein are functional derivatives of a polypeptide or nucleic acid of the invention. By "functional derivative" is meant a "chemical derivative," "fragment," or "variant," of the polypeptide or nucleic acid of the invention, which terms are defined below. A functional derivative retains at least a portion of the function of the protein, for example reactivity with an antibody specific for the protein, enzymatic activity or binding activity mediated through noncatalytic domains, which permits its utility in accordance with the present invention. It is well known in the art that due to the degeneracy of the genetic code numerous different nucleic acid sequences can code for the same amino acid sequence. Equally, it is also well known in the art that conservative changes in amino acid can be made to arrive at a protein or polypeptide which retains the functionality of the original. In both cases, all permutations are intended to be covered by this disclosure.

Also included with "functional derivatives" of the polypeptides, in particular, of the invention are "chemical derivatives". A "chemical derivative" contains additional chemical moieties not normally a part of the protein. Covalent modifications of the protein or peptides are included within the scope of this invention. Such modifications may be introduced into the molecule by reacting targeted amino acid residues of the peptide with an organic derivatizing agent that is capable of reacting with selected side chains or terminal residues, for example, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing primary amine containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimide (R'—N═C═N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking the component peptides of the protein to each other or to other proteins in a complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[p-azidophenyl) dithiolpropioimidate yield photo-activatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W.H. Freeman & Co., San Francisco, pp. 79–86 (1983)), acetylation of the N-terminal amine, and, in some instances, amidation of the C-terminal carboxyl groups.

Such derivatized moieties may improve the stability, solubility, absorption, biological half-life, and the like. The moieties may alternatively eliminate or attenuate any undesirable side effect of the protein complex and the like. Moieties capable of mediating such effects are disclosed, for example, in Remington's Pharmaceutical Sciences, 18th ed., Mack Publishing Co., Easton, Pa. (1990).

The term "fragment" is used to indicate a polypeptide derived from the amino acid sequence of the proteins, of the complexes having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence. Fragments of a protein are useful for screening for compounds that act to modulate enzyme activity, as described herein. It is understood that such fragments may retain one or more characterizing portions of the native complex. Examples of such retained characteristics include: catalytic activity; substrate specificity; interaction with other molecules in the intact cell; regulatory functions; or binding with an antibody specific for the native complex, or an epitope thereof.

Another functional derivative intended to be within the scope of the present invention is a "variant" polypeptide which either lacks one or more amino acids or contains additional or substituted amino acids relative to the native polypeptide. The variant may be derived from a naturally occurring complex component by appropriately modifying the protein DNA coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native protein, as described above.

A functional derivative of a protein with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, DNA 2:183) wherein nucleotides in the DNA coding the sequence are modified, and thereafter expressing this recombinant DNA in a prokaryotic or eukaryotic host cell, using techniques such as those described above. Alternatively, proteins with amino acid deletions, insertions and/or substitutions may be conveniently prepared by direct chemical synthesis, using methods well-known in the art. The functional derivatives of the proteins typically exhibit the same qualitative biological activity as the native proteins.

II. Nucleic Acid Probes, Methods, and Kits for Detection of Yia Operon-related Polypeptides A nucleic acid probe of the present invention may be used to probe an appropriate chromosomal or cDNA library by usual hybridization methods to obtain other nucleic acid molecules of the present invention. A chromosomal DNA or cDNA library may be prepared from appropriate cells according to recognized methods in the art (cf. "Molecular Cloning: A Laboratory Manual", second edition, Cold Spring Harbor Laboratory, Sambrook, Fritsch, & Maniatis, eds., 1989).

In the alternative, chemical synthesis can be carried out in order to obtain nucleic acid probes having nucleotide sequences which correspond to N-terminal and C-terminal portions of the amino acid sequence of the polypeptide of interest. The synthesized nucleic acid probes may be used as primers in a polymerase chain reaction (PCR) carried out in accordance with recognized PCR techniques, essentially according to PCR Protocols, "A Guide to Methods and Applications", Academic Press, Michael, et al., eds., 1990, utilizing the appropriate chromosomal or cDNA library to obtain the fragment of the present invention.

One skilled in the art can readily design such probes based on the sequence disclosed herein using methods of computer alignment and sequence analysis known in the art ("Molecular Cloning: A Laboratory Manual", 1989, supra). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

One method of detecting the presence of nucleic acids of the invention in a sample comprises (a) contacting said sample with the above-described nucleic acid probe under conditions such that hybridization occurs, and (b) detecting the presence of said probe bound to said nucleic acid molecule. One skilled in the art would select the nucleic acid probe according to techniques known in the art as described above. Samples to be tested include but should not be limited to RNA samples extracted from environmental samples.

A kit for detecting the presence of nucleic acids of the invention in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horseradish peroxidase, alkaline phosphatase), and affinity labeled probes (biotin, avidin, or steptavidin). Preferably, the kit further comprises instructions for use.

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

III. DNA Constructs Comprising Yia Operon-Related Nucleic Acid Molecules and Cells Containing These Constructs The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecule. The present invention also relates to a nucleic acid molecule comprising a transcriptional region functional in a cell, a sequence complementary to an RNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule and thereby is capable of expressing a polypeptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding a Yia operon polypeptide of the invention may be obtained by the above-described methods. This region may be retained for its transcriptional termination regulatory sequences, such as termination and polyadenylation. Thus, by retaining the 3'-region naturally contiguous to the DNA sequence encoding a polypeptide of the invention, the transcriptional termination signals may be provided. Where the transcriptional termination signals are not satisfactorily functional in the expression host cell, then a 3' region functional in the host cell may be substituted.

Two DNA sequences (such as a promoter region sequence and a sequence encoding a polypeptide of the invention) are said to be operably linked if the nature of the linkage between the two DNA sequences does not (1) result in the introduction of a frame-shift mutation, (2) interfere with the ability of the promoter region sequence to direct the transcription of a gene sequence encoding a polypeptide of the invention, or (3) interfere with the ability of the gene sequence of a polypeptide of the invention to be transcribed by the promoter region sequence. Thus, a promoter region would be operably linked to a DNA sequence if the promoter were capable of effecting transcription of that DNA sequence. Thus, to express a gene encoding a polypeptide of the invention, transcriptional and translational signals recognized by an appropriate host are necessary.

The present invention encompasses the expression of a gene encoding a polypeptide of the invention (or a functional derivative thereof) in either prokaryotic or eukaryotic cells. Prokaryotic hosts are, generally, very efficient and convenient for the production of recombinant proteins and are, therefore, one type of preferred expression system for polypeptides of the invention. Prokaryotes most frequently are represented by various strains of $E.\ coli$. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC18, pUC19 and the like; suitable phage or bacteriophage vectors may include ygt10, ygt11 and the like; and suitable virus vectors may include pMAM-neo, pKRC and the like. Preferably, the selected vector of the present invention has the capacity to replicate in the selected host cell.

Recognized prokaryotic hosts include bacteria such as $E.\ coli$, Bacillus, Streptomyces, Pseudomonas, Salmonella, Serratia, Klebsiella, and the like. The prokaryotic host must be compatible with the replicon and control sequences in the expression plasmid.

To express a polypeptide of the invention (or a functional derivative thereof) in a prokaryotic cell, it is necessary to operably link the sequence encoding the polypeptide of the invention to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the cat promoter of the chloramphenicol acetyl transferase gene sequence of pPR325, and the like. Examples of inducible prokaryotic promoters include the major right and left promoters of bacteriophage λ ($P_L$ and $P_R$), the trp, recA, λacZ, λacI, and gal promoters of $E.\ coli$, the α-amylase (Ulmanen et al., J. Bacteriol. 162:176–182, 1985) and the ζ-28-specific promoters of $B.\ subtilis$ (Gilman et al., Gene Sequence 32:11–20, 1984), the promoters of the bacteriophages of Bacillus (Gryczan, In: The Molecular Biology of the Bacilli, Academic Press, Inc., NY, 1982), and Streptomyces promoters (Ward et al., Mol. Gen. Genet.

203:468–478, 1986). Prokaryotic promoters are reviewed by Glick (Ind. Microbiot. 1:277–282, 1987), Cenatiempo (Biochimie 68:505–516, 1986), and Gottesman (Ann. Rev. Genet. 18:415–442, 1984).

Proper expression in a prokaryotic cell also requires the presence of a ribosome-binding site upstream of the gene sequence-encoding sequence. Such ribosome-binding sites are disclosed, for example, by Gold et al. (Ann. Rev. Microbiol. 35:365–404, 1981). The selection of control sequences, expression vectors, transformation methods, and the like, are dependent on the type of host cell used to express the gene. As used herein, "cell", "cell line", and "cell culture" may be used interchangeably and all such designations include progeny. Thus, the terms "transformants" or "transformed cells" include the primary subject cell and cultures derived therefrom, without regard to the number of transfers. It is also understood that all progeny may not be precisely identical in DNA content, due to deliberate or inadvertent mutations. However, as long as mutant progeny have the same functionality as that of the originally transformed cell, they are considered to be the same cell or cell-line.

Host cells which may be used in the expression systems of the present invention are not strictly limited, provided that they are suitable for use in the expression of the polypeptide of interest. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

A nucleic acid molecule encoding a polypeptide of the invention and an operably linked promoter may be introduced into a recipient prokaryotic or eukaryotic cell either as a nonreplicating DNA or RNA molecule, which may either be a linear molecule or a closed covalent circular molecule. Alternatively, permanent expression may occur through the integration of the introduced DNA sequence into the host chromosome or as a circular plasmid.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of mRNA. These elements may include splice signals, as well as transcription promoters, enhancers, and termination signals. cDNA expression vectors incorporating such elements include those described by Okayama (Mol. Cell. Biol. 3:280–289, 1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in $E.$ $coli$ (such as, for example, pBR322, ColEl, pSC101, pACYC 184, πVX; "Molecular Cloning: A Laboratory Manual", 1989, supra). Bacillus plasmids include pC194, pC221, pT127, and the like (Gryczan, In: The Molecular Biology of the Bacilli, Academic Press, NY, pp. 307–329, 1982). Suitable Streptomyces plasmids include p1J101 (Kendall et al., J. Bacteriol. 169:4177–4183, 1987), and streptomyces bacteriophages such as φC31 (Chater et al., In: Sixth International Symposium on Actinomycetales Biology, Akademiai Kaido, Budapest, Hungary, pp. 45–54, 1986). Pseudomonas plasmids are reviewed by John et al. (Rev. Infect. Dis. 8:693–704, 1986), and Izaki (Jpn. J. Bacteriol. 33:729–742, 1978).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene(s) results in the production of a polypeptide of the invention, or fragments thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

V. Antibodies, Hybridomas, Methods of Use and Kits for Detection of Yia Operon-Related Polypeptides The present invention relates to an antibody having binding affinity to a polypeptide of the invention. The polypeptide may have the amino acid sequence set forth in SEQ ID NO:10, SEQ ID NO:11, SEQ ID NO:12, SEQ ID NO:13, SEQ ID NO:14, SEQ ID NO:10, SEQ ID NO:16, SEQ ID NO:17, SEQ ID NO:18, or a functional derivative thereof, or at least 6 contiguous amino acids thereof (preferably, at least 15, 20, 25, 30, 35, or 40 contiguous amino acids thereof).

The present invention also relates to an antibody having specific binding affinity to a polypeptide of the invention. Such an antibody may be isolated by comparing its binding affinity to a polypeptide of the invention with its binding affinity to other polypeptides. Those which bind selectively to a polypeptide of the invention would be chosen for use in methods requiring a distinction between a polypeptide of the invention and other polypeptides. Such methods could include, but should not be limited to, the identification of other cells expressing the polypeptides of the invention.

The polypeptides of the present invention can be used in a variety of procedures and methods, such as for the generation of antibodies, for use in identifying pharmaceutical compositions, and for selection of other enzymmatic pathways.

The polypeptides of the present invention can be used to produce antibodies or hybridomas. One skilled in the art will recognize that if an antibody is desired, such a peptide could be generated as described herein and used as an immunogen.

The antibodies of the present invention include monoclonal and polyclonal antibodies, as well fragments of these antibodies.

The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands, 1984; St.

Groth et al., J. Immunol. Methods 35:1–21, 1980). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity.

Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Agl4 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124, 1988). Hybridomas secreting the desired antibodies are cloned and the class and subclass are determined using procedures known in the art (Campbell, "Monoclonal Antibody Technology: Laboratory Techniques in Biochemistry and Molecular Biology", supra, 1984).

For polyclonal antibodies, antibody-containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see Stemberger et al., J. Histochem. Cytochem. 18:315, 1970; Bayer et al., Meth. Enzym. 62:308-, 1979; Engval et al., Immunol. 109:129-, 1972; Goding, J. Immunol. Meth. 13:215-, 1976. The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10, 1986; Jacoby et al., Meth. Enzym. 34, Academic Press, N.Y., 1974). The immobilized antibodies of the present invention can be used for in vitro, in vivo, and in situ assays as well as immuno-chromatography.

Furthermore, one skilled in the art can readily adapt currently available procedures, as well as the techniques, methods and kits disclosed herein with regard to antibodies, to generate peptides capable of binding to a specific peptide sequence in order to generate rationally designed antipeptide peptides (Hurby et al., "Application of Synthetic Peptides: Antisense Peptides", In Synthetic Peptides, A User's Guide, W.H. Freeman, NY, pp. 289–307, 1992; Kaspczak et al., Biochemistry 28:9230–9238, 1989).

Anti-peptide peptides can be generated by replacing the basic amino acid residues found in the peptide sequences of the Yia operon polypeptides of the invention with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

The present invention also encompasses a method of detecting a Yia operon-related polypeptide in a sample, comprising: (a) contacting the sample with an above-described antibody, under conditions such that immunocomplexes form, and (b) detecting the presence of said antibody bound to the polypeptide. In detail, the methods comprise incubating a test sample with one or more of the antibodies of the present invention and assaying whether the antibody binds to the test sample. Detection of a polypeptide of the invention in a sample may indicate the presence of the pathway of the invention in other cells.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion-based Ouchterlony, or rocket immunofluorescent assays) can readily be adapted to employ the antibodies of the present invention. Examples of such assays can be found in Chard ("An Introduction to Radioimmunoassay and Related Techniques" Elsevier Science Publishers, Amsterdam, The Netherlands, 1986), Bullock et al. ("Techniques in Immunocytochemistry," Academic Press, Orlando, FL Vol. 1, 1982; Vol. 2, 1983; Vol. 3, 1985), Tijssen ("Practice and Theory of Enzyme Immunoassays: Laboratory Techniques in Biochemistry and Molecular Biology," Elsevier Science Publishers, Amsterdam, The Netherlands, 1985).

The immunological assay test samples of the present invention include cells, protein or membrane extracts of cells, or environmental samples. The test samples used in the above-described method will vary based on the assay format, nature of the detection method and the tissues, cells or extracts used as the sample to be assayed. Methods for preparing protein extracts or membrane extracts of cells are well known in the art and can readily be adapted in order to obtain a sample which is testable with the system utilized.

A kit contains all the necessary reagents to carry out the previously described methods of detection. The kit may comprise: (i) a first container means containing an above-described antibody, and (ii) second container means containing a conjugate comprising a binding partner of the antibody and a label. Preferably, the kit also contains instructions for use. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

Other methods associated with the invention are described in the examples disclosed herein.

EXAMPLES

The examples below are not limiting and are merely representative of various aspects and features of the present invention. The examples below demonstrate the construction and use of metabolic selection systems, and the isolation of desired enzymatic pathways.

Example 1

Construction of a Tester Strain for the Selection of Pathways from 2-KLG to AsA

This example is exemplary of how to construct tester strains, and therefore can be applied to the identification and construction of tester strains for the selection of other metabolic pathways. The basic idea is to take environmental samples and test them for growth on a target compound (in the example, ascorbate). Then, positive colonies are screened for the inability to grow on the source compound (in the example, 2-KLG). The tester strain is the one that grows on the target, but not the source compound. Once the genes encoding the metabolic pathway for the target compound to the essential factor (an element such as carbon, nitrogen, sulphur or phosphorous, or a nutrient, for example) are identified, they are then place under the control of an inducible promoter, and the tester strain is ready to be utilized to select for the metabolic pathway from the source to the target compound.

If it proves difficult to obtain a tester strain that grows on the target, but not the source, but strains exist that do not grow on the source, then the pathway that permits growth on the target can be isolated and transferred to another strain that doesn't grow on the source in order to obtain the desired tester strain.

Isolation of a Strain that Grows on AsA, but not 2-KLG

Samples from diverse natural environments were collected to use for the isolation of microbes that can utilize ascorbic acid (AsA) as the sole carbon source. No bacterial species has previously been reported to grow on AsA minimal medium.

Environmental samples were collected from freshwater lakes, lemon and orange orchards, residential backyard soils, human and animal solid wastes.

Over 100 microbial isolates, capable of forming visible colonies within 20 hours of incubation at 30° C. on M9 minimal medium containing 0.5% AsA, were selected from these samples. These 100 isolates were then screened for their ability to grow on 2-Keto-L-Gulonate (2-KLG) minimal medium.

One of the isolates that could utilize AsA as its sole source of carbon and energy, but could not grow on 2-KLG, was identified as *Kelbsiella oxytoca* (Table 1). Thus, *Kelbsiella oxytoca* was retained as a candidate for genetic engineering of a host strain that can use AsA under controlled conditions for the selection of cloned microbial pathways from 2-KLG to AsA.

Other bacterial strains capable of metabolizing ascorbic acid to carbon and energy were also identified, as were some that also metabolized 2KLG to carbon and energy (Table 1).

TABLE 1

| COMPOUND UTILIZATION OF ENVIRONMENTAL ISOLATES | | |
|---|---|---|
| | AsA | 2-KLG |
| GRAM POSITIVES | 72 HR | 24 HR |
| *Bacillus megaterium* | + | + |
| Streptomyces species | ++ | ++ |
| Yellow Bug | ++ | +++ |
| GRAM NEGATIVES | 24 HR | 72 HR |
| *Klebsiella pneumoniae* | +++ | − |
| Klebsiella species | +++ | − |
| *Klebsielia oxytoca* | +++ | − |
| Unknown Malodorous Short Rod | ++ | − |

Identification of Genes Responsible for AsA Catabolism

In order to identify the gene(s) responsible for AsA catabolism in *K. oxytoca*, mutagenesis by transposition insertion was performed in *K. oxytoca* strain VJSK009 (Cali, B. M., et al., 1989. J. Bacteriol. 171:2666–2672) using the pfd-Tn5 delivery vector as described by Metzger, M., et al., 1992. Nucl. Acids Res. 20:2265–2270. Among 5,000 clones screened, several mutants that were no longer capable of growing on AsA were identified, most of which were also affected in their ability to grow on conventional carbon sources such as glucose, maltose, pyruvate or succinate. Two of the mutants, however, were specifically affected in AsA utilization and were further characterized by cloning and sequencing the regions adjacent to the transposon insertion.

Characterization of the Genes/Proteins of the Operon

In both mutants, the Tn5 insertion was found to disrupt the same operon of 8 genes. This operon was found to be homologous to the yiaK-S operon of *E. coli* (Blattner, F. R., et al., 1997. Science 277:1453–1462) which is thought to be involved with carbohydrate utilization (Badia, J., et al., 1998. J. Biol. Chem. 273:8376–8381).

Figure 1:
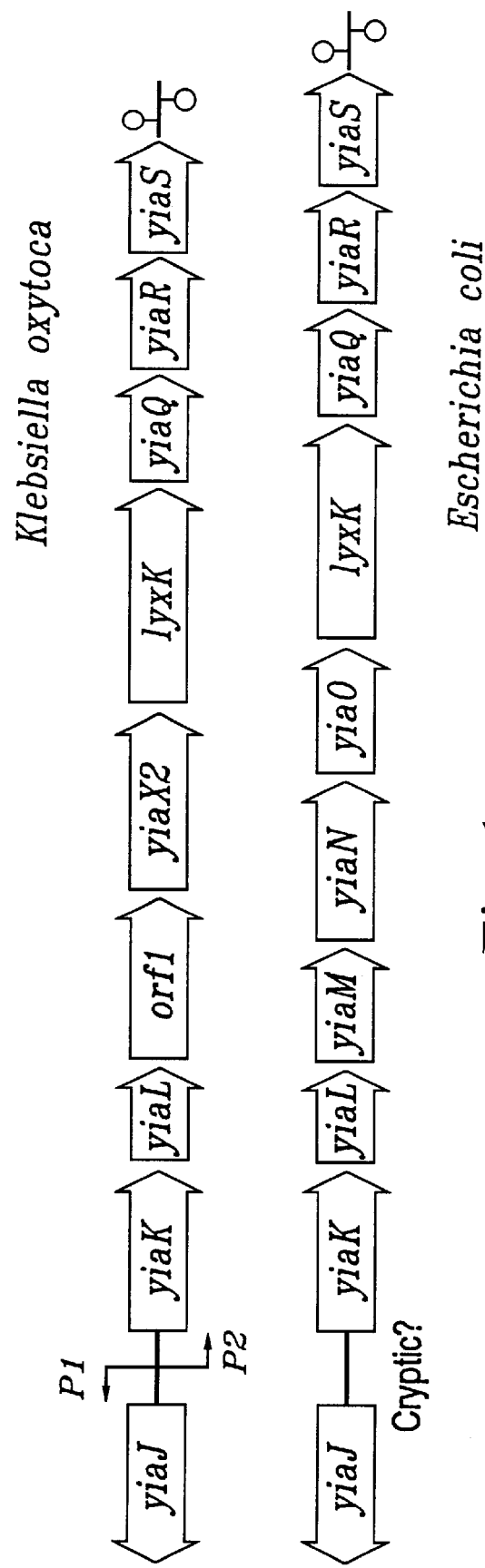
FIG. 1 shows a physical map of the yiaK-S operon, which includes the open reading frames yiaK, yiaL, orf1, yiaX2, lyxK, yiaQ, yiaR, and yia, and its putative regulator, yiaJ, compared with the *E. coli* yiaK-S operon, which includes the open reading frames yiaK, yiaL, yiaM, yiaN, yiaO, lyxK, yiaQ, yiaR, and yiaS, and its putative regulator yiaJ.

Similarly to *E. coli*, the *K. oxytoca* yiaK-S operon is preceded by a transcriptional regulator, yiaJ. A physical map of the yiaK-S operon and its putative regulator is shown in FIG. 1. The nucleic acid sequence and translated amino acid sequence of the open reading frames of the operon and its putative regulator are shown in FIGS. 2 A–I.

The functions of the yia operon gene products in *K. oxytoca* and *E. coli* are unknown, except for the *E. coli* lyxK-encoded enzyme which was shown to phosphorylate L-xylulose and play a key role in the utilization of L-lyxose by *E. coli* (Sanchez, J. C., et al., 1994. J. Biol. Chem. 169:29665–29669). However, the yiaK-S operon is thought to be silent in wild-type *E. coli*, L-xylulose activity could not be detected in wild type cells, and *E. coli* K12 is unable to metabolize L-lyxose (Sanchez, J. C., et al., 1994. supra). A similar operon is also present in *Haemophilus influenzae*, but no function has been determined for any of the open reading frames (Fleischmann, R. D., et al., 1995. Science 269:496–512).

Alignments of the yia open reading frames common among the three species are shown (FIGS. 3–9). Based on sequence similarities, yiaQ has been classified as a putative hexulose-6-phosphate synthase, yiaR as a putative hexulose-6-phosphate isomerase, and yiaS as a putative sugar isomerase (data not shown).

Place Operon Under the Control of an Inducible Promoter

Figure 10:
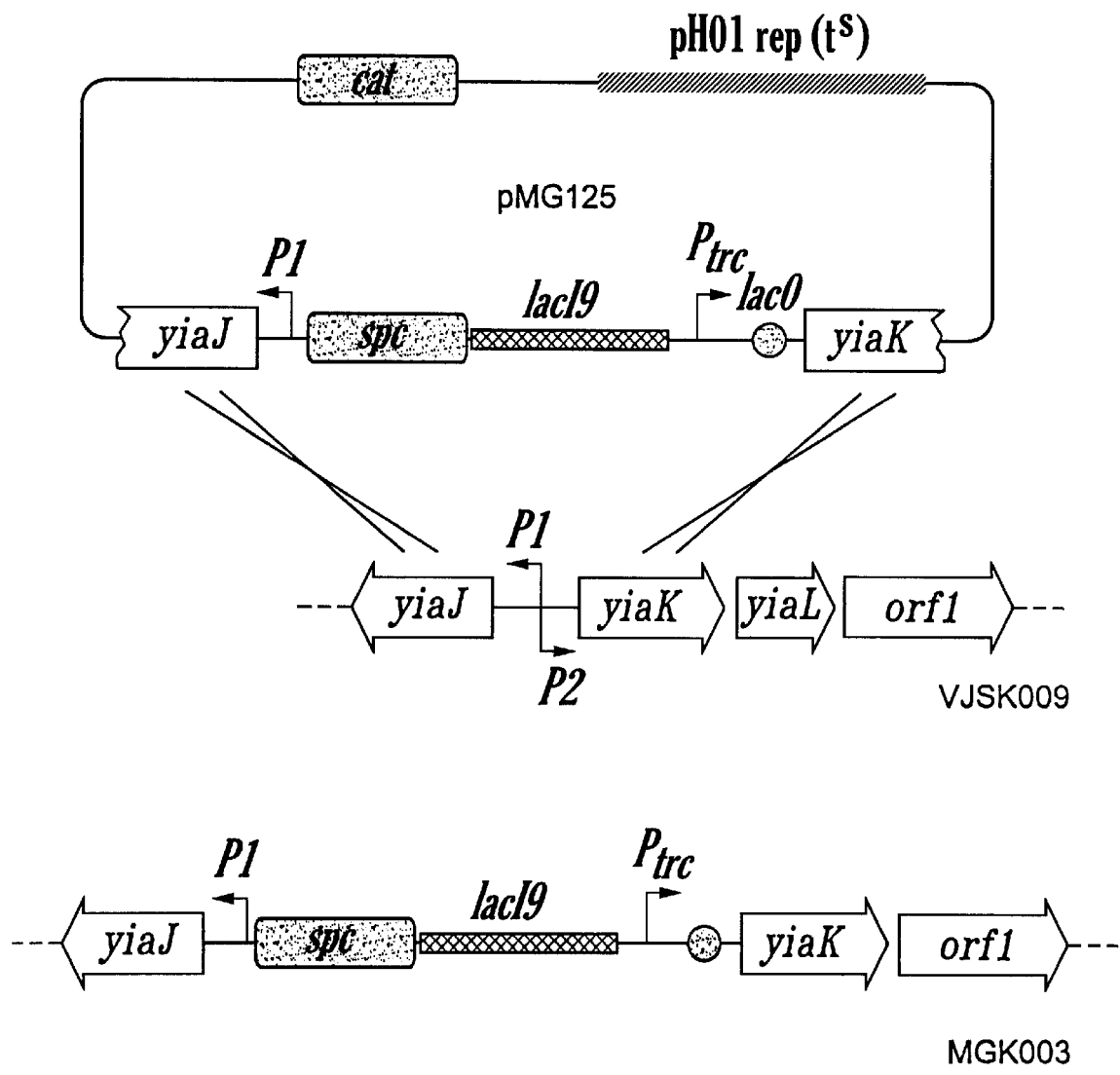
FIG. 10 shows a schematic of the construction of the Tester Strain. The plasmid pMG125 is shown which comprises: (i) a chloramphenicol resistance marker (cat); (ii) the thermosensitive origin of replication from plasmid pHO1 (pHO1 rep (ts) ) ; (iii) a 0.8 kb fragment containing the 5' region of the yiaJ gene and its promoter sequences; (iv) the spectinomycin resistance marker (spc); (v) the lacI$^q$-lacO-trc promoter fragment; and (vi) a 1 kb fragment containing the 5' end of yiaK, including its ribosome binding site for translation initiation while excluding the promoter sequences of the yiaK-S operon. The recombinant plasmid pMG125 was introduced into *K. oxytoca* wild type strain VJSK009 by transformation at 30° C., the permissive temperature for pMAK705 replication. Chromosomal integration of the pMG125 insert into VJSK009 was achieved by double crossover at the yiaJ-K locus such that the endogenous promoter of the yiaK-S operon was replaced with the inducible lacI$^q$-trc promoter system in the resulting recombinant cell, MGK003.

To engineer *K. oxytoca* as a host strain for the selection of biocatalysts which produce AsA, the promoter of the yiaK-S operon was replaced with a DNA fragment that contained the trp-lac hybrid promoter of transcription, the lacO operator, and the lacI$^q$ repressor gene (Brosius, J. 1992. Meth. Enzymol. 216:469–483). This allows the yiaK-S operon, and therefore AsA catabolism, to be turned ON and OFF in a tightly controlled manner in the presence or absence of IPTG, a non-metabolizable inducer of the lac promoter. Practically, a 5-way ligation was set up among: (i) the pMAK705 integration vector which carries a chloramphenicol resistance marker and the thermosensitive origin of replication from plasmid pHO1 (Hamilton, C. M., et al., 1989. J. Bacteriol. 171:4617–4622); (ii) a 0.8 kb fragment containing the 5' region of the yiaJ gene and its promoter sequences; (iii) the spectinomycin resistance marker retrieved from *Staphylococcus aureus* Tn554 (Murphy, E. 1985. Mol. Gen. Genet. 200:33–39) to follow integration events; (iv) the lacI$^q$-lacO-trc promoter fragment retrieved from pSE380 (InVitrogen, Carlsbad, Calif.); and (v) a 1 kb fragment containing the 5' end of yiaK, including its ribosome binding site for translation initiation while excluding the promoter sequences of the yiaK-S operon (FIG. 10).

The recombinant plasmid, pMG125, was introduced into *K. oxytoca* wild type strain VJSK009 by transformation at 30° C., the permissive temperature for pMAK705 replication. Chromosomal integration of the pMG125 insert by double crossover at the yiaJ-K locus was achieved by successive temperature switches as described by (Hamilton, C. M., et al., 1989. supra). PCR analyses were performed on 12 candidates to verify that the endogenous promoter of the yiaK-S operon had been replaced with the inducible lacI$^q$-trc promoter system (FIG. 10).

The resulting strain, MGK003, proved able to grow on M9 minimal medium supplemented with AsA 0.25% and IPTG 10 to 100 µM, while no growth was observed on the same medium lacking IPTG.

Example 2

Preparation of Environmental DNA Libraries

An example of a currently preferred method for the isolation of DNA from environmental samples is provided below. In the example, purification from soil and water samples are described, however samples can be from any environmental source and the methods adapted according to practices well-known in the art.

Direct Isolation of Total DNA from Soil and Water Samples

Total microbial DNA was isolated from various soil and water samples according to the following procedure which is derived and modified from Steffan, R. J., et al., 1988. Appl. Environ. Microbiol. 54:2908–2915; Whatling, C. A., and C. M. Thomas. 1993. Anal. Biochem. 210:98–101; and Zhou, J., et al., 1996. Appl. Environ. Microbiol. 62:316–322.

1. Begin with 100 g wet soil or 50 g dry soil; 150 mL sodium phosphate buffer 0.1 M, pH 4.5; and 5 g PVPP (acid washed).
2. Blender—medium speed—3 times for 1 min (cool down between each cycle). Add 0.5 mL SDS 20%, blend 5 more seconds.
3. Centrifuge 10 min at 1,000 g at 10° C.
4. Keep supernatant. Repeat extraction twice with soil pellet.
5. Combine the 3 supernatants. Centrifuge 20 min at 10,000 g at 10° C.
6. Wash pellet with cold 0.1% sodium-0.1% sodium pyrophosphate. Homogenize with blender for 1 min or shake. Centrifuge 20 min at 10,000 g at 10° C.
7. Wash pellet with 33 mM Tris-HCl, 1 mM EDTA, pH 8.0.
8. Resuspend in 2 mL 10 mM Tris, pH 7.6; 1 N NaCl.
9. Mix with equal volume 1.2% LMP agarose at 42° C. Pour into 1 mL syringes. Polymerize for 20 min at 4° C.
10. Incubate 3–4 hours at 37° C. in 20 vol. 1 N NaCl; 100 mM EDTA; 10 mM Tris, pH 7.5; 1% sarkosyl; 1 mg/mL lysozyme.
11. Add 1 mg/mL proteinase K. Incubate overnight at 45° C.
12. Wash agarose plugs twice with TE. Store in 100 mM EDTA; 10 mM Tris at 4° C.
13. Load noodles on LMP agarose gel 0.7%. Cut out chromosomal band. Heat 15 min at 65° C. in TE buffer. Add 2 U GelZyme (InVitrogen) per 200 µL 1% agarose. Incubate for 2 h at 40° C. EtOH precipitate for no more than 30 min at –20° C.

Preparation of Total DNA from Post-Enrichment Cultures

Aliquots from 18 water or soil samples were used to inoculate 50 mL of M9 minimal medium supplemented with any one of the following carbon sources: 0.5% 2-KLG; 0.25% L-idonate (L-IA); 0.25% L-gulonate (L-GuA) and 0.25% ascorbate. Culture flasks were incubated for 2 to 3 days at 30° C. without agitation.

Total DNA was isolated from these cultures as follows:

1. 20 mL were centrifuged for 5 min at 6,000 rpm.
2. Pellets were washed with 5 mL Tris 10 mM, EDTA 1 mM pH 8.0 (TE), were centrifuged again, and were resuspended in 0.9 mL TE.
3. Lysozyme (5 mg/mL) and RNase 100 (µg/mL) were added, and cells were incubated for 10 min at 37° C.
4. Sodium dodecylsulfate (SDS) was added to a final concentration of 1%, and the tubes were gently shaken until lysis was completed.
5. 200 mL of a 5 N NaClO$_4$ stock solution were added to the lysate.
6. The mixture was extracted once with one volume of phenol:chloroform (1:1) and once with one volume of chloroform.
7. Chromosomal DNA was precipitated by adding 2 mL of cold (–20° C.) ethanol and gently coiling the precipitate around a curved Pasteur pipette.
8. DNA was dried for 30 min at room temperature and was resuspended in 100 to 500 µL of Tris 10 mM, EDTA 1 mM, NaCl 50 mM pH 8.0 to obtain a DNA concentration of 0.5 to 1 µg/µL.

Example 3

Figure 12:
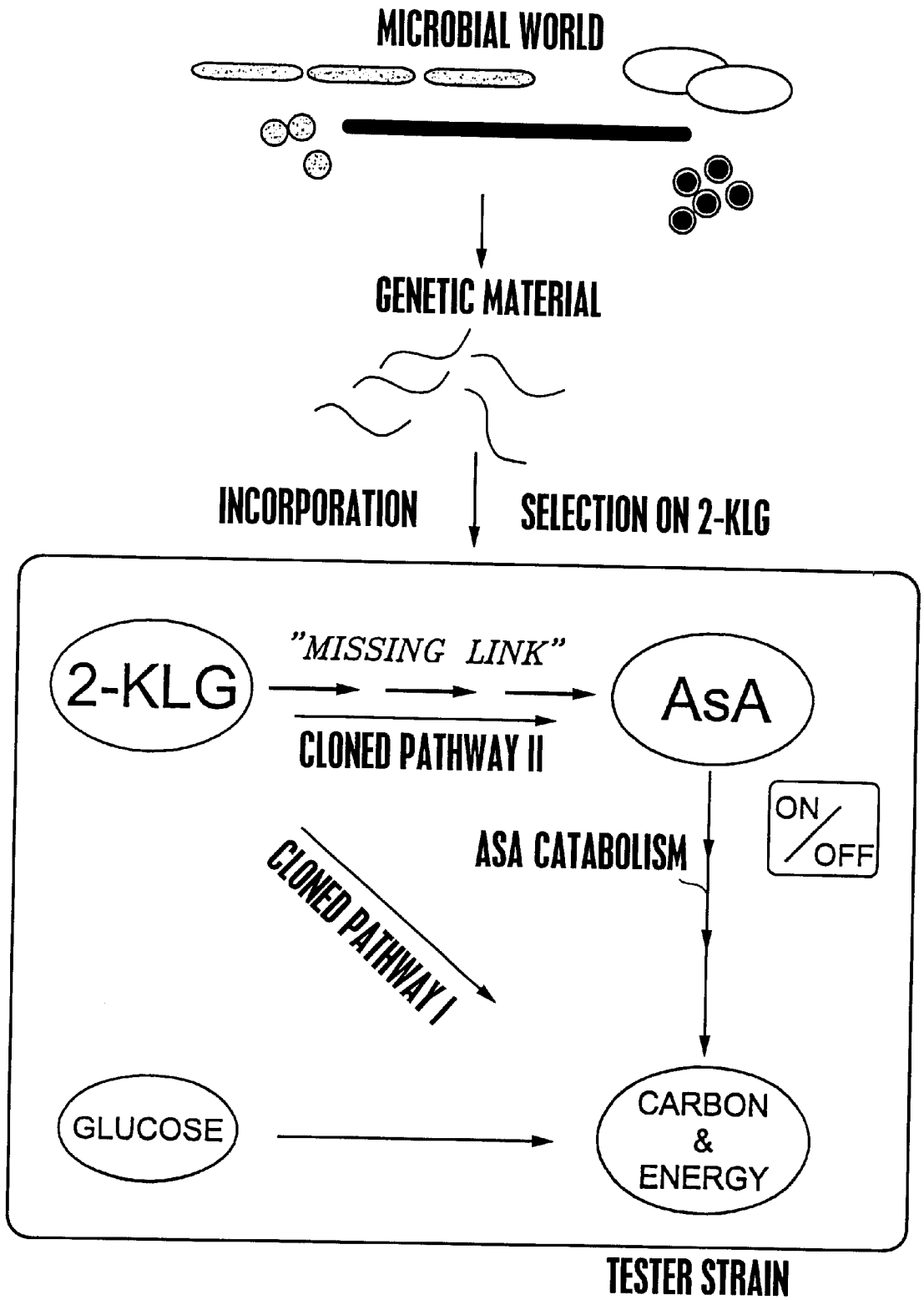
FIG. 12 shows a schematic representation of a more specific example of metabolic selection process, in which "S" is 2-KLG and "T" is AsA. In this case, the gene(s) of interest are those that catalyze the conversion of 2-KLG to AsA.

Selection for Nucleic Acid which Converts 2-KLG to AsA (FIG. 12)

This example is exemplary of how to select for nucleic acid sequences that encode metabolic pathways, and therefore can be applied to the identification and selection of sequences encoding other metabolic pathways. Basically, a nucleic acid library is made, according to methods well-known in the art, from nucleic acid sequences isolated from environmental samples (as described in Example 2, for example). This library is then transfected into the tester strain and the resulting pool of transfected cells selected for growth on the source compound (2-KLG in the example) in the absence of the target compound (ascorbate in the example) and the presence of the inducer.

Construction of an Enrichment DNA Library in a Cosmid Vector

The SuperCosl cosmid vector (Stratagene, La Jolla, Calif.) is a λ-based cloning system suitable for the cloning of large DNA fragments. After treatment according to the manufacturer's instructions, the 8 kb-long vector appears as two arms flanked by cos sites which are recognized by the λ-packaging machinery. Since only DNA molecules from 40 to 48 kb are efficiently packaged in λ-heads, this allows the selective cloning of 32 to 40 kb inserts between the two arms.

Chromosomal DNA extracted from 20 post-enrichment cultures was mixed in equal amounts. Five to ten $\mu$g of the mixture were partially digested with Sau3A restriction enzyme to obtain DNA fragments sized between 5 and 50 kb, were dephosphorylated, and were ligated with SuperCosl arms using conditions recommended by the supplier. One $\mu$g of the ligation mixture was used in an in vitro packaging reaction using the Gigapack III Gold packaging kit from Stratagene to create the cosmid library.

Clearly, this procedure can be used to make other chromosomal DNA libraries, for example from other enriched environmental samples, or from chromosomal DNA extracted directly from environmental samples.

Transfection and Selection of the Cosmid Library

Prior to transfection of *K. oxytoca* strain MGK003 with the packaging mixture, the tester strain was transformed with plasmid pCB382 expressing the *E. coli* lamB gene that functions as λ receptor, which appears to be absent or non-functional in most Klebsiella strains (De Vries, G. E., et al., 1984. Proc. Natl. Acad. Sci. USA 81:6080–6084). The resulting MGK003 [λ$^s$] strain was transfected with the packaged products as follows:

1. Five mL of liquid LB medium supplemented with 0.2% maltose and 10 mM MgSO$_4$ were inoculated from an overnight preculture of strain MGK003 [pCB382].
2. Cells were grown to an OD$_{600}$ of 0.5, were centrifuged at 500×g for 10 min, and were resuspended in the same volume of 10 mM MgSO$_4$.
3. The packaging products were mixed with 2 mL of cells in 15 mL culture tubes, and were incubated for 20 min at 39° C. without shaking.
4. After adding 2.5 mL of 2×YT (1% NaCl; 1% yeast extract; 1.6% tryptone), cells were incubated at 37° C. for 1 h under gentle agitation.
5. A 100 $\mu$L-aliquot was plated on LB-kanamycin medium to determine the number of clones present in the cosmid library.
6. The remainder was centrifuged at 3000 g for 5 min and was resuspended in 1 mL of M9 minimal medium supplemented with 10 $\mu$M IPTG (IPTG concentration can be varied up to 100 $\mu$M), and aliquots (200 $\mu$L) were plated on M9 plates containing 0.5% 2-KLG and 50 $\mu$M IPTG. 7.

Plates were incubated at 37° C. for 36 h for selecting candidate pathways that would convert 2-KLG to AsA. (Alternatively, selection can be done at 30° C.)

Among 500,000 clones to which a first selection round was applied, approximately 100 colonies of various sizes appeared on 2-KLG/IPTG plates. These were re-streaked on: (i) LB-kanamycin to verify the presence of the cosmid vector; (ii) 2-KLG/IPTG; and (iii) 2-KLG lacking IPTG to determine if growth of the positive clones on 2-KLG was dependent upon the expression of AsA catabolism.

Two clones were retained that grew on LB-kanamycin and 2-KLG/IPTG, but not on 2-KLG without IPTG within 20 h at 37° C. To verify that the observed phenotype was conferred by the cloned DNA, cosmid DNA was extracted from these two clones and introduced, by electroporation, into strain MGK003. In both cases, the back-cross gave a phenotype identical to that of the original clone obtained in the selection process (Data not shown).

Selection of libraries can also be done on other carbon sources to isolate other pathways, for example on L-gulonate (0.25%) plus IPTG to isolate pathways from L-gulonate to AsA, or on L-idonate (0.25%) plus IPTG to isolate pathways from L-idonate to AsA.

Example 4

Isolation of Other Pathways

The metabolic selection strategy described above can also be used for the isolation of other pathways of interest, for example from 2-KLG to L-idonate, or 2-KLG to L-gulonate, or alternatively, to identify new reductase enzymes capable of the conversion of 2,5-DKG to 2-KLG. This conversion is one of the slow steps in the production of ascorbate, so identification of an enzymatic method would be economically useful. Basically, the strategy described in the examples above can be used to isolate any pathway to metabolize a compound as a carbon, nitrogen, sulfur, or potentially, a phosphorous source.

Example 5

Directed Evolution of Enzymes

This metabolic selection method is also capable of facilitating the directed evolution of enzymes. One can use this technique to screen known enzymes for mutations leading to higher efficiency, or to better specify optimal temperature or cofactor requirements, in the metabolic utilization of a compound. The mutations can be the result of natural evolution, the result of PCR or chemical mutagenesis, or created through techniques like DNA shuffling.

Example 6

Glucose to Ascorbic Acid Directly

Another permutation on this strategy that can be envisioned is to find new pathways for already existing processes, e.g. selection for a new pathway for the conversion of glucose to ascorbic acid using only a few enzymatic steps. This is feasible using, for example, a strain for which the sequence of the entire genome is known, such as *E. coli* or *B. subtilis*. The genes for the metabolism of glucose can be mutagenized such that the strain can no longer use glucose as a carbon/energy source, and then glucose-utilization pathways can be selected for as described in the previous examples.

Example 7

Ascorbate Biosensor (FIG. 13)

As mentioned above, the yiaJ protein is thought to be a regulator for the Yia operon. The experiments of the invention indicate that the regulatory activity of YiaJ may be, in part, modulated by sensing ascorbate. Thus, it is currently believed that the "sensing" of ascorbate by YiaJ (perhaps through binding, although the authors do not wish to be restricted to this interpretation) leads to the activation of the Yia operon, and thus the use of ascorbate as a carbon/energy source. This potentially results in an extremely sensitive "biosensor" for ascorbate. Thus, for example, it is envisioned that yiaJ could be placed in a construct such that when YiaJ bound ascorbate a detectable signal resulted, i.e. instead of turning "ON" or "OFF" the Yia operon, YiaJ could turn "ON" or "OFF" a gene which produces a detectable signal, for example a gene for fluorescence (e.g. β-galactosidase), luminescence (e.g. luciferase), or color (lac operon, or green flourescent protein). Methods of constructing these signal constructs are well-known in the art (e.g. Simpson, et al. 1998. TIBTECH 16: 332–338; Applegate, et al. 1998. Applied Environ. Microbiol. 64: 2730–2735; Selifoncva and Eaton, 1996. Applied Environ. Microbiol. 62: 778–783). .

These biosensor constructs can also be used in the methods of the invention for screening for a metabolic selection pathway instead of using selection on an essential factor or element. In this case, the tester strain would be one that does not have the source to target pathway as determined by the absence of target being detected by the biosensor in the presence or the absence of the source compound. Thus, the biosensor would need to "sense" and to "react to" the presence of the target compound by any one of the methods described above. Following transfection of the library of nucleic acid from environmental sources, the resulting cells would be screened for the presence of the target compound using the biosensor. In order to facilitate the numbers of colonies that would need to be screened, this could be automated read in luminescent or flourescent readers or sorted by FACS prior to further testing and identification of individual colonies. Although this requires more initial screening than selection using an essential element, this method offers an alternative approach when the appropriate tester strain or the metabolic pathway is not available for screening using an essential factor. Thus, the biosensor method provides the flexibility to identify pathways for compounds that are not metabolizable to an essential element, factor, or nutrient, but can be any compound for which a "biosensor" can be identified. Biosensors can be identified and created as described above.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. A method of screening for a nucleic acid molecule encoding a metabolic pathway that converts a source compound to a target compound, said method comprising:

(1) providing a cell containing one or more genes responsible for converting a target compound to provide a detectable signal, wherein said one or more genes are under the control of an inducible promoter, and wherein said detectable signal is not produced in the presence of said source compound;

(2) expressing an isolated nucleic acid molecule potentially encoding said metabolic pathway in said cell; and (3) identifying cell that produces a said detectable signal in the presence of said source compound and an inducer of said promoter, but not in the presence of said source compound and absence of said inducer, wherein the identified cell contains a nucleic acid molecule encoding a metabolic pathway that converts said source compound to said target compound.

2. The method of claim 1, wherein said nucleic acid molecule encoding a metabolic pathway is selected from the group consisting of mutagenized DNA, environmental DNA, combinatorial libraries, and recombinant DNA.

3. The method of claim 1, wherein said nucleic acid molecule encoding a metabolic pathway comprises environmental DNA.

4. The method of claim 3, wherein said environmental DNA is isolated from one or more sources selected from the group consisting of mud, soil, water, sewage, flood control channels, and sand.

5. The method of claim 2, wherein said mutagenized DNA is the result of mutagenesis by a process selected from the group consisting of random, chemical, PCR-based, and directed mutagenesis.

6. The method of claim 1, wherein said detectable signal is selected from the group consisting of growth, fluorescence, luminescence, and color.

7. The method of claim 1, wherein said detectable signal is growth.

8. The method of claim 7, wherein said target compound is metabolized to an element selected from the group consisting of carbon, phosphorous, nitrogen, and sulfur.

9. The method of claim 8, wherein said element is carbon.

10. The method of claim 1, wherein said target compound is selected from the group consisting of ascorbate and 2-Keto-L-Gulonate.

11. The method of claim 1, wherein said inducible promoter comprises the trp-lac hybrid promoter.

12. The method of claim 1, wherein said cell is a bacterial cell.

13. The method of claim 12, wherein said cell is a *Klebsiella oxytoca* cell.

14. The method of claim 1, wherein said one or more genes are naturally present in said cell.

15. The method of claim 1, wherein said one or more genes have been introduced into said cell.

* * * * *

SEQUENCE LISTING

<160> NUMBER OF SEQ ID NOS: 33

<210> SEQ ID NO 1
<211> LENGTH: 816
<212> TYPE: DNA
<213> ORGANISM: yia j

<400> SEQUENCE: 1

| | | | | | | |
|---|---|---|---|---|---|---|
| atgggcacaa | aagaaagcga | gaacacgcaa | gataaagaga | ggcctgccgg | aagtcagagc | 60 |
| cttttcgtg | ggttgatgct | aattgagatc | ctgagtaatt | atccaaatgg | ctgtcccgtg | 120 |
| gcgcatctgt | cggaactggc | gggactgaac | aaaagtaccg | ttcatcgctt | attacagggg | 180 |
| ctgcagtcct | gcgggtacgt | gacgcctgcc | ccggcgcgg | ggagctatgc | gctgacgaca | 240 |
| aaatttatcc | gcgttggcca | aaaggcgttg | tcgtcgctga | atattatcca | cgtcgcggcg | 300 |
| ccgcatcttg | aggcgcttaa | cctggccacc | ggcgagacgg | tgaacttctc | cagccgtgaa | 360 |

```
gatgaccacg cgatcctgat ttataagctg gagccgacca ccggtatgct gcgtacgcgc    420
gcctatattg gccagcacat gcgctgtact gctcggcaat gggcaaagat ttatatggcg    480
tttggccatc ctgactacgt tgagagctac tggaattcac accaggagat tatccagccg    540
ctgacccgta ataccattac cggcttgcct gcgatgcatg atgaactggc gcagatccgc    600
gagcgaaata tggcgatgga cagggaagag aacgagctgg gcgtgtcgtg cctggctgtc    660
cccgtttttg atatccatgg gcgcgtgcct tatgccattt ctatctctct atcaacatcg    720
cgcctcaagc aggtgggaga gaaaaattta ctcaagccgc tacgcgatac ggcagaggcg    780
atttctcgcg aactgggctt ttccgtgcgg gaaggt                              816
```

```
<210> SEQ ID NO 2
<211> LENGTH: 996
<212> TYPE: DNA
<213> ORGANISM: yia k

<400> SEQUENCE: 2
atgaaagtca cgtttgagca gttaaaagag gcattcaatc gggtactgct ggacgcgtgc     60
gtcgcccggg aaaccgccga tgcctgcgca gaaatgtttg cccgcaccac cgaatccggc    120
gtctattctc acggcgtgaa ccgctttcct cgcttcatcc agcagttgga taacggcgac    180
attatccctg aggctcaacc gcagcgggtg accacgctcg gcgccatcga acagtgggat    240
gctcagcgtt ccatcggcaa cctgacggcg aaaaagatga tggatcgggc cattgagctg    300
gcctccgatc acggtatcgg cctggtcgcc ttacgtaatg ctaaccactg gatgcgcggc    360
ggcagctacg gctggcaggc ggcggaaaaa ggctacatcg gtatctgctg gaccaactcc    420
atcgccgtta tggcgccatg gggcgctaaa gagtgccgta tcggtaccaa cccgctgatc    480
gtcgccattc gtcgacgcc gatcaccatg gtggatatgt cgatgtcgat gttctcctac    540
ggcatgctgg aggttaaccg ccttgccggc cgcgaactgc ccgtggacgg cggattcgac    600
gatgacggtc gtttgaccaa agagccgggg acgatcgaga aaaatcgccg catttttaccc    660 atgggctact ggaaaggttc cggcctgtcg atcgtgctgg atatgattgc caccctcctc    720
tccaacggat cgtcggttgc cgaagtgacc caggaaaaca gcgatgaata tggcgttcg    780 cagatcttca tcgctattga agtggataag ctgatcgacg gcgcaacccg cgacgccaag    840
ctgcaacgga ttatggattt catcaccacc gccgagcgcg ccgatgaaaa tgtggcggtc    900
cgtcttcctg gccatgaatt tacccgtctg ctggatgaaa accgccgcaa cggcattacc    960
gtcgatgaca gcgtatgggc caaaattcag gcgctg                              996
```

```
<210> SEQ ID NO 3
<211> LENGTH: 462
<212> TYPE: DNA
<213> ORGANISM: yia l

<400> SEQUENCE: 3 atgattttttg gtcatattgc tcaacctaat ccgtgtcgtc tgcccgcggc cattgagcgg     60
gcgcttgatt tcctgcgcac gacggatttc cacgcgctgg caccccggcgt cgtggaaatc    120 gacggccaaa acatcttcgc gcaggttatc gacttaacca ctcgcgatgc cgctgaaaat    180
cgtccggagg tccaccgtcg ctatctggat atccagtttc tggcatcggg cgaagaaaaa    240
atcggtatcg ccattgatac cggcaataat caaatcagcg aatctttatt agaacagcgc    300
gatattattt tttatcacga cagcgaacat gaatcgttct ttgaaatgac gccaggcaac    360
```

-continued

| | | |
|---|---|---|
| tatgcgatat ttttcccgca agatgttcat cgtcctggat gtaataaaac tgtagccacg | 420 |
| ccgatccgca aaatagtcgt taaagtcgct atttcagttt ta | 462 |

<210> SEQ ID NO 4
<211> LENGTH: 945
<212> TYPE: DNA
<213> ORGANISM: orf1

<400> SEQUENCE: 4

| | | |
|---|---|---|
| atgaattcga ataataccgg ttacattatc ggtgcgtacc cctgtgcccc ctgtgcaccc | 60 |
| tcatttcacc aaaagagtga agaggaagag atggaattct ggcggcagct ctccgacacc | 120 |
| ccggatattc gcgggctgga gcaaccctgc ctaccctgcc ttgaacatct tcatccgctc | 180 |
| ggcgacgagt ggttattgcg ccatacccg ggacactggc agattgtcgt taccgccatc | 240 |
| atggaaacca tgcgccgccg cggtgaaaac ggcggctttg gctggcgtc cagcgacgaa | 300 |
| acgcagcgca aagcctgcgt ggagtactat cgccacctgc agcagaagat cgctaaaatc | 360 |
| aatggcaata ccgccggaaa ggtcattgcc cttgagcttc acgccgcccc gctggcgggc | 420 |
| aatgccaacg tggctcaggc taccgacgcc tttgcccgtt cattaaaaga aattacccgc | 480 |
| tgggactggt cctgcgagct ggtgctggag cactgcgacg cgatgaccgg cagcgcgccg | 540 |
| cgcaaaggat ttttgccgtt agaaaacgtg ctggaagcca ttgccgatta tgacgttggc | 600 |
| atttgtatta actgggcgcg ttcggccatt gaagggcgga ataccgtgct accgctcacc | 660 |
| catacgcagc aggtaaaacg ggcaggaaag ctcggcgcgc tgatgttttc tggcacgacg | 720 |
| cagaccggcg agtacggcga atggcaggat ttacacgcgc cgttcgcgcc tttctgcccg | 780 |
| cagagcctga tgaccaccga acacgctcgt gaattatttg cctgcgcagg aaccgccccc | 840 |
| ctgcaatttt caggcattaa attactggaa attaatgcca gcgcaaacgt tgatcatcgc | 900 |
| atcgcgatat tacgcgacgg catctccgcg ctaaaacaag cacaa | 945 |

<210> SEQ ID NO 5
<211> LENGTH: 1317
<212> TYPE: DNA
<213> ORGANISM: yia x2

<400> SEQUENCE: 5

| | | |
|---|---|---|
| atgaatataa cctctaactc tacaaccaaa gatataccgc ccagcgctg gttaagaatc | 60 |
| attccgccta tactgatcac ttgtattatt tcttatatgg accgggtcaa tattgccttt | 120 |
| gcgatgcccg gaggtatgga tgccgactta ggtatttccg ccaccatggc ggggctggcg | 180 |
| ggcggtatt tcttatcgg ttatctattt ttacaggttc ccggcgggaa aattgccgtt | 240 |
| cacggtagcg gtaagaaatt tatcggctgg tcgctggtcg cctgggcggt catctccgtg | 300 |
| ctgacggggt taattaccaa tcagtaccag ctgctggccc tgcgcttctt actgggcgtg | 360 |
| gcggaaggcg gtatgctgcc ggtcgttctc acgatgatca gtaactggtt ccccgacgct | 420 |
| gaacgcggtc gcgccaacgc gattgtcatt atgtttgtgc cgattgccgg gattatcacc | 480 |
| gccccactct caggctggat tatcacggtt ctcgactggc gctggctgtt tattatcgaa | 540 |
| ggtttgctct cgctggttgt tctgggttctg tgggcataca ccatctatga ccgtccgcag | 600 |
| gaagcgcgct ggatttccga agcagagaag cgctatctgg tcgagacgct ggccgcggag | 660 |
| caaaaagcca ttgccggcac cgaggtgaaa aacgcctctc tgagcgccgt tctctccgac | 720 |
| aaaaccatgt ggcagcttat cgccctgaac ttcttctacc agaccggcat ttacggctac | 780 |
| accctgtggc tacccaccat tctgaaagaa ttgacccata gcagcatggg gcaggtcggc | 840 |

| | |
|---|---|
| atgcttgcca ttctgccgta cgtcggcgcc attgctggga tgttcctgtt ttcctcccctt | 900 |
| tcagaccgaa ccggtaaacg caagctgttc gtctgcctgc cgctgattgg cttcgctctg | 960 |
| tgcatgttcc tgtcggtggc gctgaaaaac caaatttggc tctcctatgc cgcgctggtc | 1020 |
| ggctgcggat tcttcctgca atcggcggct ggcgtgttct ggaccatccc ggcacgtctg | 1080 |
| ttcagcgcgg aaatggcggg cggcgcgcgc ggggttatca cgcgcttgg caacctcggc | 1140 |
| ggattttgtg gcccttatgc ggtcggggtg ctgatcacgt tgtacagcaa agacgctggc | 1200 |
| gtctattgcc tggcgatctc cctggcgctg ccgcgctga tggcgctgct gctgccggcg | 1260 |
| aaatgcgatg ccggtgctgc gccggtaaag acgataaatc cacataaacg cactgcg | 1317 |

<210> SEQ ID NO 6
<211> LENGTH: 1503
<212> TYPE: DNA
<213> ORGANISM: lyxk

<400> SEQUENCE: 6

| | |
|---|---|
| atgagcaaga acaggccctt ctggctgggt attgattgcg gcggcaccta tctgaaagcc | 60 |
| ggtttatatg acgccgaagg tcatgaacat ggcattgtgc ggcaagcgct acggacgatg | 120 |
| tcgcccctgc cgggttacgc cgaacgcgac atgcgccagc tctggcaaca ctgcgcggcg | 180 |
| accattgccg ggctattaca gcaggcaggt gtatccggcg aacagattaa aggcgtgggc | 240 |
| atctccgctc agggtcaagg gctctttctc ctcgataagc aggatcggcc gctgggtaac | 300 |
| gccatcctct cctccgatcg tcgggcgctg aaaatcgttc agcgctggca gcgggaccgt | 360 |
| attcccgaac ggctctatcc cgttacccgc cagacgctgt ggaccggaca tccggcttct | 420 |
| ttgctgcgct gggtaaaaga gaatgaaccc cagcgctacg cgcaaattgg ctgcgtgatg | 480 |
| atggggcatg actatctgcg ctggtgctta accggcgcga agggctgcga ggagagcaac | 540 |
| atctccgagt ccaacctcta acatggcc atgggccagt acgacccgcg cctgaccgag | 600 |
| tggctgggca tcggtgaaat cgatagcgcg ctgcccccg ttgtagggtc agccgaaatt | 660 |
| tgcggggaga tcaccgctca ggcagccgct ttaaccggtc tggcggcggg tactcccgtc | 720 |
| gttggcggcc tgtttgacgt ggtctccacc gcccttttgcg ccgggattga ggatgagtcg | 780 |
| accctcaatg cggtgatggg gacctgggcc gtcactagcg gtatcgctca cggcctgcgc | 840 |
| gaccatgagg cccacccctta cgtctatggc cgctacgtca atgacggcca gtatatcgtt | 900 |
| cacgaagcca gcccgacctc atccggcaac ctcgaatggt ttaccgccca gtgggcgat | 960 |
| ctctcgtttg atgagatcaa tcaggccgtc gccagcctgc cgaaagccgg gagcgagctg | 1020 |
| ttttttctgc cgtttctgta tggcagcaac gccgggctgg agatgacctg cggctttac | 1080 |
| ggcatgcagg cgctgcatac ccgcgcgcac ctgctgcagg cggtttatga aggcgtggta | 1140 |
| tttagccata tgacccacct cagccgtatg cgcgaacgct tacaaacgt tcaggccctg | 1200 |
| cgcgtcaccg gcggcccggc gcactccgac gtctggatgc agatgctggc ggacgtaagc | 1260 |
| ggcttacgca ttgaactccc gaaggtggaa gagaccggct gttttggcgc ggccctcgcc | 1320 |
| gctcgtgtcg gtaccggcgt ataccgcagc tttagcgaag cccggcgcgc ccggcagcac | 1380 |
| ccggtgcgca cgctgctgcc cgatatgacc gcccacgcgc gctatcagcg caaataccgc | 1440 |
| cactacctgc atttgattga agcactacag ggctatcacg cccgtattaa ggagcacgca | 1500 |
| tta | 1503 |

<210> SEQ ID NO 7

```
<211> LENGTH: 660
<212> TYPE: DNA
<213> ORGANISM: yia q

<400> SEQUENCE: 7
atgagccgac cattactgca gctggcgctc gaccatacca gccttcaggc tgcgcagcgc      60
gatgtcgccc tgctacagga tcacgttgat attgtggagg cgggaaccat cctctgctta     120
accgaagggc ttagcgcggt taaagccctg cgcgcccagt gtccgggaa gatcatcgtc      180 gccgactgga agtcgccga cgccggtgaa accctggcgc agcaggcctt tggcgctggc      240
gccaactgga tgaccatcat tgcgccgca ccgctcgcca cggtcgagaa aggccacgcc      300
gtggcccagg cctgcggcgg tgaaattcag atggagctgt cggcaactg gacgctggat      360 gacgcccgcg cctggtaccg taccggcgtc catcaggcga tttaccatcg cggacgcgat     420
gcccaggcca gcgggcagca gtgggggag gcggatctgg cgcgcatgaa agcgctgtcc      480
gatattggcc ttgagctatc gattaccggc ggcattaccc cagccgatct accgctgttc     540
aaagatatca cgtcaaagc ctttattgcc gggcgcgcgc tggcaggcgc cgcccatccg      600
gcgcgggttg ccgccgaatt ccacgcgcaa atcgacgcta tctggggaga acagcatgcg     660

<210> SEQ ID NO 8
<211> LENGTH: 858
<212> TYPE: DNA
<213> ORGANISM: yia r

<400> SEQUENCE: 8
atgcgtaacc acccgttagg tatttatgaa aaagcgctgg cgaaggatct cagctggcct      60
gagcggctgg tactggccaa agctgcggt tttgattttg tcgaaatgtc ggtggacgag      120
accgatgaac gccttccgcg cctggagtgg accccggccc agcgcgcatc gctggtgagc     180
gcgatgctgg aaaccgcggt cgccattccc tcgatgtgct tgtccgccca tcgccgtttc     240
ccctttggca gccgcgatga agcggtacgc gatcgggcgc gagagattat gaccaaagcc     300
atccgcctgg cgcgcgatct ggggatccgc accatccagc tggcgggtta cgacgtctat     360
tacgaagagc atgatgaagg caccccggcag cgttttgccg aagggctggc ctgggcggta     420
gaacaggccg ccgccgcgca ggtaatgctg cggtgagga tcatggacac cgcctttatg      480
aactccatca gcaaatggaa aaagtgggac gagatgcttt cgtcaccgtg gtttaccgtc     540
tacccggacg tcggcaaccct cagcgcctgg ggaaacgacg tcaccgccga gctgaagctg     600
ggcatcgatc gtatcgccgc catccacctg aaagatacgc tgcccgtgac cgacgatagc      660
cctggccagt tccgcgacgt gccgttcggc gaaggatgcg tcgattttgt cggcatttt     720 aagacgctgc gcgagctgaa ctaccgcggt tcatttttga ttgagatgtg gacggagaaa     780
gccagcgagc cggtgctgga gattatccag gcccggcgct ggatcgaatc acggatgcag     840 gaaggggat tcacatgt                                                    858

<210> SEQ ID NO 9
<211> LENGTH: 714
<212> TYPE: DNA
<213> ORGANISM: yia s

<400> SEQUENCE: 9
atgttagaac aactgaaagc cgaggtactg gcggcaaacc tggccctccc cgcacacggc      60
ctggtcacct ttacctgggg caacgtcagc gcggtcgatg aaacgcgcaa gctgatggtc     120
attaagcctt ccggcgtcga atatgaggtg atgaccgccg acgatatggt ggtcgtagag     180
```

-continued

```
atggccagcg gtaaagtcgt tgaaggcggt aaaaaaccct cttcagatac gccaacgcat    240
ctggcgcttt atcgccgcta tccgcagatc ggcgggatcg tgcataccca ctcccgccac    300
gcgacgatct ggtcgcaggc cgggctcgat ctccccgcct ggggcaccac ccacgccgac    360
tacttctatg cgcgatcccc ctgtacccga cggatgaccg ttgaggagat aacggcgag    420 tatgagtatc agaccggcga ggtgattatc aaaacctttg aacagcgcgg cctggatccg    480
gcgcaaatcc cggcggtatt ggtccattca cacggcccct ttgcctgggg taaagacgcc    540
gccgacgccg tacataacgc cgtggtgctg gaggagtgcg cctacatggg cctcttctcg    600
cgccagtggc cacagctgcc ggatatgcag tctgaactgc tcgataaaca ctatctgcgt    660
aaacacggcg cgaacgctat tacgggcaaa actagtcccg cggaactccc cgga          714
```

<210> SEQ ID NO 10
<211> LENGTH: 272
<212> TYPE: PRT
<213> ORGANISM: YiaJ-Ko

<400> SEQUENCE: 10

```
Met Gly Thr Lys Glu Ser Glu Asn Thr Gln Asp Lys Glu Arg Pro Ala
1               5                   10                  15

Gly Ser Gln Ser Leu Phe Arg Gly Leu Met Leu Ile Glu Ile Leu Ser
            20                  25                  30

Asn Tyr Pro Asn Gly Cys Pro Val Ala His Leu Ser Glu Leu Ala Gly
        35                  40                  45

Leu Asn Lys Ser Thr Val His Arg Leu Leu Gln Gly Leu Gln Ser Cys
    50                  55                  60

Gly Tyr Val Thr Pro Ala Pro Ala Ala Gly Ser Tyr Ala Leu Thr Thr
65                  70                  75                  80

Lys Phe Ile Arg Val Gly Gln Lys Ala Leu Ser Ser Leu Asn Ile Ile
                85                  90                  95

His Val Ala Ala Pro His Leu Glu Ala Leu Asn Leu Ala Thr Gly Glu
            100                 105                 110

Thr Val Asn Phe Ser Ser Arg Glu Asp Asp His Ala Ile Leu Ile Tyr
        115                 120                 125

Lys Leu Glu Pro Thr Thr Gly Met Leu Arg Thr Arg Ala Tyr Ile Gly
    130                 135                 140

Gln His Met Arg Cys Thr Ala Arg Gln Trp Lys Ile Tyr Met Ala
145                 150                 155                 160

Phe Gly His Pro Asp Tyr Val Glu Ser Tyr Trp Asn Ser His Gln Glu
                165                 170                 175

Ile Ile Gln Pro Leu Thr Arg Asn Thr Ile Thr Gly Leu Pro Ala Met
            180                 185                 190

His Asp Glu Leu Ala Gln Ile Arg Glu Arg Asn Met Ala Met Asp Arg
        195                 200                 205

Glu Glu Asn Glu Leu Gly Val Ser Cys Leu Ala Val Pro Val Phe Asp
    210                 215                 220

Ile His Gly Arg Val Pro Tyr Ala Ile Ser Ile Ser Leu Ser Thr Ser
225                 230                 235                 240

Arg Leu Lys Gln Val Gly Glu Lys Asn Leu Leu Lys Pro Leu Arg Asp
                245                 250                 255

Thr Ala Glu Ala Ile Ser Arg Gly Leu Gly Phe Ser Val Arg Glu Gly
            260                 265                 270
```

<210> SEQ ID NO 11
<211> LENGTH: 332
<212> TYPE: PRT
<213> ORGANISM: YiaK-Ko

<400> SEQUENCE: 11

```
Met Lys Val Thr Phe Glu Gln Leu Lys Glu Ala Phe Asn Arg Val Leu
 1               5                  10                  15

Leu Asp Ala Cys Val Ala Arg Glu Thr Ala Asp Ala Cys Ala Glu Met
             20                  25                  30

Phe Ala Arg Thr Thr Glu Ser Gly Val Tyr Ser His Gly Val Asn Arg
         35                  40                  45

Phe Pro Arg Phe Ile Gln Gln Leu Asp Asn Gly Asp Ile Ile Pro Glu
     50                  55                  60

Ala Gln Pro Gln Arg Val Thr Thr Leu Gly Ala Ile Glu Gln Trp Asp
 65                  70                  75                  80

Ala Gln Arg Ser Ile Gly Asn Leu Thr Ala Lys Lys Met Met Asp Arg
                 85                  90                  95

Ala Ile Glu Leu Ala Ser Asp His Gly Ile Gly Leu Val Ala Leu Arg
            100                 105                 110

Asn Ala Asn His Trp Met Arg Gly Gly Ser Tyr Gly Trp Gln Ala Ala
        115                 120                 125

Glu Lys Gly Tyr Ile Gly Ile Cys Trp Thr Asn Ser Ile Ala Val Met
130                 135                 140

Ala Pro Trp Gly Ala Lys Glu Cys Arg Ile Gly Thr Asn Pro Leu Ile
145                 150                 155                 160

Val Ala Ile Pro Ser Thr Pro Ile Thr Met Val Asp Met Ser Met Ser
                165                 170                 175

Met Phe Ser Tyr Gly Met Leu Glu Val Asn Arg Leu Ala Gly Arg Glu
            180                 185                 190

Leu Pro Val Asp Gly Gly Phe Asp Asp Gly Arg Leu Thr Lys Glu
        195                 200                 205

Pro Gly Thr Ile Glu Lys Asn Arg Arg Ile Leu Pro Met Gly Tyr Trp
    210                 215                 220

Lys Gly Ser Gly Leu Ser Ile Val Leu Asp Met Ile Ala Thr Leu Leu
225                 230                 235                 240

Ser Asn Gly Ser Ser Val Ala Glu Val Thr Gln Glu Asn Ser Asp Glu
                245                 250                 255

Tyr Gly Val Ser Gln Ile Phe Ile Ala Ile Glu Val Asp Lys Leu Ile
            260                 265                 270

Asp Gly Ala Thr Arg Asp Ala Lys Leu Gln Arg Ile Met Asp Phe Ile
        275                 280                 285

Thr Thr Ala Glu Arg Ala Asp Glu Asn Val Ala Val Arg Leu Pro Gly
    290                 295                 300

His Glu Phe Thr Arg Leu Leu Asp Glu Asn Arg Arg Asn Gly Ile Thr
305                 310                 315                 320

Val Asp Asp Ser Val Trp Ala Lys Ile Gln Ala Leu
                325                 330
```

<210> SEQ ID NO 12
<211> LENGTH: 154
<212> TYPE: PRT
<213> ORGANISM: YiaL-Ko

<400> SEQUENCE: 12

```
Met Ile Phe Gly His Ile Ala Gln Pro Asn Pro Cys Arg Leu Pro Ala
```

```
                1               5                    10                   15

Ala Ile Glu Arg Ala Leu Asp Phe Leu Arg Thr Thr Asp Phe His Ala
                   20                  25                  30

Leu Ala Pro Gly Val Val Glu Ile Asp Gly Gln Asn Ile Phe Ala Gln
                   35                  40                  45

Val Ile Asp Leu Thr Thr Arg Asp Ala Ala Glu Asn Arg Pro Glu Val
               50                  55                  60

His Arg Arg Tyr Leu Asp Ile Gln Phe Leu Ala Ser Gly Glu Glu Lys
   65                  70                  75                  80

Ile Gly Ile Ala Ile Asp Thr Gly Asn Asn Gln Ile Ser Glu Ser Leu
                       85                  90                  95

Leu Glu Gln Arg Asp Ile Ile Phe Tyr His Asp Ser Glu His Glu Ser
                   100                 105                 110

Phe Phe Glu Met Thr Pro Gly Asn Tyr Ala Ile Phe Phe Pro Gln Asp
                   115                 120                 125

Val His Arg Pro Gly Cys Asn Lys Thr Val Ala Thr Pro Ile Arg Lys
               130                 135                 140

Ile Val Val Lys Val Ala Ile Ser Val Leu
   145                 150

<210> SEQ ID NO 13
<211> LENGTH: 315
<212> TYPE: PRT
<213> ORGANISM: ORF1

<400> SEQUENCE: 13

Met Asn Ser Asn Asn Thr Gly Tyr Ile Ile Gly Ala Tyr Pro Cys Ala
1               5                   10                  15

Pro Cys Ala Pro Ser Phe His Gln Lys Ser Glu Glu Glu Met Glu
                20                  25                  30

Phe Trp Arg Gln Leu Ser Asp Thr Pro Asp Ile Arg Gly Leu Glu Gln
                35                  40                  45

Pro Cys Leu Pro Cys Leu Glu His Leu His Pro Leu Gly Asp Glu Trp
            50                  55                  60

Leu Leu Arg His Thr Pro Gly His Trp Gln Ile Val Val Thr Ala Ile
65                  70                  75                  80

Met Glu Thr Met Arg Arg Gly Glu Asn Gly Gly Phe Gly Leu Ala
                85                  90                  95

Ser Ser Asp Glu Thr Gln Arg Lys Ala Cys Val Glu Tyr Tyr Arg His
                100                 105                 110

Leu Gln Gln Lys Ile Ala Lys Ile Asn Gly Asn Thr Ala Gly Lys Val
                115                 120                 125

Ile Ala Leu Glu Leu His Ala Ala Pro Leu Ala Gly Asn Ala Asn Val
            130                 135                 140

Ala Gln Ala Thr Asp Ala Phe Ala Arg Ser Leu Lys Glu Ile Thr Arg
145                 150                 155                 160

Trp Asp Trp Ser Cys Glu Leu Val Leu Glu His Cys Asp Ala Met Thr
                165                 170                 175

Gly Ser Ala Pro Arg Lys Gly Phe Leu Pro Leu Glu Asn Val Leu Glu
                180                 185                 190

Ala Ile Ala Asp Tyr Asp Val Gly Ile Cys Ile Asn Trp Ala Arg Ser
                195                 200                 205

Ala Ile Glu Gly Arg Asn Thr Val Leu Pro Leu Thr His Thr Gln Gln
                210                 215                 220
```

```
Val Lys Arg Ala Gly Lys Leu Gly Ala Leu Met Phe Ser Gly Thr Thr
225                 230                 235                 240

Gln Thr Gly Glu Tyr Gly Glu Trp Gln Asp Leu His Ala Pro Phe Ala
            245                 250                 255

Pro Phe Cys Pro Gln Ser Leu Met Thr Thr Glu His Ala Arg Glu Leu
            260                 265                 270

Phe Ala Cys Ala Gly Thr Ala Pro Leu Gln Phe Ser Gly Ile Lys Leu
            275                 280                 285

Leu Glu Ile Asn Ala Ser Ala Asn Val Asp His Arg Ile Ala Ile Leu
            290                 295                 300

Arg Asp Gly Ile Ser Ala Leu Lys Gln Ala Gln
305                 310                 315

<210> SEQ ID NO 14
<211> LENGTH: 439
<212> TYPE: PRT
<213> ORGANISM: YiaX2

<400> SEQUENCE: 14

Met Asn Ile Thr Ser Asn Ser Thr Thr Lys Asp Ile Pro Arg Gln Arg
1               5                   10                  15

Trp Leu Arg Ile Ile Pro Pro Ile Leu Ile Thr Cys Ile Ile Ser Tyr
            20                  25                  30

Met Asp Arg Val Asn Ile Ala Phe Ala Met Pro Gly Gly Met Asp Ala
            35                  40                  45

Asp Leu Gly Ile Ser Ala Thr Met Ala Gly Leu Ala Gly Gly Ile Phe
        50                  55                  60

Phe Ile Gly Tyr Leu Phe Leu Gln Val Pro Gly Gly Lys Ile Ala Val
65                  70                  75                  80

His Gly Ser Gly Lys Lys Phe Ile Gly Trp Ser Leu Val Ala Trp Ala
            85                  90                  95

Val Ile Ser Val Leu Thr Gly Leu Ile Thr Asn Gln Tyr Gln Leu Leu
            100                 105                 110

Ala Leu Arg Phe Leu Leu Gly Val Ala Glu Gly Gly Met Leu Pro Val
            115                 120                 125

Val Leu Thr Met Ile Ser Asn Trp Phe Pro Asp Ala Glu Arg Gly Arg
130                 135                 140

Ala Asn Ala Ile Val Ile Met Phe Val Pro Ile Ala Gly Ile Ile Thr
145                 150                 155                 160

Ala Pro Leu Ser Gly Trp Ile Ile Thr Val Leu Asp Trp Arg Trp Leu
            165                 170                 175

Phe Ile Ile Glu Gly Leu Leu Ser Leu Val Val Leu Val Leu Trp Ala
            180                 185                 190

Tyr Thr Ile Tyr Asp Arg Pro Gln Glu Ala Arg Trp Ile Ser Glu Ala
            195                 200                 205

Glu Lys Arg Tyr Leu Val Glu Thr Leu Ala Ala Glu Gln Lys Ala Ile
            210                 215                 220

Ala Gly Thr Glu Val Lys Asn Ala Ser Leu Ser Ala Val Leu Ser Asp
225                 230                 235                 240

Lys Thr Met Trp Gln Leu Ile Ala Leu Asn Phe Phe Tyr Gln Thr Gly
            245                 250                 255

Ile Tyr Gly Tyr Thr Leu Trp Leu Pro Thr Ile Leu Lys Glu Leu Thr
            260                 265                 270

His Ser Ser Met Gly Gln Val Gly Met Leu Ala Ile Leu Pro Tyr Val
            275                 280                 285
```

-continued

```
Gly Ala Ile Ala Gly Met Phe Leu Phe Ser Ser Leu Ser Asp Arg Thr
    290                 295                 300

Gly Lys Arg Lys Leu Phe Val Cys Leu Pro Leu Ile Gly Phe Ala Leu
305                 310                 315                 320

Cys Met Phe Leu Ser Val Ala Leu Lys Asn Gln Ile Trp Leu Ser Tyr
                325                 330                 335

Ala Ala Leu Val Gly Cys Gly Phe Phe Leu Gln Ser Ala Ala Gly Val
                340                 345                 350

Phe Trp Thr Ile Pro Ala Arg Leu Phe Ser Ala Glu Met Ala Gly Gly
            355                 360                 365

Ala Arg Gly Val Ile Asn Ala Leu Gly Asn Leu Gly Gly Phe Cys Gly
        370                 375                 380

Pro Tyr Ala Val Gly Val Leu Ile Thr Leu Tyr Ser Lys Asp Ala Gly
385                 390                 395                 400

Val Tyr Cys Leu Ala Ile Ser Leu Ala Leu Ala Ala Leu Met Ala Leu
                405                 410                 415

Leu Leu Pro Ala Lys Cys Asp Ala Gly Ala Ala Pro Val Lys Thr Ile
            420                 425                 430

Asn Pro His Lys Arg Thr Ala
            435

<210> SEQ ID NO 15
<211> LENGTH: 501
<212> TYPE: PRT
<213> ORGANISM: LyxK-Ko

<400> SEQUENCE: 15

Met Ser Lys Lys Gln Ala Phe Trp Leu Gly Ile Asp Cys Gly Gly Thr
1               5                   10                  15

Tyr Leu Lys Ala Gly Leu Tyr Asp Ala Glu Gly His Glu His Gly Ile
            20                  25                  30

Val Arg Gln Ala Leu Arg Thr Met Ser Pro Leu Pro Gly Tyr Ala Glu
        35                  40                  45

Arg Asp Met Arg Gln Leu Trp Gln His Cys Ala Ala Thr Ile Ala Gly
    50                  55                  60

Leu Leu Gln Gln Ala Gly Val Ser Gly Glu Gln Ile Lys Gly Val Gly
65                  70                  75                  80

Ile Ser Ala Gln Gly Gln Gly Leu Phe Leu Leu Asp Lys Gln Asp Arg
                85                  90                  95

Pro Leu Gly Asn Ala Ile Leu Ser Ser Asp Arg Arg Ala Leu Lys Ile
            100                 105                 110

Val Gln Arg Trp Gln Arg Asp Arg Ile Pro Glu Arg Leu Tyr Pro Val
        115                 120                 125

Thr Arg Gln Thr Leu Trp Thr Gly His Pro Ala Ser Leu Leu Arg Trp
    130                 135                 140

Val Lys Glu Asn Glu Pro Gln Arg Tyr Ala Gln Ile Gly Cys Val Met
145                 150                 155                 160

Met Gly His Asp Tyr Leu Arg Trp Cys Leu Thr Gly Ala Lys Gly Cys
                165                 170                 175

Glu Glu Ser Asn Ile Ser Glu Ser Asn Leu Tyr Asn Met Ala Met Gly
            180                 185                 190

Gln Tyr Asp Pro Arg Leu Thr Glu Trp Leu Gly Ile Gly Glu Ile Asp
        195                 200                 205

Ser Ala Leu Pro Pro Val Val Gly Ser Ala Glu Ile Cys Gly Glu Ile
```

```
            210                 215                 220
Thr Ala Gln Ala Ala Leu Thr Gly Leu Ala Ala Gly Thr Pro Val
225                 230                 235                 240

Val Gly Gly Leu Phe Asp Val Val Ser Thr Ala Leu Cys Ala Gly Ile
                245                 250                 255

Glu Asp Glu Ser Thr Leu Asn Ala Val Met Gly Thr Trp Ala Val Thr
                260                 265                 270

Ser Gly Ile Ala His Gly Leu Arg Asp His Glu Ala His Pro Tyr Val
                275                 280                 285

Tyr Gly Arg Tyr Val Asn Asp Gly Gln Tyr Ile Val His Glu Ala Ser
                290                 295                 300

Pro Thr Ser Ser Gly Asn Leu Glu Trp Phe Thr Ala Gln Trp Gly Asp
305                 310                 315                 320

Leu Ser Phe Asp Glu Ile Asn Gln Ala Val Ala Ser Leu Pro Lys Ala
                325                 330                 335

Gly Ser Glu Leu Phe Phe Leu Pro Phe Leu Tyr Gly Ser Asn Ala Gly
                340                 345                 350

Leu Glu Met Thr Cys Gly Phe Tyr Gly Met Gln Ala Leu His Thr Arg
                355                 360                 365

Ala His Leu Leu Gln Ala Val Tyr Glu Gly Val Val Phe Ser His Met
                370                 375                 380

Thr His Leu Ser Arg Met Arg Glu Arg Phe Thr Asn Val Gln Ala Leu
385                 390                 395                 400

Arg Val Thr Gly Gly Pro Ala His Ser Asp Val Trp Met Gln Met Leu
                405                 410                 415

Ala Asp Val Ser Gly Leu Arg Ile Glu Leu Pro Lys Val Glu Glu Thr
                420                 425                 430

Gly Cys Phe Gly Ala Ala Leu Ala Ala Arg Val Gly Thr Gly Val Tyr
                435                 440                 445

Arg Ser Phe Ser Glu Ala Arg Arg Ala Arg Gln His Pro Val Arg Thr
                450                 455                 460

Leu Leu Pro Asp Met Thr Ala His Ala Arg Tyr Gln Arg Lys Tyr Arg
465                 470                 475                 480

His Tyr Leu His Leu Ile Glu Ala Leu Gln Gly Tyr His Ala Arg Ile
                485                 490                 495

Lys Glu His Ala Leu
                500

<210> SEQ ID NO 16
<211> LENGTH: 220
<212> TYPE: PRT
<213> ORGANISM: YiaQ-Ko

<400> SEQUENCE: 16

Met Ser Arg Pro Leu Leu Gln Leu Ala Leu Asp His Thr Ser Leu Gln
1               5                   10                  15

Ala Ala Gln Arg Asp Val Ala Leu Leu Gln Asp His Val Asp Ile Val
                20                  25                  30

Glu Ala Gly Thr Ile Leu Cys Leu Thr Glu Gly Leu Ser Ala Val Lys
                35                  40                  45

Ala Leu Arg Ala Gln Cys Pro Gly Lys Ile Ile Val Ala Asp Trp Lys
            50                  55                  60

Val Ala Asp Ala Gly Glu Thr Leu Ala Gln Gln Ala Phe Gly Ala Gly
65                  70                  75                  80
```

```
Ala Asn Trp Met Thr Ile Ile Cys Ala Ala Pro Leu Ala Thr Val Glu
                 85                  90                  95

Lys Gly His Ala Val Ala Gln Ala Cys Gly Gly Glu Ile Gln Met Glu
            100                 105                 110

Leu Phe Gly Asn Trp Thr Leu Asp Asp Ala Arg Ala Trp Tyr Arg Thr
        115                 120                 125

Gly Val His Gln Ala Ile Tyr His Arg Gly Arg Asp Ala Gln Ala Ser
    130                 135                 140

Gly Gln Gln Trp Gly Glu Ala Asp Leu Ala Arg Met Lys Ala Leu Ser
145                 150                 155                 160

Asp Ile Gly Leu Glu Leu Ser Ile Thr Gly Gly Ile Thr Pro Ala Asp
                165                 170                 175

Leu Pro Leu Phe Lys Asp Ile Asn Val Lys Ala Phe Ile Ala Gly Arg
                180                 185                 190

Ala Leu Ala Gly Ala Ala His Pro Ala Arg Val Ala Ala Glu Phe His
            195                 200                 205

Ala Gln Ile Asp Ala Ile Trp Gly Glu Gln His Ala
        210                 215                 220

<210> SEQ ID NO 17
<211> LENGTH: 286
<212> TYPE: PRT
<213> ORGANISM: YiaR-Ko

<400> SEQUENCE: 17

Met Arg Asn His Pro Leu Gly Ile Tyr Glu Lys Ala Leu Ala Lys Asp
1               5                   10                  15

Leu Ser Trp Pro Glu Arg Leu Val Leu Ala Lys Ser Cys Gly Phe Asp
            20                  25                  30

Phe Val Glu Met Ser Val Asp Glu Thr Asp Glu Arg Leu Ser Arg Leu
        35                  40                  45

Glu Trp Thr Pro Ala Gln Arg Ala Ser Leu Val Ser Ala Met Leu Glu
    50                  55                  60

Thr Ala Val Ala Ile Pro Ser Met Cys Leu Ser Ala His Arg Arg Phe
65                  70                  75                  80

Pro Phe Gly Ser Arg Asp Glu Ala Val Arg Asp Arg Ala Arg Glu Ile
                85                  90                  95

Met Thr Lys Ala Ile Arg Leu Ala Arg Asp Leu Gly Ile Arg Thr Ile
            100                 105                 110

Gln Leu Ala Gly Tyr Asp Val Tyr Tyr Glu Glu His Asp Glu Gly Thr
        115                 120                 125

Arg Gln Arg Phe Ala Glu Gly Leu Ala Trp Ala Val Glu Gln Ala Ala
    130                 135                 140

Ala Ala Gln Val Met Leu Ala Val Glu Ile Met Asp Thr Ala Phe Met
145                 150                 155                 160

Asn Ser Ile Ser Lys Trp Lys Trp Asp Glu Met Leu Ser Ser Pro
                165                 170                 175

Trp Phe Thr Val Tyr Pro Asp Val Gly Asn Leu Ser Ala Trp Gly Asn
            180                 185                 190

Asp Val Thr Ala Glu Leu Lys Leu Gly Ile Asp Arg Ile Ala Ala Ile
        195                 200                 205

His Leu Lys Asp Thr Leu Pro Val Thr Asp Ser Pro Gly Gln Phe
    210                 215                 220

Arg Asp Val Pro Phe Gly Glu Gly Cys Val Asp Phe Val Gly Ile Phe
225                 230                 235                 240
```

```
Lys Thr Leu Arg Glu Leu Asn Tyr Arg Gly Ser Phe Leu Ile Glu Met
                245                 250                 255
Trp Thr Glu Lys Ala Ser Glu Pro Val Leu Glu Ile Ile Gln Ala Arg
            260                 265                 270
Arg Trp Ile Glu Ser Arg Met Gln Glu Gly Gly Phe Thr Cys
        275                 280                 285

<210> SEQ ID NO 18
<211> LENGTH: 238
<212> TYPE: PRT
<213> ORGANISM: YiaS-Ko

<400> SEQUENCE: 18

Met Leu Glu Gln Leu Lys Ala Glu Val Leu Ala Ala Asn Leu Ala Leu
 1               5                  10                  15
Pro Ala His Gly Leu Val Thr Phe Thr Trp Gly Asn Val Ser Ala Val
            20                  25                  30
Asp Glu Thr Arg Lys Leu Met Val Ile Lys Pro Ser Gly Val Glu Tyr
        35                  40                  45
Glu Val Met Thr Ala Asp Asp Met Val Val Glu Met Ala Ser Gly
    50                  55                  60
Lys Val Val Glu Gly Gly Lys Lys Pro Ser Ser Asp Thr Pro Thr His
65                  70                  75                  80
Leu Ala Leu Tyr Arg Arg Tyr Pro Gln Ile Gly Gly Ile Val His Thr
                85                  90                  95
His Ser Arg His Ala Thr Ile Trp Ser Gln Ala Gly Leu Asp Leu Pro
            100                 105                 110
Ala Trp Gly Thr Thr His Ala Asp Tyr Phe Tyr Gly Ala Ile Pro Cys
        115                 120                 125
Thr Arg Arg Met Thr Val Glu Glu Ile Asn Gly Glu Tyr Glu Tyr Gln
    130                 135                 140
Thr Gly Glu Val Ile Ile Lys Thr Phe Glu Gln Arg Gly Leu Asp Pro
145                 150                 155                 160
Ala Gln Ile Pro Ala Val Leu Val His Ser His Gly Pro Phe Ala Trp
                165                 170                 175
Gly Lys Asp Ala Ala Asp Ala Val His Asn Ala Val Val Leu Glu Glu
            180                 185                 190
Cys Ala Tyr Met Gly Leu Phe Ser Arg Gln Trp Pro Gln Leu Pro Asp
        195                 200                 205
Met Gln Ser Glu Leu Leu Asp Lys His Tyr Leu Arg Lys His Gly Ala
    210                 215                 220
Asn Ala Ile Thr Gly Lys Thr Ser Pro Ala Glu Leu Pro Gly
225                 230                 235

<210> SEQ ID NO 19
<211> LENGTH: 9334
<212> TYPE: DNA
<213> ORGANISM: yia

<400> SEQUENCE: 19
ggatccgcgg gcgcaaaggc ggagacgcca gaacagtcct ggtcctgctg atgggacacc      60
acgcaggcga cttcacaggt acggcagccg atgcacttct ccgcatccgc gagaataaac     120
cgattcatcc ttctccattg gggataaaaa cgcagagtgc cagaaaaaac ccgctttcct     180 ctcccttga tcctgaatgg agtcagcggc gttttctctc agatgtccgg gattatctgg     240
```

-continued

| | |
|---|---|
| tcatttgcct taaccttccc gcacggaaaa gcccagttcg cgagaaatcg cctctgccgt | 300 |
| atcgcgtagc ggcttgagta aattttctc tcccacctgc ttgaggcgcg atgttgatag | 360 |
| agagatagaa atggcataag gcacgcgccc atggatatca aaacgggga cagccaggca | 420 |
| cgacacgccc agctcgttct cttccctgtc catcgccata tttcgctcgc ggatctgcgc | 480 |
| cagttcatca tgcatcgcag gcaagccggt aatggtatta cgggtcagcg gctggataat | 540 |
| ctcctggtgt gaattccagt agctctcaac gtagtcagga tggccaaacg ccatataaat | 600 |
| cttgcccat tgccgagcag tacagcgcat gtgctggcca atataggcgc gcgtacgcag | 660 |
| cataccggtg gtcggctcca gcttataaat caggatcgcg tggtcatctt cacggctgga | 720 |
| gaagttcacc gtctcgccgg tggccaggtt aagcgcctca agatgcggcg ccgcgacgtg | 780 |
| gataatattc agcgacgaca acgccttttg gccaacgcgg ataaattttg tcgtcagcgc | 840 |
| atagctcccc gccgccgggg caggcgtcac gtacccgcag gactgcagcc cctgtaataa | 900 |
| gcgatgaacg gtacttttgt tcagtcccgc cagttccgac agatgcgcca cgggacagcc | 960 |
| atttggataa ttactcagga tctcaattag catcaaccca cgaaaaaggc tctgacttcc | 1020 |
| ggcaggcctc tctttatctt gcgtgttctc gctttctttt gtgcccatcg cttccgctcc | 1080 |
| cattttgtc gcgttcagat ggtagcgcaa agtgtgtttc agttcacgat ctgaaccgaa | 1140 |
| aaaacacaac tttatgattt ttatgatttt taaaaataac gctgcccgtt gatctgacaa | 1200 |
| aaattgatcg ctatatttga aatcagattt cgcatagtga aatttagaga taaaaaagcg | 1260 |
| atcaactctg accaggaaaa cagcaatgaa agtcacgttt gagcagttaa aagaggcatt | 1320 |
| caatcgggta ctgctggacg cgtgcgtcgc ccgggaaacc gccgatgcct gcgcagaaat | 1380 |
| gttgcccgc accaccgaat ccggcgtcta ttctcacggc gtgaaccgct ttcctcgctt | 1440 |
| catccagcag ttggataacg cgacattat ccctgaggct caaccgcagc gggtgaccac | 1500 |
| gctcggcgcc atcgaacagt gggatgctca gcgttccatc ggcaacctga cggcgaaaaa | 1560 |
| gatgatggat cgggccattg agctggcctc cgatcacggt atcggcctgg tcgccttacg | 1620 |
| taatgctaac cactgatgc gcggcggcag ctacggctgg caggcggcgg aaaaaggcta | 1680 |
| catcggtatc tgctggacca actccatcgc cgttatggcg ccatggggcg ctaaagagtg | 1740 |
| ccgtatcgg accaacccgc tgatcgtcgc cattccgtcg acgccgatca ccatggtgga | 1800 |
| tatgtcgatg tcgatgttct cctacggcat gctggaggtt aaccgccttg ccggccgcga | 1860 |
| actgcccgtg gacggcggat tcgacgatga cggtcgtttg accaaagagc cggggacgat | 1920 |
| cgagaaaaat cgccgcattt tacccatggg ctactggaaa ggttccggcc tgtcgatcgt | 1980 |
| gctggatatg attgccaccc tcctctccaa cggatcgtcg gttgccgaag tgacccagga | 2040 |
| aaacagcgat gaatatggcg tttcgcagat cttcatcgct attgaagtgg ataagctgat | 2100 |
| cgacggcgca acccgcgacg ccaagctgca acggattatg gatttcatca ccaccgccga | 2160 |
| gcgcgccgat gaaaatgtgg cggtccgtct tcctggccat gaatttaccc gtctgctgga | 2220 |
| tgaaaaccgc cgcaacggca ttaccgtcga tgacagcgta tgggccaaaa ttcaggcgct | 2280 |
| gtaaggagct cacccatgac agcgtatggg ccaaaattca ggcgctgtaa ggagctcacc | 2340 |
| catgattttt ggtcatattg ctcaacctaa tccgtgtcgt ctgccgcgg ccattgagcg | 2400 |
| ggcgcttgat ttcctgcgca cgacggattt ccacgcgctg gcacccggcg tcgtggaaat | 2460 |
| cgacggccaa aacatcttcg cgcaggttat cgacttaacc actcgcgatg ccgctgaaaa | 2520 |
| tcgtccggag gtccaccgtc gctatctgga tatccagttt ctggcatcgg gcgaagaaaa | 2580 |
| aatcggtatc gccattgata ccggcaataa tcaaatcagc gaatctttat tagaacagcg | 2640 |

```
cgatattatt ttttatcacg acagcgaaca tgaatcgttc tttgaaatga cgccaggcaa    2700
ctatgcgata tttttcccgc aagatgttca tcgtcctgga tgtaataaaa ctgtagccac    2760
gccgatccgc aaaatagtcg ttaaagtcgc tatttcagtt ttataagaag gagcacaaaa    2820
tgaattcgaa taataccggt tacattatcg gtgcgtaccc ctgtgccccc tgtgcaccct    2880
catttcacca aaagagtgaa gaggaagaga tggaattctg gcggcagctc tccgacaccc    2940
cggatattcg cgggctggag caaccctgcc taccctgcct tgaacatctt catccgctcg    3000
gcgacgagtg gttattgcgc catacccgg  gacactggca gattgtcgtt accgccatca    3060
tggaaaccat gcgccgccgc ggtgaaaacg gcggctttgg gctggcgtcc agcgacgaaa    3120
cgcagcgcaa agcctgcgtg gagtactatc gccacctgca gcagaagatc gctaaaatca    3180
atggcaatac cgccggaaag gtcattgccc ttgagcttca cgccgccccg ctggcgggca    3240
atgccaacgt ggctcaggct accgacgcct ttgcccgttc attaaaagaa attacccgct    3300
gggactggtc ctgcgagctg gtgctggagc actgcgacgc gatgaccggc agcgcgccgc    3360
gcaaaggatt tttgccgtta gaaaacgtgc tggaagccat tgccgattat gacgttggca    3420
tttgtattaa ctgggcgcgt tcggccattg aagggcggaa taccgtgcta ccgctcaccc    3480
atacgcagca ggtaaaacgg gcaggaaagc tcggcgcgct gatgttttct ggcacgacgc    3540
agaccggcga gtacggcgaa tggcaggatt tacacgcgcc gttcgcgcct ttctgcccgc    3600
agagcctgat gaccaccgaa cacgctcgtg aattatttgc ctgcgcagga accgccccc    3660
tgcaattttc aggcattaaa ttactggaaa ttaatgccag cgcaaacgtt gatcatcgca    3720
tcgcgatatt acgcgacggc atctccgcgc taaaacaagc acaataataa taatcacctt    3780
catcaccaga atatttttaa tattacgaga ctataaagat gaatataacc tctaactcta    3840
caaccaaaga tataccgcgc cagcgctggt taagaatcat tccgcctata ctgatcactt    3900
gtattatttc ttatatggac cgggtcaata ttgcctttgc gatgcccgga ggtatggatg    3960
ccgacttagg tatttccgcc accatggcgg ggctggcggg cggtattttc tttatcggtt    4020
atctatttt  acaggttccc ggcgggaaaa ttgccgttca cggtagcggt aagaaattta    4080
tcggctggtc gctggtcgcc tgggcggtca tctccgtgct gacggggtta attaccaatc    4140
agtaccagct gctggccctg cgcttcttac tgggcgtggc ggaaggcggt atgctgccgg    4200
tcgttctcac gatgatcagt aactggttcc ccgacgctga acgcggtcgc gccaacgcga    4260
ttgtcattat gtttgtgccg attgccggga ttatcaccgc cccactctca ggctggatta    4320
tcacggttct cgactggcgc tggctgtttta ttatcgaagg tttgctctcg ctggttgttc    4380
tggttctgtg ggcatacacc atctatgacc gtccgcagga agcgcgctgg atttccgaag    4440
cagagaagcg ctatctggtc gagacgctgg ccgcggagca aaaagccatt gccggcaccg    4500
aggtgaaaaa cgcctctctg agcgccgttc tctccgacaa accatgtgg  cagcttatcg    4560
ccctgaactt cttctaccag accggcattt acggctacac cctgtggcta cccaccattc    4620
tgaaagaatt gacccatagc agcatggggc aggtcggcat gcttgccatt ctgccgtacg    4680
tcggcgccat tgctgggatg ttcctgtttt cctcccttttc agaccgaacc ggtaaacgca    4740
agctgttcgt ctgcctgccg ctgattggct tcgctctgtg catgttcctg tcggtggcgc    4800
tgaaaaacca aatttggctc tcctatgccg cgctggtcgg ctgcggattc ttcctgcaat    4860
cggcggctgg cgtgttctgg accatcccgg cacgtctgtt cagcgcggaa atggcgggcg    4920
gcgcgcgcgg ggttatcaac gcgcttggca acctcggcgg attttgtggc ccttatgcgg    4980
```

-continued

```
tcggggtgct gatcacgttg tacagcaaag acgctggcgt ctattgcctg gcgatctccc    5040
tggcgctggc cgcgctgatg gcgctgctgc tgccggcgaa atgcgatgcc ggtgctgcgc    5100
cggtaaagac gataaatcca cataaacgca ctgcgtaaac tcgagcccgg cggcgctgcg    5160
cctgccgggc ctgcgaaata tgccgggttc accggtaac aatgagatgc gaaagatgag     5220
caagaaacag gccttctggc tgggtattga ttgcggcggc acctatctga agccggtttt    5280
atatgacgcc gaaggtcatg aacatggcat tgtgcggcaa gcgctacgga cgatgtcgcc    5340
cctgccgggt tacgccgaac gcgacatgcg ccagctctgg caacactgcg cggcgaccat    5400
tgccgggcta ttacagcagg caggtgtatc cggcgaacag attaaaggcg tgggcatctc    5460
cgctcagggt caagggctct ttctcctcga taagcaggat cggccgctgg gtaacgccat    5520
cctctcctcc gatcgtcggg cgctgaaaat cgttcagcgc tggcagcggg accgtattcc    5580
cgaacggctc tatcccgtta cccgccagac gctgtggacc ggacatccgg cttctttgct    5640
gcgctgggta aaagagaatg aaccccagcg ctacgcgcaa attggctgcg tgatgatggg    5700
gcatgactat ctgcgctggt gcttaaccgg cgcgaagggc tgcgaggaga gcaacatctc    5760
cgagtccaac ctctacaaca tggccatggg ccagtacgac ccgcgcctga ccgagtggct    5820
gggcatcggt gaaatcgata gcgcgctgcc ccccgttgta gggtcagccg aaatttgcgg    5880
ggagatcacc gctcaggcag ccgctttaac cggtctggcg gcgggtactc ccgtcgttgg    5940
cggcctgttt gacgtggtct ccaccgcccct ttgcgccggg attgaggatg agtcgaccct    6000
caatgcggtg atggggacct gggccgtcac tagcggtatc gctcacggcc tgcgcgacca    6060
tgaggcccac ccttacgtct atggccgcta cgtcaatgac ggccagtata tcgttcacga    6120
agccagcccg acctcatccg gcaacctcga atggtttacc gcccagtggg gcgatctctc    6180
gtttgatgag atcaatcagg ccgtcgccag cctgccgaaa gccgggagcg agctgttttt    6240
tctgccgttt ctgtatggca gcaacgccgg gctggagatg acctgcggct tttacggcat    6300
gcaggcgctg catacccgcg cgcacctgct gcaggcggtt tatgaaggcg tggtatttag    6360
ccatatgacc cacctcagcc gtatgcgcga acgctttaca aacgttcagg ccctgcgcgt    6420
caccggcggc ccggcgcact ccgacgtctg gatgcagatg ctggcggacg taagcggctt    6480
acgcattgaa ctcccgaagg tggaagagac cggctgtttt ggcgcggccc tcgccgctcg    6540
tgtcggtacc ggcgtatacc gcagctttag cgaagcccgg cgcgcccggc agcacccggt    6600
gcgcacgctg ctgcccgata tgaccgccca cgcgcgctat cagcgcaaat accgccacta    6660
cctgcatttg attgaagcac tacagggcta tcacgcccgt attaaggagc acgcattatg    6720
agccgaccat tactgcagct ggcgctcgac cataccagcc ttcaggctgc gcagcgcgat    6780
gtcgccctgc tacaggatca cgttgatatt gtggaggcgg gaaccatcct ctgcttaacc    6840
gaagggctta gcgcggttaa agccctgcgc gcccagtgtc cggggaagat catcgtcgcc    6900
gactggaaag tcgccgacgc cggtgaaacc ctggcgcagc aggcctttgg cgctggcgcc    6960
aactggatga ccatcatttg cgccgcaccg ctcgccacgg tcgagaaagg ccacgccgtg    7020
gcccaggcct gcggcggtga aattcagatg gagctgttcg gcaactggac gctggatgac    7080
gcccgcgcct ggtaccgtac cggcgtccat caggcgattt accatcgcgg acgcgatgcc    7140
caggccagcg ggcagcagtg ggggaggcg gatctggcgc gcatgaaagc gctgtccgat    7200
attggccttg agctatcgat taccggcggc attaccccag ccgatctacc gctgttcaaa    7260
gatatcaacg tcaaagcctt tattgccggg cgcgcgctgg caggcgccgc ccatccggcg    7320
cgggttgccg ccgaattcca cgcgcaaatc gacgctatct ggggagaaca gcatgcgtaa    7380
```

-continued

```
ccacccgtta ggtatttatg aaaaagcgct ggcgaaggat ctcagctggc ctgagcggct    7440
ggtactggcc aaaagctgcg gttttgattt tgtcgaaatg tcggtggacg agaccgatga    7500
acgcctttcg cgcctggagt ggaccccggc ccagcgcgca tcgctggtga gcgcgatgct    7560
ggaaaccgcg gtcgccattc cctcgatgtg cttgtccgcc catcgccgtt tcccctttgg    7620
cagccgcgat gaagcggtac gcgatcgggc gcgagagatt atgaccaaag ccatccgcct    7680
ggcgcgcgat ctggggatcc gcaccatcca gctggcgggt tacgacgtct attacgaaga    7740
gcatgatgaa ggcacccggc agcgttttgc cgaagggctg gcctgggcgg tagaacaggc    7800
cgccgccgcg caggtaatgc tggcggtgga gatcatggac accgcccttt atgaactcca    7860
cagcaaatgg aaaaagtggg acgagatgct ttcgtcaccg tggtttaccg tctacccgga    7920
cgtcggcaac ctcagcgcct ggggaaacga cgtcaccgcc gagctgaagc tgggcatcga    7980
tcgtatcgcc gccatccacc tgaaagatac gctgcccgtg accgacgata gccctggcca    8040
gttccgcgac gtgccgttcg gcgaaggatg cgtcgatttt gtcggcattt ttaagacgct    8100
gcgcgagctg aactaccgcg gttcattttt gattgagatg tggacggaga aagccagcga    8160
gccggtgctg gagattatcc aggcccggcg ctggatcgaa tcacggatgc aggaaggggg    8220
attcacatgt tagaacaact gaaagccgag gtactggcgg caaacctggc cctccccgca    8280
cacggcctgg tcacctttac ctggggcaac gtcagcgcgg tcgatgaaac gcgcaagctg    8340
atggtcatta agccttccgg cgtcgaatat gaggtgatga ccgccgacga tatggtggtc    8400
gtagagatgg ccagcggtaa agtcgttgaa ggcggtaaaa acccctcttc agatacgcca    8460
acgcatctgg cgctttatcg ccgctatccg cagatcggcg ggatcgtgca tacccactcc    8520
cgccacgcga cgatctggtc gcaggccggg ctcgatctcc ccgcctgggg caccacccac    8580
gccgactact tctatggcgc gatcccctgt acccgacgga tgaccgttga ggagattaac    8640
ggcgagtatg agtatcagac cggcgaggtg attatcaaaa cctttgaaca gcgcggcctg    8700
gatccggcgc aaatcccggc ggtattggtc cattcacacg gcccctttgc ctggggtaaa    8760
gacgccgccg acgccgtaca taacgccgtg gtgctggagg agtgcgccta catgggcctc    8820
ttctcgcgcc agtggccaca gctgccggat atgcagtctg aactgctcga taaacactat    8880
ctgcgtaaac acgcgcgcaa cgctattacg ggcaaaacta gtcccgcgga actccccgga    8940
taaggcgctt tggcccccgg gggaagcgtg caggatgttg ctgaactttc ccggagcgat    9000
gctgcgcatc tgtccgggct acgcgtcccc ggcgctctgc ggtcagcacc gcgcccggcg    9060
gaaaacccat caaccctacg ccgaattaat atgtccttgc agtaacgacg cttccacgcc    9120
gccggtccag gctggtgtgc ttgcggaaaa tcttgcgaaa atagccgaca tcgttaaacc    9180
cgcatttcat cgccacctcg gtaatcgaca gggaatcgct gataagcagc ttttccgccg    9240
cccttacccg ctgacggtgc agcgcttcgg taacgtcagc cggaaagcat ggcgataaac    9300
ggccccagat aacccgcgtt gcagtgcagc tcct                                9334
```

<210> SEQ ID NO 20
<211> LENGTH: 282
<212> TYPE: PRT
<213> ORGANISM: YiaJ-Ec

<400> SEQUENCE: 20

Met Gly Lys Glu Val Met Gly Lys Lys Glu Asn Glu Met Ala Gln Glu
 1               5                  10                  15

Lys Glu Arg Pro Ala Gly Ser Gln Ser Leu Phe Arg Gly Leu Met Leu

```
                20                  25                  30
Ile Glu Ile Leu Ser Asn Tyr Pro Asn Gly Cys Pro Leu Ala His Leu
             35                  40                  45

Ser Glu Leu Ala Gly Leu Asn Lys Ser Thr Val His Arg Leu Leu Gln
 50                  55                  60

Gly Leu Gln Ser Cys Gly Tyr Val Thr Thr Ala Pro Ala Ala Gly Ser
 65                  70                  75                  80

Tyr Arg Leu Thr Thr Lys Phe Ile Ala Val Gly Gln Lys Ala Leu Ser
                 85                  90                  95

Ser Leu Asn Ile Ile His Ile Ala Ala Pro His Leu Glu Ala Leu Asn
                100                 105                 110

Ile Ala Thr Gly Glu Thr Ile Asn Phe Ser Ser Arg Glu Asp Asp His
            115                 120                 125

Ala Ile Leu Ile Tyr Lys Leu Glu Pro Thr Thr Gly Met Leu Arg Thr
        130                 135                 140

Arg Ala Tyr Ile Gly Gln His Met Pro Leu Tyr Cys Ser Ala Met Gly
145                 150                 155                 160

Lys Ile Tyr Met Ala Phe Gly His Pro Asp Tyr Val Lys Ser Tyr Trp
                165                 170                 175

Glu Ser His Gln His Glu Ile Gln Pro Leu Thr Arg Asn Thr Ile Thr
            180                 185                 190

Glu Leu Pro Ala Met Phe Asp Glu Leu Ala His Ile Arg Glu Ser Gly
        195                 200                 205

Ala Ala Met Asp Arg Glu Glu Asn Glu Leu Gly Val Ser Cys Ile Ala
    210                 215                 220

Val Pro Val Phe Asp Ile His Gly Arg Val Pro Tyr Ala Val Ser Ile
225                 230                 235                 240

Ser Leu Ser Thr Ser Arg Leu Lys Gln Val Gly Glu Lys Asn Leu Leu
                245                 250                 255

Lys Pro Leu Arg Glu Thr Ala Gln Ala Ile Ser Asn Glu Leu Gly Phe
            260                 265                 270

Thr Val Arg Asp Asp Leu Gly Ala Ile Thr
            275                 280

<210> SEQ ID NO 21
<211> LENGTH: 268
<212> TYPE: PRT
<213> ORGANISM: YiaJ-Hi

<400> SEQUENCE: 21

Met Asn Ile Glu Val Lys Met Glu Lys Glu Lys Ser Leu Gly Asn Gln
 1               5                  10                  15

Ala Leu Ile Arg Gly Leu Arg Leu Leu Asp Ile Leu Ser Asn Tyr Pro
                20                  25                  30

Asn Gly Cys Pro Leu Ala Lys Leu Ala Glu Leu Ala Asn Leu Asn Lys
             35                  40                  45

Ser Thr Ala His Arg Leu Leu Gln Gly Leu Gln Asn Glu Gly Tyr Val
 50                  55                  60

Lys Pro Ala Asn Ala Ala Gly Ser Tyr Arg Leu Thr Ile Lys Cys Leu
65                  70                  75                  80

Ser Ile Gly Gln Lys Val Leu Ser Ser Met Asn Ile Ile His Val Ala
                85                  90                  95

Ser Pro Tyr Leu Glu Gln Leu Asn Leu Lys Leu Gly Glu Thr Ile Asn
            100                 105                 110
```

-continued

```
Phe Ser Lys Arg Glu Asp Asp His Ala Ile Met Ile Tyr Lys Leu Glu
        115                 120                 125

Pro Thr Asn Gly Met Leu Lys Thr Arg Ala Tyr Ile Gly Gln Tyr Leu
        130                 135                 140

Lys Leu Tyr Cys Ser Ala Met Gly Lys Ile Phe Leu Ala Tyr Glu Lys
145                 150                 155                 160

Lys Val Asp Tyr Leu Ser His Tyr Trp Gln Ser His Gln Arg Glu Ile
                165                 170                 175

Lys Lys Leu Thr Arg Tyr Thr Ile Thr Glu Leu Asp Asp Ile Lys Leu
                180                 185                 190

Glu Leu Glu Thr Ile Arg Gln Thr Ala Tyr Ala Met Asp Arg Glu Glu
                195                 200                 205

Asn Glu Leu Gly Val Thr Cys Ile Ala Cys Pro Ile Phe Asp Ser Phe
        210                 215                 220

Gly Gln Val Glu Tyr Ala Ile Ser Val Ser Met Ser Ile Tyr Arg Leu
225                 230                 235                 240

Asn Lys Phe Gly Thr Asp Ala Phe Leu Gln Glu Ile Arg Lys Thr Ala
                245                 250                 255

Glu Gln Ile Ser Leu Glu Leu Gly Tyr Glu Asn Ile
                260                 265

<210> SEQ ID NO 22
<211> LENGTH: 332
<212> TYPE: PRT
<213> ORGANISM: YiaK-Ec

<400> SEQUENCE: 22

Met Lys Val Thr Phe Glu Gln Leu Lys Ala Ala Phe Asn Arg Val Leu
1               5                   10                  15

Ile Ser Arg Gly Val Asp Ser Glu Thr Ala Asp Ala Cys Ala Glu Met
                20                  25                  30

Phe Ala Arg Thr Thr Glu Ser Gly Val Tyr Ser His Gly Val Asn Arg
            35                  40                  45

Phe Pro Arg Phe Ile Gln Gln Leu Glu Asn Gly Asp Ile Ile Pro Asp
        50                  55                  60

Ala Gln Pro Lys Arg Ile Thr Ser Leu Gly Ala Ile Glu Gln Trp Asp
65                  70                  75                  80

Ala Gln Arg Ser Ile Gly Asn Leu Thr Ala Lys Lys Met Met Asp Arg
                85                  90                  95

Ala Ile Glu Leu Ala Ala Asp His Gly Ile Gly Leu Val Ala Leu Arg
            100                 105                 110

Asn Ala Asn His Trp Met Arg Gly Gly Ser Tyr Gly Trp Gln Ala Ala
        115                 120                 125

Glu Lys Gly Tyr Ile Gly Ile Cys Trp Thr Asn Ser Ile Ala Val Met
        130                 135                 140

Pro Pro Trp Gly Ala Lys Glu Cys Arg Ile Gly Thr Asn Pro Leu Ile
145                 150                 155                 160

Val Ala Ile Pro Ser Thr Pro Ile Thr Met Val Asp Met Ser Met Ser
                165                 170                 175

Met Phe Ser Tyr Gly Met Leu Glu Val Asn Arg Leu Ala Gly Arg Gln
                180                 185                 190

Leu Pro Val Asp Gly Gly Phe Asp Asp Glu Gly Asn Leu Thr Lys Glu
            195                 200                 205

Pro Gly Val Ile Glu Lys Asn Arg Arg Ile Leu Pro Met Gly Tyr Trp
        210                 215                 220
```

```
Lys Gly Ser Gly Met Ser Ile Val Leu Asp Met Ile Ala Thr Leu Leu
225                 230                 235                 240

Ser Asp Gly Ala Ser Val Ala Glu Val Thr Gln Asp Asn Ser Asp Glu
                245                 250                 255

Tyr Gly Ile Ser Gln Ile Phe Ile Ala Ile Glu Val Asp Lys Leu Ile
                260                 265                 270

Asp Gly Pro Thr Arg Asp Ala Lys Leu Gln Arg Ile Met Asp Tyr Val
                275                 280                 285

Thr Ser Ala Glu Arg Ala Asp Glu Asn Gln Ala Ile Arg Leu Pro Gly
        290                 295                 300

His Glu Phe Thr Thr Leu Leu Ala Glu Asn Arg Arg Asn Gly Ile Thr
305                 310                 315                 320

Val Asp Asp Ser Val Trp Ala Lys Ile Gln Ala Leu
                325                 330
```

<210> SEQ ID NO 23
<211> LENGTH: 332
<212> TYPE: PRT
<213> ORGANISM: YiaK-Hi

<400> SEQUENCE: 23

```
Met Arg Val Ser Tyr Asp Glu Leu Lys Asn Glu Phe Lys Arg Val Leu
1               5                   10                  15

Leu Asp Arg Gln Leu Thr Glu Glu Leu Ala Glu Glu Cys Ala Thr Ala
                20                  25                  30

Phe Thr Asp Thr Thr Gln Ala Gly Ala Tyr Ser His Gly Ile Asn Arg
            35                  40                  45

Phe Pro Arg Phe Ile Gln Gln Leu Glu Gln Gly Asp Ile Val Pro Asn
    50                  55                  60

Ala Ile Pro Thr Lys Val Leu Ser Leu Gly Ser Ile Glu Gln Trp Asp
65                  70                  75                  80

Ala His Gln Ala Ile Gly Asn Leu Thr Ala Lys Lys Met Met Asp Arg
                85                  90                  95

Ala Ile Glu Leu Ala Ser Gln His Gly Val Gly Val Ile Ala Leu Arg
                100                 105                 110

Asn Ala Asn His Trp Met Arg Gly Gly Ser Tyr Gly Trp Gln Ala Ala
                115                 120                 125

Glu Lys Gly Tyr Ile Gly Ile Cys Trp Thr Asn Ala Leu Ala Val Met
130                 135                 140

Pro Pro Trp Gly Ala Lys Glu Cys Arg Ile Gly Thr Asn Pro Leu Ile
145                 150                 155                 160

Ile Ala Val Pro Thr Thr Pro Ile Thr Met Val Asp Met Ser Cys Ser
                165                 170                 175

Met Tyr Ser Tyr Gly Met Leu Glu Val His Arg Leu Ala Gly Arg Gln
                180                 185                 190

Thr Phe Val Asp Ala Gly Phe Asp Asp Glu Gly Asn Leu Thr Arg Asp
            195                 200                 205

Pro Ser Ile Val Glu Lys Asn Arg Arg Leu Leu Pro Met Gly Phe Trp
    210                 215                 220

Lys Gly Ser Gly Leu Ser Ile Val Leu Asp Met Ile Ala Thr Leu Leu
225                 230                 235                 240

Ser Asn Gly Glu Ser Thr Val Ala Val Thr Glu Asp Lys Asn Asp Glu
                245                 250                 255

Tyr Cys Val Ser Gln Val Phe Ile Ala Ile Glu Val Asp Arg Leu Ile
```

```
                     260                 265                 270
Asp Gly Lys Ser Lys Asp Glu Lys Leu Asn Arg Ile Met Asp Tyr Val
                275                 280                 285
Lys Thr Ala Glu Arg Ser Asp Pro Thr Gln Ala Val Arg Leu Pro Gly
            290                 295                 300
His Glu Phe Thr Thr Ile Leu Ser Asp Asn Gln Thr Asn Gly Ile Pro
305                 310                 315                 320
Val Asp Glu Arg Val Trp Ala Lys Leu Lys Thr Leu
                325                 330

<210> SEQ ID NO 24
<211> LENGTH: 155
<212> TYPE: PRT
<213> ORGANISM: YiaL-Ec

<400> SEQUENCE: 24

Met Ile Phe Gly His Ile Ala Gln Pro Asn Pro Cys Arg Leu Pro Ala
1               5                   10                  15
Ala Ile Glu Lys Ala Leu Asp Phe Leu Arg Ala Thr Asp Phe Asn Ala
            20                  25                  30
Leu Glu Pro Gly Val Val Glu Ile Asp Gly Lys Asn Ile Tyr Thr Gln
        35                  40                  45
Ile Ile Asp Leu Thr Thr Arg Glu Ala Val Asn Arg Pro Glu Val
    50                  55                  60
His Arg Arg Tyr Ile Asp Ile Gln Phe Leu Ala Trp Gly Glu Lys
65                  70                  75                  80
Ile Gly Ile Ala Ile Asp Thr Gly Asn Asn Lys Val Ser Glu Ser Leu
                85                  90                  95
Leu Glu Gln Arg Asn Ile Ile Phe Tyr His Asp Ser Glu His Glu Ser
            100                 105                 110
Phe Ile Glu Met Ile Pro Gly Ser Tyr Ala Ile Phe Phe Pro Gln Asp
        115                 120                 125
Val His Arg Pro Gly Cys Ile Met Gln Thr Ala Ser Glu Ile Arg Lys
    130                 135                 140
Ile Val Val Lys Val Ala Leu Thr Ala Leu Asn
145                 150                 155

<210> SEQ ID NO 25
<211> LENGTH: 155
<212> TYPE: PRT
<213> ORGANISM: YiaL-Hi

<400> SEQUENCE: 25

Met Ile Ile Ser Ser Leu Thr Asn Pro Asn Phe Lys Val Gly Leu Pro
1               5                   10                  15

Lys Val Ile Ala Glu Val Cys Asp Tyr Leu Asn Thr Leu Asp Leu Asn
            20                  25                  30

Ala Leu Glu Asn Gly Arg His Asp Ile Asn Asp Gln Ile Tyr Met Asn
        35                  40                  45

Val Met Glu Pro Glu Thr Ala Glu Pro Ser Ser Lys Lys Ala Glu Leu
    50                  55                  60

His His Glu Tyr Leu Asp Val Gln Val Leu Ile Arg Gly Thr Glu Asn
65                  70                  75                  80

Ile Glu Val Gly Ala Thr Tyr Pro Asn Leu Ser Lys Tyr Glu Asp Tyr
                85                  90                  95

Asn Glu Ala Asp Asp Tyr Gln Leu Cys Ala Asp Ile Asp Asp Lys Phe
            100                 105                 110

Thr Val Thr Met Lys Pro Lys Met Phe Ala Val Phe Tyr Pro Tyr Glu
        115                 120                 125

Pro His Lys Pro Cys Cys Val Val Asn Gly Lys Thr Glu Lys Ile Lys
    130                 135                 140

Lys Leu Val Val Lys Val Pro Val Lys Leu Ile
```

```
145                 150                 155

<210> SEQ ID NO 26
<211> LENGTH: 498
<212> TYPE: PRT
<213> ORGANISM: LyxK-Ec

<400> SEQUENCE: 26

Met Thr Gln Tyr Trp Leu Gly Leu Asp Cys Gly Gly Ser Trp Leu Lys
 1               5                  10                  15

Ala Gly Leu Tyr Asp Arg Glu Gly Arg Glu Ala Gly Val Gln Arg Leu
            20                  25                  30

Pro Leu Cys Ala Leu Ser Pro Gln Pro Gly Trp Ala Glu Arg Asp Met
        35                  40                  45

Ala Glu Leu Trp Gln Cys Cys Met Ala Val Ile Arg Ala Leu Leu Thr
    50                  55                  60

His Ser Gly Val Ser Gly Glu Gln Ile Val Gly Ile Gly Ile Ser Ala
 65                 70                  75                  80

Gln Gly Lys Gly Leu Phe Leu Leu Asp Lys Asn Asp Lys Pro Leu Gly
                85                  90                  95

Asn Ala Ile Leu Ser Ser Asp Arg Arg Ala Met Glu Ile Val Arg Arg
            100                 105                 110

Trp Gln Glu Asp Gly Ile Pro Glu Lys Leu Tyr Pro Leu Thr Arg Gln
        115                 120                 125

Thr Leu Trp Thr Gly His Pro Val Ser Leu Leu Arg Trp Leu Lys Glu
    130                 135                 140

His Glu Pro Glu Arg Tyr Ala Gln Ile Gly Cys Val Met Met Thr His
145                 150                 155                 160

Asp Tyr Leu Arg Trp Cys Leu Thr Gly Val Lys Gly Cys Glu Glu Ser
                165                 170                 175

Asn Ile Ser Glu Ser Asn Leu Tyr Asn Met Ser Leu Gly Glu Tyr Asp
            180                 185                 190

Pro Cys Leu Thr Asp Trp Leu Gly Ile Ala Glu Ile Asn His Ala Leu
        195                 200                 205

Pro Pro Val Val Gly Ser Ala Glu Ile Cys Gly Glu Ile Thr Ala Gln
    210                 215                 220

Thr Ala Ala Leu Thr Gly Leu Lys Ala Gly Thr Pro Val Val Gly Gly
225                 230                 235                 240

Leu Phe Asp Val Val Ser Thr Ala Leu Cys Ala Gly Ile Glu Asp Glu
                245                 250                 255

Phe Thr Leu Asn Ala Val Met Gly Thr Trp Ala Val Thr Ser Gly Ile
            260                 265                 270

Thr Arg Gly Leu Arg Asp Gly Glu Ala His Pro Tyr Val Tyr Gly Arg
        275                 280                 285

Tyr Val Asn Asp Gly Glu Phe Ile Val His Glu Ala Ser Pro Thr Ser
    290                 295                 300

Ser Gly Asn Leu Glu Trp Phe Thr Ala Gln Trp Gly Glu Ile Ser Phe
305                 310                 315                 320

Asp Glu Ile Asn Gln Ala Val Ala Ser Leu Pro Lys Ala Gly Gly Asp
                325                 330                 335

Leu Phe Phe Leu Pro Phe Leu Tyr Gly Ser Asn Ala Gly Leu Glu Met
            340                 345                 350

Thr Ser Gly Phe Tyr Gly Met Gln Ala Ile His Thr Arg Ala His Leu
        355                 360                 365
```

```
Leu Gln Ala Ile Tyr Glu Gly Val Val Phe Ser His Met Thr His Leu
        370                 375                 380

Asn Arg Met Arg Glu Arg Phe Thr Asp Val His Thr Leu Arg Val Thr
385                 390                 395                 400

Gly Gly Pro Ala His Ser Asp Val Trp Met Gln Met Leu Ala Asp Val
                    405                 410                 415

Ser Gly Leu Arg Ile Glu Leu Pro Gln Val Glu Thr Gly Cys Phe
            420                 425                 430

Gly Ala Ala Leu Ala Ala Arg Val Gly Thr Gly Val Tyr His Asn Phe
                435                 440                 445

Ser Glu Ala Gln Arg Asp Leu Arg His Pro Val Arg Thr Leu Leu Pro
        450                 455                 460

Asp Met Thr Ala His Gln Leu Tyr Gln Lys Lys Tyr Gln Arg Tyr Gln
465                 470                 475                 480

His Leu Ile Ala Ala Leu Gln Gly Phe His Ala Arg Ile Lys Glu His
                    485                 490                 495

Thr Leu
```

```
<210> SEQ ID NO 27
<211> LENGTH: 485
<212> TYPE: PRT
<213> ORGANISM: LyxK-Hi

<400> SEQUENCE: 27
```

```
Met His Tyr Tyr Leu Gly Ile Asp Cys Gly Gly Thr Phe Ile Lys Ala
1               5                   10                  15

Ala Ile Phe Asp Gln Asn Gly Thr Leu Gln Ser Ile Ala Arg Arg Asn
            20                  25                  30

Ile Pro Ile Ile Ser Glu Lys Pro Gly Tyr Ala Glu Arg Asp Met Asp
                35                  40                  45

Glu Leu Trp Asn Leu Cys Ala Gln Val Ile Gln Lys Thr Ile Arg Gln
50                  55                  60

Ser Ser Ile Leu Pro Gln Gln Ile Lys Ala Ile Gly Ile Ser Ala Gln
65                  70                  75                  80

Gly Lys Gly Ala Phe Phe Leu Asp Lys Asp Asn Lys Pro Leu Gly Arg
                85                  90                  95

Ala Ile Leu Ser Ser Asp Gln Arg Ala Tyr Glu Ile Val Gln Cys Trp
                100                 105                 110

Gln Lys Glu Asn Ile Leu Gln Lys Phe Tyr Pro Ile Thr Leu Gln Thr
            115                 120                 125

Leu Trp Met Gly His Pro Val Ser Ile Leu Arg Trp Ile Lys Glu Asn
130                 135                 140

Glu Pro Ser Arg Tyr Glu Gln Ile His Thr Ile Leu Met Ser His Asp
145                 150                 155                 160

Tyr Leu Arg Phe Cys Leu Thr Glu Lys Leu Tyr Cys Glu Glu Thr Asn
                165                 170                 175

Ile Ser Glu Ser Asn Phe Tyr Asn Met Arg Glu Gly Lys Tyr Asp Ile
            180                 185                 190

Gln Leu Ala Lys Leu Phe Gly Ile Thr Glu Cys Ile Asp Lys Leu Pro
        195                 200                 205

Pro Ile Ile Lys Ser Asn Lys Ile Ala Gly Tyr Val Thr Ser Arg Ala
        210                 215                 220

Ala Glu Gln Ser Gly Leu Val Glu Gly Ile Pro Val Val Gly Gly Leu
225                 230                 235                 240
```

-continued

Phe Asp Val Val Ser Thr Ala Leu Cys Ala Asp Leu Lys Asp Asp Gln
            245                 250                 255

His Leu Asn Val Val Leu Gly Thr Trp Ser Val Ser Gly Val Thr
            260                 265                 270

His Tyr Ile Asp Asp Asn Gln Thr Ile Pro Phe Val Tyr Gly Lys Tyr
            275                 280                 285

Pro Glu Lys Asn Lys Phe Ile Ile His Glu Ala Ser Pro Thr Ser Ala
    290                 295                 300

Gly Asn Leu Glu Trp Phe Val Asn Gln Phe Asn Leu Pro Asn Tyr Asp
305                 310                 315                 320

Asp Ile Asn His Glu Ile Ala Lys Leu Lys Pro Ala Ser Ser Ser Val
            325                 330                 335

Leu Phe Ala Pro Phe Leu Tyr Gly Ser Asn Ala Lys Leu Gly Met Gln
            340                 345                 350

Ala Gly Phe Tyr Gly Ile Gln Ser His His Thr Gln Ile His Leu Leu
            355                 360                 365

Gln Ala Ile Tyr Glu Gly Val Ile Phe Ser Leu Met Ser His Leu Glu
    370                 375                 380

Arg Met Gln Val Arg Phe Pro Asn Ala Ser Thr Val Arg Val Thr Gly
385                 390                 395                 400

Gly Pro Ala Lys Ser Glu Val Trp Met Gln Met Leu Ala Asp Ile Ser
            405                 410                 415

Gly Met Arg Leu Glu Ile Pro Asn Ile Glu Glu Thr Gly Cys Leu Gly
            420                 425                 430

Ala Ala Leu Met Ala Met Gln Ala Glu Ser Ala Val Glu Ile Ser Gln
            435                 440                 445

Ile Leu Asn Ile Asp Arg Lys Ile Phe Leu Pro Asp Lys Asn Gln Tyr
    450                 455                 460

Ser Lys Tyr Gln His Lys Tyr His Arg Tyr Leu Lys Phe Ile Glu Ala
465                 470                 475                 480

Leu Lys Asn Leu Asp
            485

<210> SEQ ID NO 28
<211> LENGTH: 220
<212> TYPE: PRT
<213> ORGANISM: YiaQ-Ec

<400> SEQUENCE: 28

Met Ser Arg Pro Leu Leu Gln Leu Ala Leu Asp His Ser Ser Leu Glu
1               5                   10                  15

Ala Ala Gln Arg Asp Val Thr Leu Leu Lys Asp Ser Val Asp Ile Val
            20                  25                  30

Glu Ala Gly Thr Ile Leu Cys Leu Asn Glu Gly Leu Gly Ala Val Lys
            35                  40                  45

Ala Leu Arg Glu Gln Cys Pro Asp Lys Ile Ile Val Ala Asp Trp Lys
    50                  55                  60

Val Ala Asp Ala Gly Glu Thr Leu Ala Gln Ala Phe Gly Ala Gly
65                  70                  75                  80

Ala Asn Trp Met Thr Ile Ile Cys Ala Ala Pro Leu Ala Thr Val Glu
            85                  90                  95

Lys Gly His Ala Met Ala Gln Arg Cys Gly Gly Glu Ile Gln Ile Glu
            100                 105                 110

Leu Phe Gly Asn Trp Thr Leu Asp Asp Ala Arg Asp Trp His Arg Ile
    115                 120                 125

```
Gly Val Arg Gln Ala Ile Tyr His Arg Gly Arg Asp Ala Gln Ala Ser
    130                 135                 140

Gly Gln Gln Trp Gly Glu Ala Asp Leu Ala Arg Met Lys Ala Leu Ser
145                 150                 155                 160

Asp Ile Gly Leu Glu Leu Ser Ile Thr Gly Ile Thr Pro Ala Asp
                165                 170                 175

Leu Pro Leu Phe Lys Asp Ile Arg Val Lys Ala Phe Ile Ala Gly Arg
            180                 185                 190

Ala Leu Ala Gly Ala Ala Asn Pro Ala Gln Val Ala Gly Asp Phe His
        195                 200                 205

Ala Gln Ile Asp Ala Ile Trp Gly Gly Ala Arg Ala
    210                 215                 220

<210> SEQ ID NO 29
<211> LENGTH: 225
<212> TYPE: PRT
<213> ORGANISM: YiaQ-Hi

<400> SEQUENCE: 29

Met Gly Lys Pro Leu Leu Gln Ile Ala Leu Asp Ala Gln Tyr Leu Glu
1               5                   10                  15

Thr Ala Leu Val Asp Val Lys Gln Ile Glu His Asn Ile Asp Ile Ile
            20                  25                  30

Glu Val Gly Thr Ile Leu Ala Cys Ser Glu Gly Met Arg Ala Val Arg
        35                  40                  45

Ile Leu Arg Ala Leu Tyr Pro Asn Gln Ile Leu Val Cys Asp Leu Lys
    50                  55                  60

Thr Thr Asp Ala Gly Ala Thr Leu Ala Lys Met Ala Phe Glu Ala Gly
65                  70                  75                  80

Ala Asp Trp Leu Thr Val Ser Ala Ala His Pro Ala Thr Lys Ala
                85                  90                  95

Ala Cys Gln Lys Val Ala Glu Glu Phe Asn Lys Ile Gln Pro Asn Leu
            100                 105                 110

Gly Val Pro Lys Glu Ile Gln Ile Glu Leu Tyr Gly Asn Trp Asn Phe
        115                 120                 125

Asp Glu Val Lys Asn Trp Leu Gln Leu Gly Ile Lys Gln Ala Ile Tyr
    130                 135                 140

His Arg Ser Arg Asp Ala Glu Leu Ser Gly Leu Ser Trp Ser Asn Gln
145                 150                 155                 160

Asp Ile Glu Asn Ile Glu Lys Leu Asp Ser Leu Gly Ile Glu Leu Ser
                165                 170                 175

Ile Thr Gly Gly Ile Thr Pro Asp Asp Leu His Leu Phe Lys Asn Thr
            180                 185                 190

Lys Asn Leu Lys Ala Phe Ile Ala Gly Arg Ala Leu Val Gly Lys Ser
        195                 200                 205

Gly Arg Glu Ile Ala Glu Gln Leu Lys Gln Lys Ile Gly Gln Phe Trp
    210                 215                 220

Ile
225

<210> SEQ ID NO 30
<211> LENGTH: 297
<212> TYPE: PRT
<213> ORGANISM: YiaR-Ec

<400> SEQUENCE: 30
```

```
Met Arg Lys Ser Thr Leu Ser Gly Glu Val Arg Val Arg Asn His Gln
  1               5                  10                  15

Leu Gly Ile Tyr Glu Lys Ala Leu Ala Lys Asp Leu Ser Trp Pro Glu
             20                  25                  30

Arg Leu Val Leu Ala Lys Ser Cys Gly Phe Asp Phe Val Glu Met Ser
             35                  40                  45

Val Asp Glu Thr Asp Glu Arg Leu Ser Arg Leu Asp Trp Ser Ala Ala
     50                  55                  60

Gln Arg Thr Ser Leu Val Ala Ala Met Ile Glu Thr Gly Val Gly Ile
 65              70                  75                      80

Pro Ser Met Cys Leu Ser Ala His Arg Arg Phe Pro Phe Gly Ser Arg
                 85                  90                  95

Asp Glu Ala Val Arg Glu Arg Ala Arg Glu Ile Met Ser Lys Ala Ile
                100                 105                 110

Arg Leu Ala Arg Asp Leu Gly Ile Arg Thr Ile Gln Leu Ala Gly Tyr
            115                 120                 125

Asp Val Tyr Tyr Glu Asp His Asp Glu Gly Thr Arg Gln Arg Phe Ala
            130                 135                 140

Glu Gly Leu Ala Trp Ala Val Glu Gln Ala Ala Ala Ser Gln Val Met
145                 150                 155                 160

Leu Ala Val Glu Ile Met Asp Thr Ala Phe Met Asn Ser Ile Ser Lys
                    165                 170                 175

Trp Lys Lys Trp Asp Glu Met Leu Ala Ser Pro Trp Phe Thr Val Tyr
                180                 185                 190

Pro Asp Val Gly Asn Leu Ser Ala Trp Gly Asn Asp Val Pro Ala Glu
            195                 200                 205

Leu Lys Leu Gly Ile Asp Arg Ile Ala Ile His Leu Lys Asp Thr
210                 215                 220

Gln Pro Val Thr Gly Gln Ser Pro Gly Gln Phe Arg Asp Val Pro Phe
225                 230                 235                 240

Gly Glu Gly Cys Val Asp Phe Val Gly Ile Phe Lys Thr Leu His Lys
                245                 250                 255

Leu Asn Tyr Arg Gly Ser Phe Leu Ile Glu Met Trp Thr Glu Lys Ala
            260                 265                 270

Lys Glu Pro Val Leu Glu Ile Ile Gln Ala Arg Arg Trp Ile Glu Ala
            275                 280                 285

Arg Met Gln Glu Ala Gly Phe Ile Cys
            290                 295
```

<210> SEQ ID NO 31
<211> LENGTH: 286
<212> TYPE: PRT
<213> ORGANISM: YiaR-Hi

<400> SEQUENCE: 31

```
Met Lys Lys His Lys Ile Gly Ile Tyr Glu Lys Ala Leu Pro Lys Asn
  1               5                  10                  15

Ile Thr Trp Gln Glu Arg Leu Ser Leu Ala Lys Ala Cys Gly Phe Glu
             20                  25                  30

Phe Ile Glu Met Ser Ile Asp Glu Ser Asn Asp Arg Leu Ser Arg Leu
             35                  40                  45

Asn Trp Thr Lys Ser Glu Arg Ile Ala Leu His Gln Ser Ile Ile Gln
     50                  55                  60

Ser Gly Ile Thr Ile Pro Ser Met Cys Leu Ser Ala His Arg Arg Phe
```

```
                65                  70                  75                  80
Pro Phe Gly Ser Lys Asp Lys Ile Arg Gln Lys Ser Phe Glu Ile
                85                  90                  95
Met Glu Lys Ala Ile Asp Leu Ser Val Asn Leu Gly Ile Arg Thr Ile
                100                 105                 110
Gln Leu Ala Gly Tyr Asp Val Tyr Glu Lys Gln Asp Glu Glu Thr
                115                 120                 125
Ile Lys Tyr Phe Gln Glu Gly Ile Glu Phe Ala Val Thr Leu Ala Ala
    130                 135                 140
Ser Ala Gln Val Thr Leu Ala Val Glu Ile Met Asp Thr Pro Phe Met
145                 150                 155                 160
Ser Ser Ile Ser Arg Trp Lys Lys Trp Asp Thr Ile Ile Asn Ser Pro
                165                 170                 175
Trp Phe Thr Val Tyr Pro Asp Ile Gly Asn Leu Ser Ala Trp Asn Asn
                180                 185                 190
Asn Ile Glu Glu Leu Thr Leu Gly Ile Asp Lys Ile Ser Ala Ile
                195                 200                 205
His Leu Lys Asp Thr Tyr Pro Val Thr Glu Thr Ser Lys Gly Gln Phe
    210                 215                 220
Arg Asp Val Pro Phe Gly Gln Gly Cys Val Asp Phe Val His Phe Phe
225                 230                 235                 240
Ser Leu Leu Lys Lys Leu Asn Tyr Arg Gly Ala Phe Leu Ile Glu Met
                245                 250                 255
Trp Thr Glu Lys Asn Glu Glu Pro Leu Leu Glu Ile Ile Gln Ala Arg
                260                 265                 270
Lys Trp Ile Val Gln Gln Met Glu Lys Ala Gly Leu Leu Cys
                275                 280                 285

<210> SEQ ID NO 32
<211> LENGTH: 231
<212> TYPE: PRT
<213> ORGANISM: YiaS-Ec

<400> SEQUENCE: 32

Met Leu Glu Gln Leu Lys Ala Asp Val Leu Ala Ala Asn Leu Ala Leu
1               5                   10                  15
Pro Ala His His Leu Val Thr Phe Thr Trp Gly Asn Val Ser Ala Val
                20                  25                  30
Asp Glu Thr Arg Gln Trp Met Val Ile Lys Pro Ser Gly Val Glu Tyr
                35                  40                  45
Asp Val Met Thr Ala Asp Asp Met Val Val Glu Ile Ala Ser Gly
    50                  55                  60
Lys Val Val Glu Gly Ser Lys Lys Pro Ser Ser Asp Thr Pro Thr His
65                  70                  75                  80
Leu Ala Leu Tyr Arg Arg Tyr Ala Glu Ile Gly Gly Ile Val His Thr
                85                  90                  95
His Ser Arg His Ala Thr Ile Trp Ser Gln Ala Gly Leu Asp Leu Pro
                100                 105                 110
Ala Trp Gly Thr Thr His Ala Asp Tyr Phe Tyr Gly Ala Ile Pro Cys
                115                 120                 125
Thr Arg Gln Met Thr Ala Glu Glu Ile Asn Gly Glu Tyr Glu Tyr Gln
    130                 135                 140
Thr Gly Glu Val Ile Ile Glu Thr Phe Glu Glu Arg Gly Arg Ser Pro
145                 150                 155                 160
```

-continued

```
Ala Gln Ile Pro Ala Val Leu Val His Ser His Gly Pro Phe Ala Trp
            165                 170                 175

Gly Lys Asn Ala Ala Asp Ala Val His Asn Ala Val Val Leu Glu Glu
            180                 185                 190

Cys Ala Tyr Met Gly Leu Phe Ser Arg Gln Leu Ala Pro Gln Leu Pro
        195                 200                 205

Ala Met Gln Asn Glu Leu Leu Asp Lys His Tyr Leu Arg Lys His Gly
    210                 215                 220

Ala Asn Ala Tyr Tyr Gly Gln
225                 230

<210> SEQ ID NO 33
<211> LENGTH: 231
<212> TYPE: PRT
<213> ORGANISM: YiaS-Hi

<400> SEQUENCE: 33

Met Leu Ala Gln Leu Lys Lys Glu Val Phe Glu Ala Asn Leu Ala Leu
1               5                   10                  15

Pro Lys His His Leu Val Thr Phe Thr Trp Gly Asn Val Ser Ala Ile
            20                  25                  30

Asp Arg Glu Lys Asn Leu Val Val Ile Lys Pro Ser Gly Val Asp Tyr
        35                  40                  45

Asp Val Met Thr Glu Asn Asp Met Val Val Asp Leu Phe Thr Gly
    50                  55                  60

Asn Ile Val Glu Gly Asn Lys Lys Pro Ser Ser Asp Thr Pro Thr His
65                  70                  75                  80

Leu Glu Leu Tyr Arg Gln Phe Pro His Ile Gly Gly Ile Val His Thr
                85                  90                  95

His Ser Arg His Ala Thr Ile Trp Ala Gln Ala Gly Leu Asp Ile Ile
            100                 105                 110

Glu Val Gly Thr Thr His Gly Asp Tyr Phe Tyr Gly Thr Ile Pro Cys
        115                 120                 125

Thr Arg Gln Met Thr Thr Lys Glu Ile Lys Gly Asn Tyr Glu Leu Glu
    130                 135                 140

Thr Gly Lys Val Ile Val Glu Thr Phe Leu Ser Arg Gly Ile Glu Pro
145                 150                 155                 160

Asp Asn Ile Pro Ala Val Leu Val His Ser His Gly Pro Phe Ala Trp
            165                 170                 175

Gly Lys Asp Ala Asn Asn Ala Val His Asn Ala Val Val Leu Glu Glu
            180                 185                 190

Val Ala Tyr Met Asn Leu Phe Ser Gln Gln Leu Asn Pro Tyr Leu Ser
        195                 200                 205

Pro Met Gln Lys Asp Leu Leu Asp Lys His Tyr Leu Arg Lys His Gly
    210                 215                 220

Gln Asn Ala Tyr Tyr Gly Gln
225                 230
```